United States Patent
Hwang et al.

(10) Patent No.: US 9,705,090 B2
(45) Date of Patent: Jul. 11, 2017

(54) CONDENSED CYCLIC COMPOUND AND ORGANIC LIGHT-EMITTING DEVICE INCLUDING THE SAME

(71) Applicants: SAMSUNG DISPLAY CO., LTD., Yongin, Gyeonggi-Do (KR); PUSAN NATIONAL UNIVERSITY INDUSTRY-UNIVERSITY COOPERATION FOUNDATION, Busan (KR)

(72) Inventors: Jin-Soo Hwang, Yongin (KR); Myeong-Suk Kim, Yongin (KR); Sung-Wook Kim, Yongin (KR); Sam-Il Kho, Yongin (KR); Hong-Suk Seo, Busan (KR)

(73) Assignees: Samsung Display Co., Ltd., Yongin-si (KR); Pusan National University Industry-University Cooperation Foundation, Bursan (KR)

( * ) Notice: Subject to any disclaimer, the term of this patent is extended or adjusted under 35 U.S.C. 154(b) by 211 days.

(21) Appl. No.: 14/596,574

(22) Filed: Jan. 14, 2015

(65) Prior Publication Data

US 2015/0364695 A1 Dec. 17, 2015

(30) Foreign Application Priority Data

Jun. 16, 2014 (KR) ........................ 10-2014-0072969

(51) Int. Cl.
*H01L 51/00* (2006.01)
*C07D 519/00* (2006.01)
*H01L 51/50* (2006.01)

(52) U.S. Cl.
CPC ........ *H01L 51/0071* (2013.01); *C07D 519/00* (2013.01); *H01L 51/0052* (2013.01); *H01L 51/0059* (2013.01); *H01L 51/5056* (2013.01)

(58) Field of Classification Search
None
See application file for complete search history.

(56) References Cited

U.S. PATENT DOCUMENTS

| | | |
|---|---|---|
| 2008/0262183 A1 | 10/2008 | Lehmann |
| 2011/0177007 A1 | 7/2011 | Rajagopalan et al. |
| 2012/0097924 A1 | 4/2012 | Kim et al. |
| 2012/0305082 A1 | 12/2012 | Moon et al. |

FOREIGN PATENT DOCUMENTS

| | | |
|---|---|---|
| JP | 2013028585 A * | 2/2013 |
| JP | 2013-512985 | 4/2013 |
| KR | 10-2011-0132721 | 12/2011 |
| KR | 10-2012-0043623 | 5/2012 |
| KR | 10-1144358 | 5/2012 |

OTHER PUBLICATIONS

Machine English translation of Suga et al. (JP 2013-028585 A). Feb. 17, 2017.*
Korean Patent Abstracts Publication No. 10-2010-0122798 A, dated Nov. 23, 2010, for KR 10-1144358, 1 page.

* cited by examiner

*Primary Examiner* — J. L. Yang
(74) *Attorney, Agent, or Firm* — Lewis Roca Rothgerber Christie LLP

(57) ABSTRACT

An organic light-emitting device includes a first electrode, a second electrode, and an organic layer between the first electrode and the second electrode and including at least one condensed cyclic compound represented by Formula 1:

Formula 1

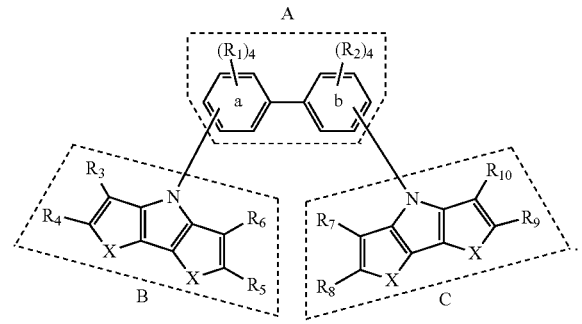

The organic light-emitting device including the condensed cyclic compound represented by Formula 1 may have low driving voltage, high efficiency, high brightness, and long lifespan.

20 Claims, 1 Drawing Sheet

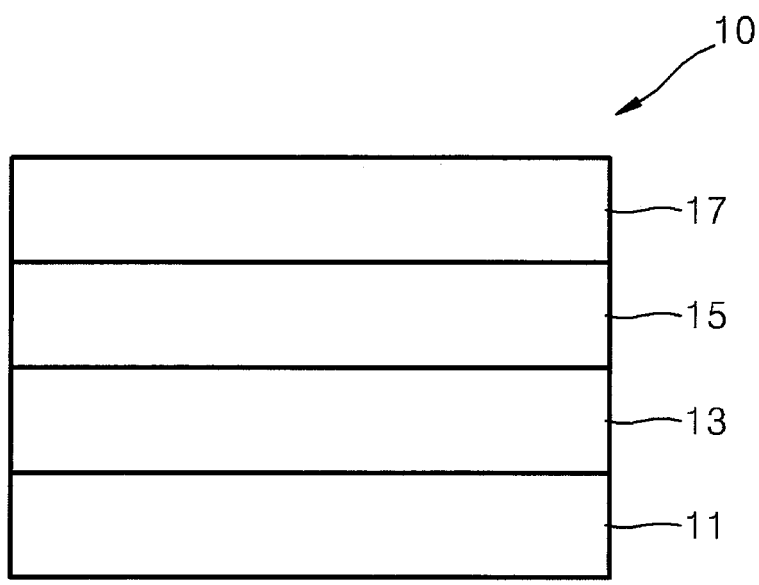

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0072969, filed on Jun. 16, 2014, in the Korean Intellectual Property Office, the entire content of which is incorporated herein by reference.

BACKGROUND

1. Field

One or more aspects of embodiments of the present invention relate to a condensed cyclic compound and an organic light-emitting device including the same.

2. Description of the Related Art

Organic light emitting devices are self-emission devices that have wide viewing angles, high contrast ratios, and short response times, and have excellent brightness, driving voltage, and response speed characteristics, as well as the ability to produce full-color images.

The organic light-emitting device may include a first electrode positioned on a substrate, and a hole transport region, an emission layer, an electron transport region, and a second electrode, sequentially positioned on the first electrode. Holes from the first electrode may pass through the hole transport region toward the emission layer, and electrons from the second electrode may pass through the electron transport region toward the emission layer. Carriers (i.e. holes and electrons), can recombine in the emission layer to produce excitons. When these excitons drop from an excited state to a ground state, light is generated.

Conventional arylamine hole carrier materials for a hole transport region have good transport efficiency, but may have short lifespan.

SUMMARY

One or more aspects of embodiments of the present invention are directed to a novel condensed cyclic compound and an organic light-emitting device including the same. One or more aspects of embodiments of the present invention provide an organic light-emitting device with a condensed cyclic compound that provides both improved hole injection and transport capacity, and long lifespan to the organic light-emitting device.

In one embodiment, a condensed cyclic compound is represented by Formula 1:

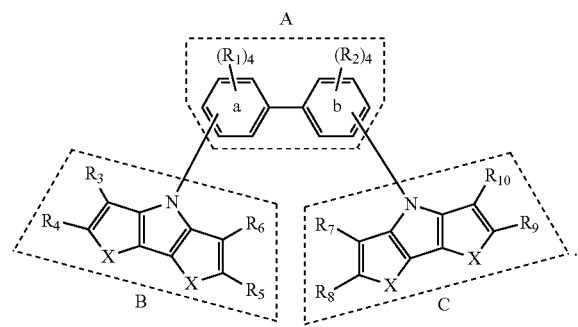

Formula 1

In Formula 1,

X is an oxygen (O) atom or a sulfur (S) atom;

$R_1$ to $R_{10}$ are each independently selected from a hydrogen, a deuterium, a halogen atom, a cyano group, a nitro group, a hydroxyl group, a carboxyl acid, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_1$-$C_{30}$ heteroaryl group (e.g. a substituted or unsubstituted $C_2$-$C_{30}$ heteroaryl group), a substituted or unsubstituted $C_6$-$C_{30}$ aryloxy group, a substituted or unsubstituted $C_6$-$C_{30}$ arylthio group, and a monovalent $C_6$-$C_{30}$ non-aromatic condensed polycyclic group, a plurality of $R_1$ and a plurality of $R_2$ are each independent (i.e. each $R_1$ of the plurality of $R_1$ may be the same as or different from another $R_1$, and each $R_2$ of the plurality of $R_2$ may be the same as or different from another $R_2$), one or more of the plurality of $R_1$ and the plurality of $R_2$ are linked to each other to form a condensed ring;

at least one substituent of the substituted $C_1$-$C_{10}$ alkyl group, substituted $C_2$-$C_{10}$ alkenyl group, substituted $C_2$-$C_{10}$ alkynyl group, substituted $C_1$-$C_{10}$ alkoxy group, substituted $C_3$-$C_{10}$ cycloalkyl group, substituted $C_3$-$C_{10}$ cycloalkenyl group, substituted $C_3$-$C_{10}$ heterocycloalkyl group, substituted $C_3$-$C_{10}$ heterocycloalkenyl group, substituted $C_6$-$C_{30}$ aryl group, substituted $C_1$-$C_{30}$ heteroaryl group (e.g. substituted $C_2$-$C_{30}$ heteroaryl group), substituted $C_6$-$C_{30}$ aryloxy group, and substituted $C_6$-$C_{30}$ arylthio group is selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl, and a $C_1$-$C_{10}$ alkoxy group;

a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, $C_3$-$C_{10}$ a cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{21}$)($Q_{22}$), —Si($Q_{23}$)($Q_{24}$)($Q_{25}$), and —B($Q_{26}$)($Q_{27}$); and —Si($Q_{31}$)($Q_{32}$)($Q_{33}$) and —B($Q_{34}$)($Q_{35}$), and $Q_{11}$ to $Q_{17}$, $Q_{21}$ to $Q_{27}$, and $Q_{31}$ to $Q_{35}$ are each independently selected from a hydrogen, a $C_1$-$C_{10}$ alkyl group, a $C_2$-$C_{10}$ alkenyl group, a $C_2$-$C_{10}$ alkynyl group, a $C_r$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

According to one or more embodiments of the present invention, an organic light-emitting device includes a first electrode, a second electrode facing the first electrode, and an organic layer between the first electrode and the second electrode and including an emission layer, wherein the organic layer includes at least one condensed cyclic compound described above.

BRIEF DESCRIPTION OF THE DRAWINGS

These and/or other aspects will become apparent and more readily appreciated from the following description of the embodiments, taken in conjunction with the accompanying drawing, which is a schematic view of an organic light-emitting device according to an embodiment of the present invention.

DETAILED DESCRIPTION

Reference will now be made in more detail to embodiments, examples of which are illustrated in the accompanying drawing, wherein like reference numerals refer to like elements throughout. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention."

A condensed cyclic compound according to an embodiment of the present invention is represented by Formula 1:

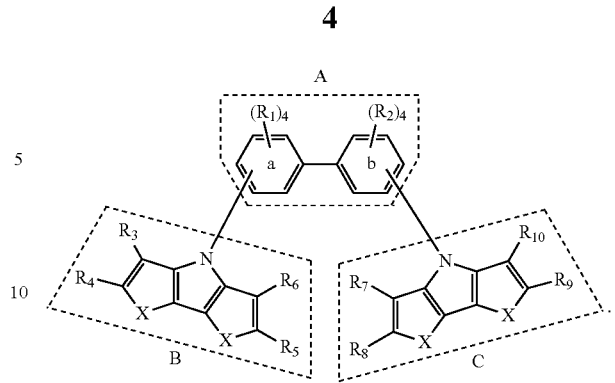

In Formula 1,

X is an oxygen (O) atom or a sulfur (S) atom;

$R_1$ to $R_{10}$ are each independently selected from a hydrogen, a deuterium, a halogen atom, a cyano group, a nitro group, a hydroxyl group, a carboxyl acid, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_1$-$C_{30}$ heteroaryl group (e.g. a substituted or unsubstituted $C_2$-$C_{30}$ heteroaryl group), a substituted or unsubstituted $C_6$-$C_{30}$ aryloxy group, a substituted or unsubstituted $C_6$-$C_{30}$ arylthio group, and a substituted or unsubstituted monovalent $C_6$-$C_{30}$ non-aromatic condensed polycyclic group, a plurality of $R_1$ ($R_1$s) and a plurality of $R_2$ ($R_2$s) are each independent (i.e. each $R_1$ of the plurality of $R_1$ may be the same as or different from another $R_1$, and each $R_2$ of the plurality of $R_2$ may be the same as or different from another $R_2$), one or more of the plurality of $R_1$ and the plurality of $R_2$ are linked to each other to form a condensed ring;

at least one substituent of the substituted $C_1$-$C_{10}$ alkyl group, substituted $C_2$-$C_{10}$ alkenyl group, substituted $C_2$-$C_{10}$ alkynyl group, substituted $C_1$-$C_{10}$ alkoxy group, substituted $C_3$-$C_{10}$ cycloalkyl group, substituted $C_3$-$C_{10}$ cycloalkenyl group, substituted $C_3$-$C_{10}$ heterocycloalkyl group, substituted $C_3$-$C_{10}$ heterocycloalkenyl group, substituted $C_6$-$C_{30}$ aryl group, substituted $C_1$-$C_{30}$ heteroaryl group (e.g. substituted $C_2$-$C_{30}$ heteroaryl group), substituted $C_6$-$C_{30}$ aryloxy group, substituted $C_6$-$C_{30}$ arylthio group, and substituted monovalent $C_6$-$C_{30}$ non-aromatic condensed polycyclic group is selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl, and a $C_1$-$C_{10}$ alkoxy group;

a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, $C_3$-$C_{10}$ a cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{21}$)($Q_{22}$), —Si($Q_{23}$)($Q_{24}$)($Q_{25}$), and —B($Q_{26}$)($Q_{27}$); and —Si($Q_{31}$)($Q_{32}$)($Q_{33}$) and —B($Q_{34}$)($Q_{35}$), and $Q_{11}$ to $Q_{17}$, $Q_{21}$ to $Q_{27}$, and $Q_{31}$ to $Q_{35}$ are each independently selected from a hydrogen, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

In one embodiment, the plurality of $R_1$ are each independently selected from a hydrogen and a $C_1$-$C_{10}$ alkyl group.

In another embodiment, at least one of the plurality of $R_1$ is selected from a hydrogen and a $C_1$-$C_{10}$ alkyl group, and two or more of the plurality of $R_1$ (different from the at least one of the plurality of $R_1$) are linked to each other to form a substituted or unsubstituted naphthylene group or anthrylene group that is fused together with an 'a' benzene ring, and at least one substituent of the substituted naphthylene group and/or the substituted anthrylene group may be selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

In one embodiment, the plurality of $R_2$ are each independently selected from a hydrogen and a $C_1$-$C_{10}$ alkyl group.

In another embodiment, at least one of the plurality of $R_2$ is selected from a hydrogen and a $C_1$-$C_{10}$ alkyl group, and two or more of the plurality of $R_2$ (different from the at least one of the plurality of $R_2$) are linked to each other to form a substituted or unsubstituted naphthylene group or anthrylene group that is fused together with a 'b' benzene ring, and at least one substituent of the substituted naphthylene group and/or the substituted anthrylene group may be selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

In one embodiment, at least one of the plurality of $R_1$ and $R_2$ is selected from a hydrogen and a $C_1$-$C_{10}$ alkyl group, and at least another one $R_1$ of the plurality of $R_1$ and at least another one $R_2$ of the plurality of $R_2$ are linked to each other to form a substituted or unsubstituted $C_{13}$-$C_{30}$ condensed ring that is fused together with the 'a' and 'b' benzene rings, where at least one substituent of the substituted $C_{13}$-$C_{30}$ condensed ring may be selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

In one embodiment, $R_3$ to $R_{10}$ may be each independently selected from a hydrogen, a methyl group, an ethyl group, a propyl group, a butyl group, a pentyl group, a hexyl group, a heptyl group, an octyl group, a nonyl group, a decyl group, a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, a benzocarbazolyl group, and a dibenzacridinyl group; and a methyl group, an ethyl group, a propyl group, a butyl group, a pentyl group, a hexyl group, a heptyl group, an octyl group, a nonyl group, and a decyl group, each substituted with at least one selected from a deuterium, a halogen atom, a hydroxyl group, a cyano group, a nitro group, and an amino group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, a benzimidazolyl group, bensoxazolyl group, an benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, benzoquinolyl group, a phenazinyl group, a dibenzosilolyl group, a dibenzothiophenyl group and a benzocarbazolyl group, each substituted with at least one selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_4$-$C_{30}$ heteroaryl group, a $C_5$-$C_{30}$ aryloxy group, a $C_5$-$C_{30}$ arylthio group, and —Si($Q_{31}$)($Q_{32}$)($Q_{33}$) (where $Q_{31}$ to $Q_{33}$ are each independently selected from a hydrogen, a $C_1$-$C_{10}$ alkyl group, a $C_1$-$C_{10}$ alkoxy group, and a $C_6$-$C_{20}$ aryl group).

In one embodiment, an A part represented by a dotted line box in Formula 1 may be selected from Formulae 2A to 2AA:

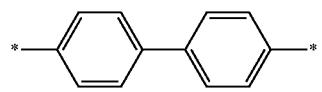

2A

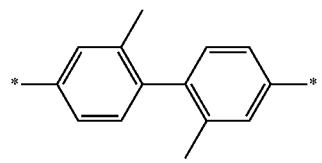

2B

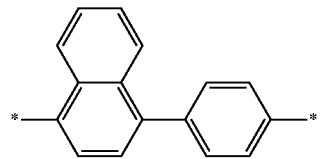

2C

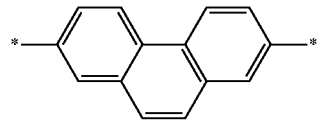

2D

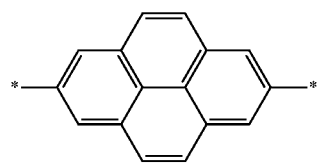

2E

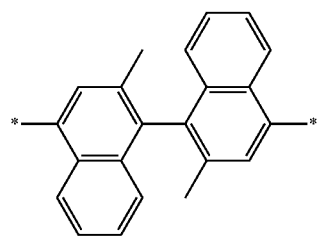

2F

-continued

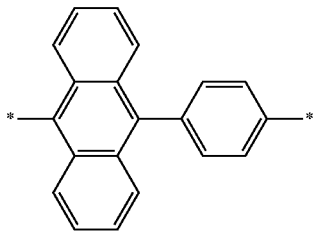

2G

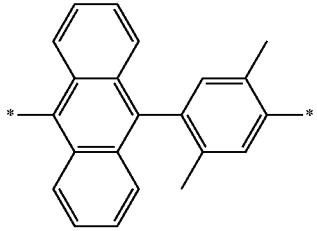

2H

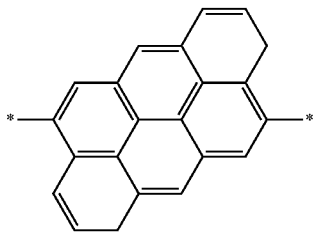

2I

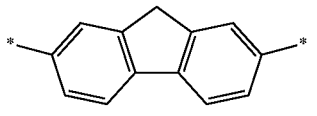

2J

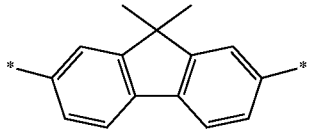

2K

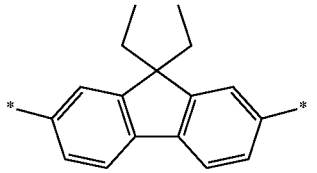

2L

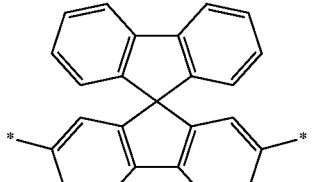

2M

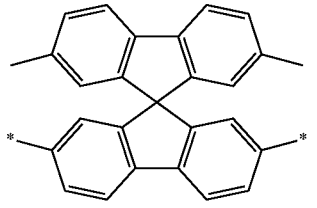

2N

-continued
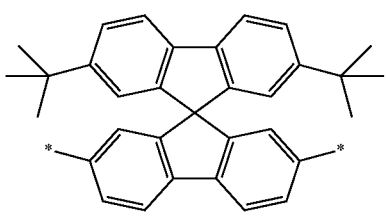
2O
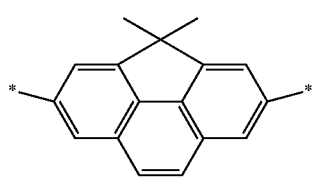
2Y
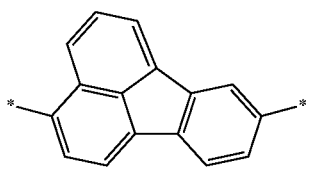
2P
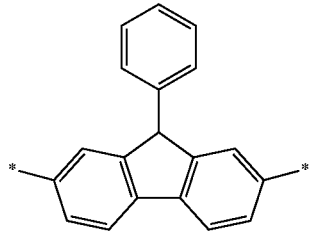
2Z
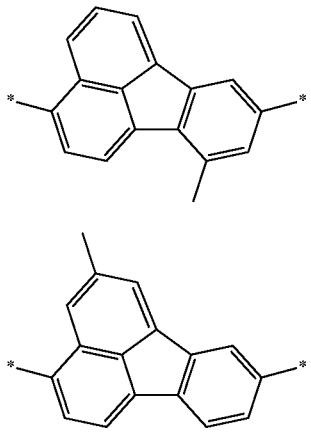
2Q
2R
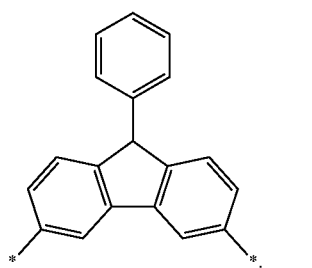
2AA
In one embodiment, B and C parts represented by dotted line boxes in Formula 1 may be each independently selected from Formulae 3A to 3F:
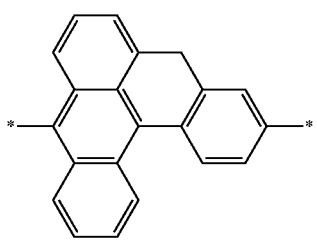
2V
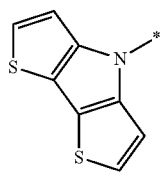
3A
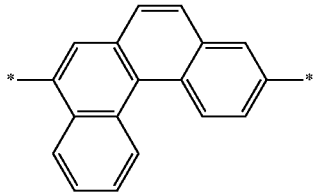
2W
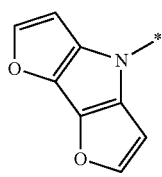
3B
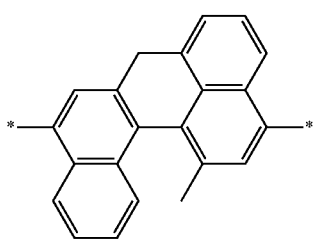
2X
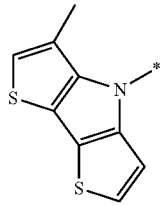
3C -continued 3D
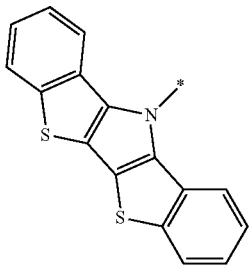

3E
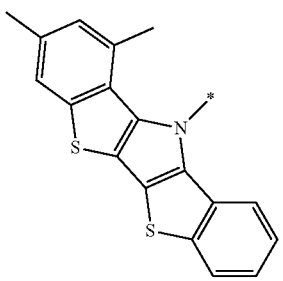

3F
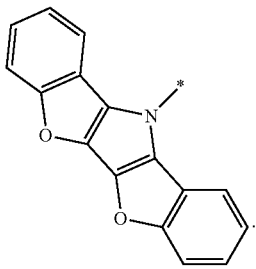

According to one or more embodiments of the present invention, the condensed cyclic compound represented by Formula 1 may be represented by one of Formula 1-1 and Formula 1-2:

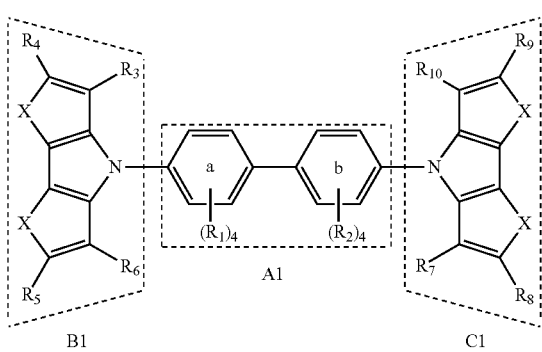

Formula 1-1

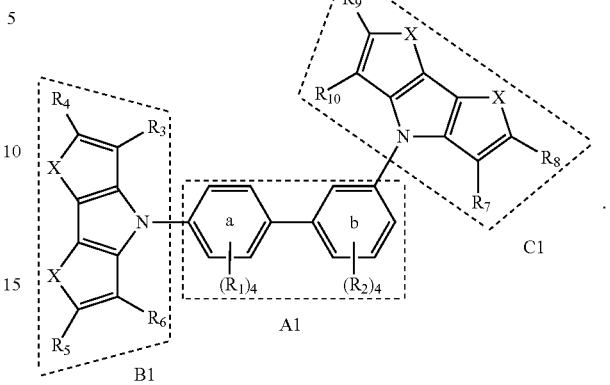

Formula 1-2

In Formula 1-1 and Formula 1-2, X is an oxygen atom or a sulfur atom, and $R_1$ to $R_{10}$ are as described herein.

In one embodiment, the plurality of $R_1$ are each independently selected from a hydrogen and a $C_1$-$C_{10}$ alkyl group.

In another embodiment, at least one of the plurality of $R_1$ is selected from a hydrogen and a $C_1$-$C_{10}$ alkyl group, and two or more of the plurality of $R_1$ (different from the at least one of the plurality of $R_1$) are interlinked with each other to form a substituted or unsubstituted naphthylene group or anthrylene group that is fused together with an 'a' benzene ring, and at least one substituent of the substituted naphthylene group and/or the substituted anthrylene group may be selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

In one embodiment, the plurality of $R_2$ are each independently selected from a hydrogen and a $C_1$-$C_{10}$ alkyl group, In another embodiment, at least one of the plurality of $R_2$ is selected from a hydrogen and a $C_1$-$C_{10}$ alkyl group, and two or more of the plurality of $R_2$ (different from the at least one of the plurality of $R_2$) are linked to each other to form a substituted or unsubstituted naphthylene group or anthrylene group that is fused together with a 'b' benzene ring, and at least one substituent of the substituted naphthylene group and/or the substituted anthrylene group may be selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

In one embodiment, at least one of the plurality of $R_1$ and $R_2$ is selected from a hydrogen and a $C_1$-$C_{10}$ alkyl group, and at least another one $R_1$ of the plurality of $R_1$ and at least another one $R_2$ of the plurality of $R_2$ are linked to each other to form a substituted or unsubstituted $C_{13}$-$C_{30}$ condensed ring that is fused with the 'a' and 'b' benzene rings, where at least one substituent of the substituted $C_{13}$-$C_{30}$ condensed ring may be selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

In one embodiment, an A1 part represented by a dotted line box in Formula 1-1 and Formula 1-2 may be selected from Formulae 2A to 2AA:
2A
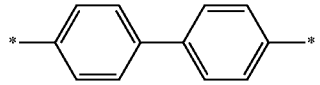
2B
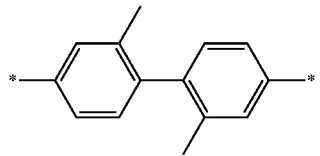
2C
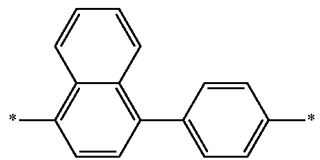
2D
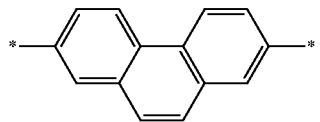
2E
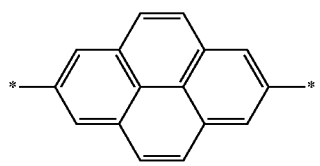
2F
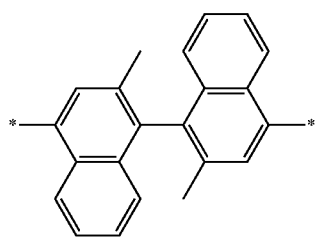
2G
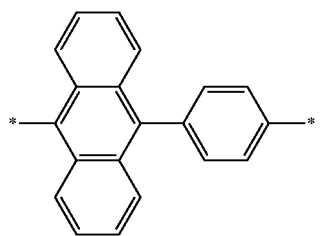
2H
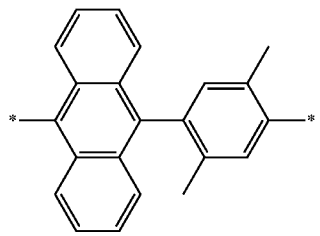
-continued
2I
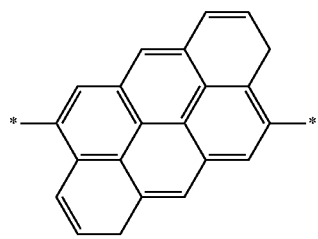
2J
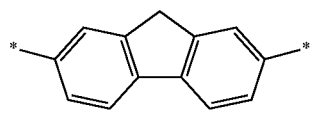
2K
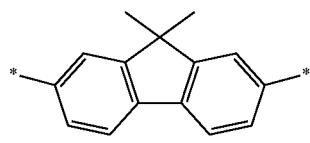
2L
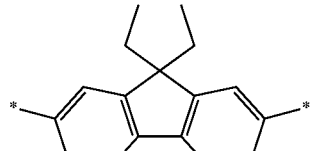
2M
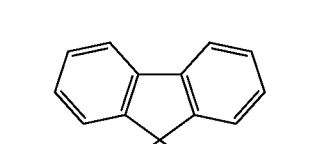
2N
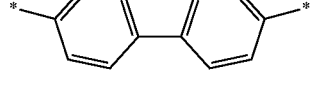
2O
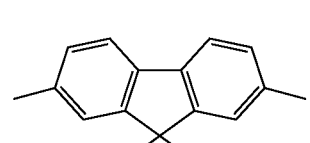
2P
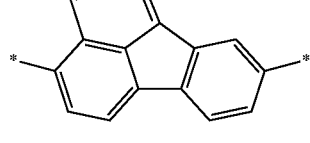

2Q 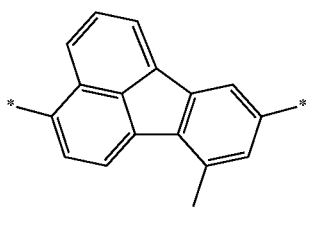
2R 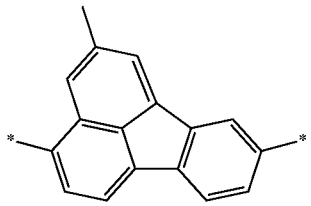
2S 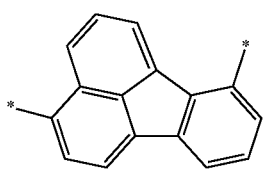
2T 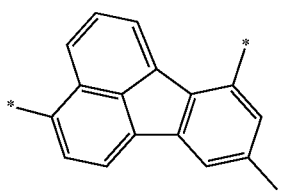
2U 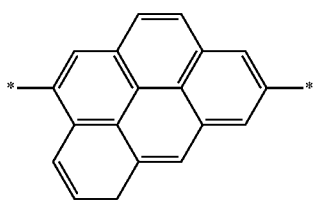
2V 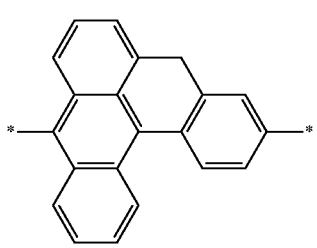
2W 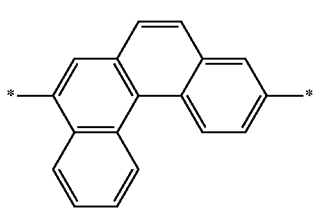
2X 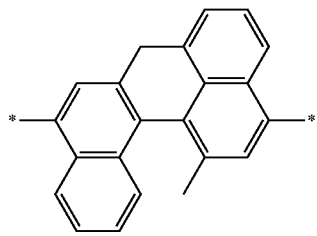
2Y 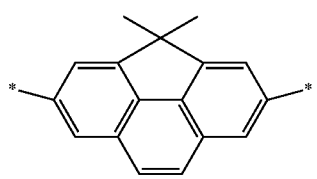
2Z 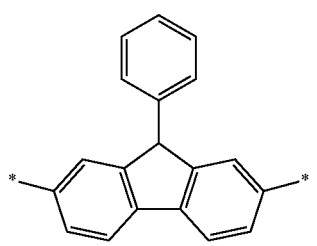
2AA 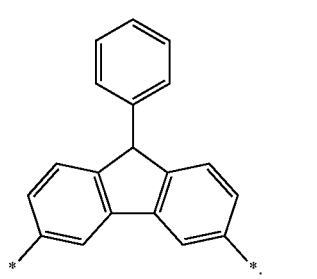
In one embodiment, B1 and C1 parts represented by dotted line boxes in Formula 1-1 and Formula 1-2 may be each independently selected from Formulae 3A to 3F:
3A 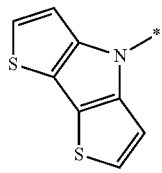
3B 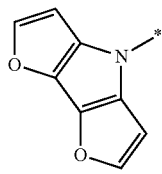

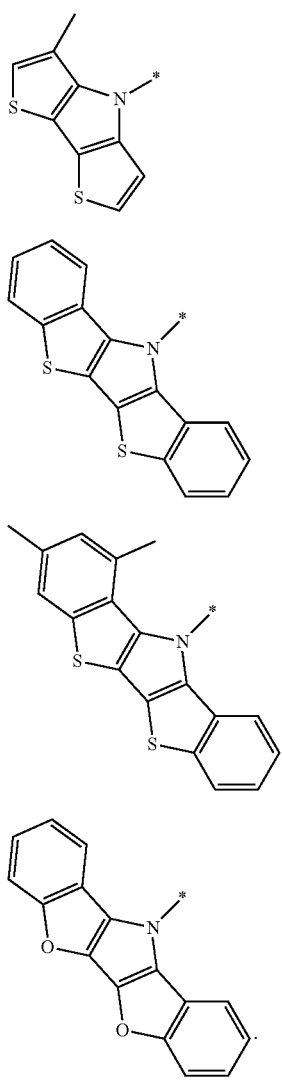
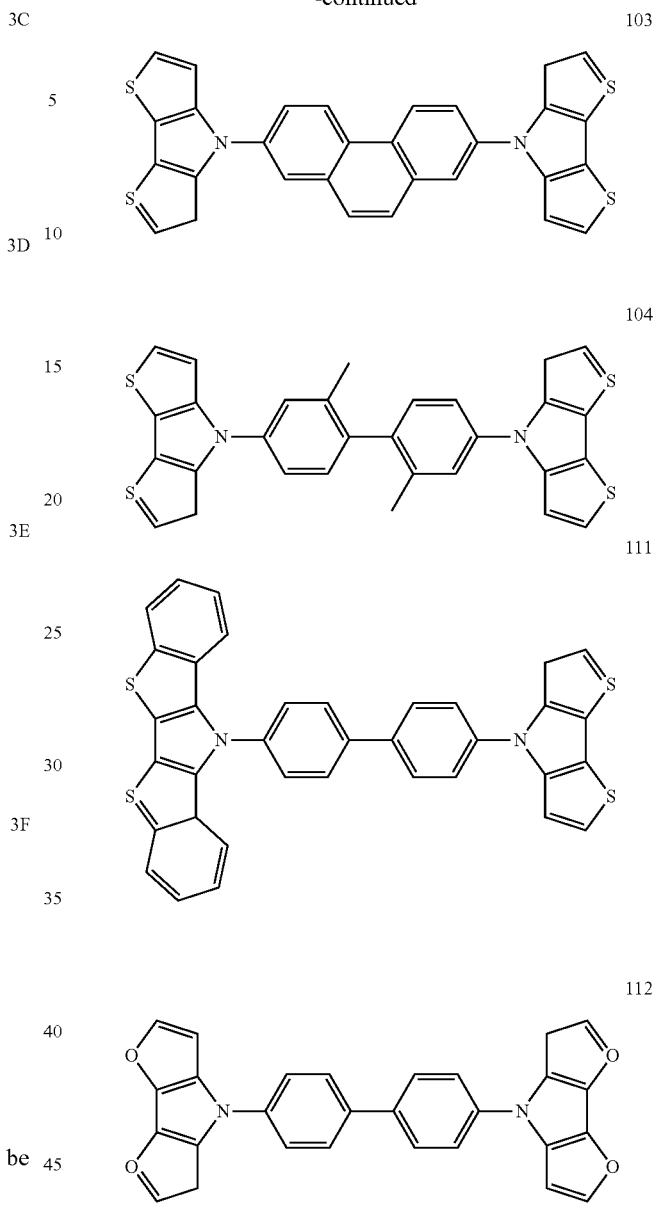
The condensed cyclic compound of Formula 1 may be represented by one of Compounds 101 to 141 below:
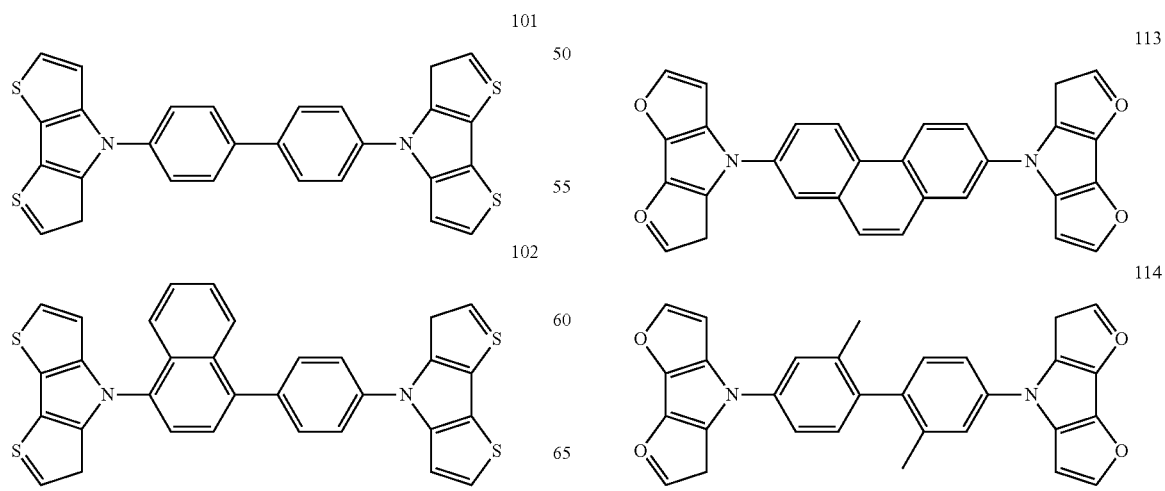

115
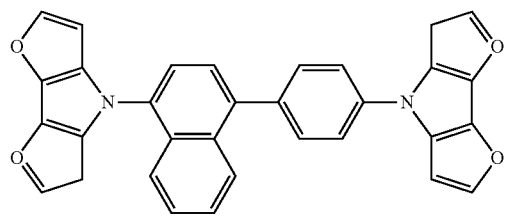
116
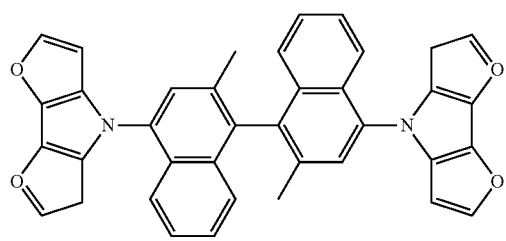
117
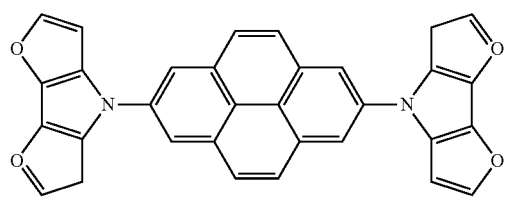
118
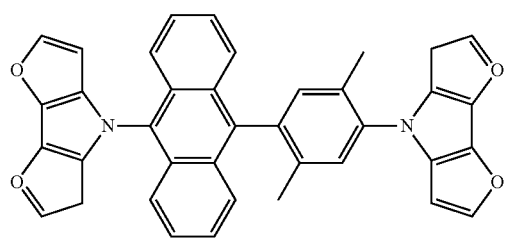
119
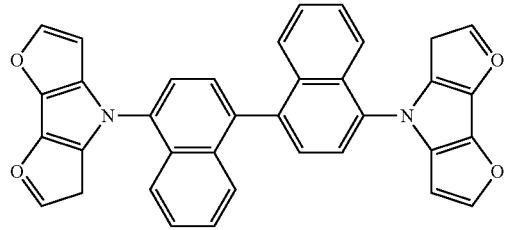
120
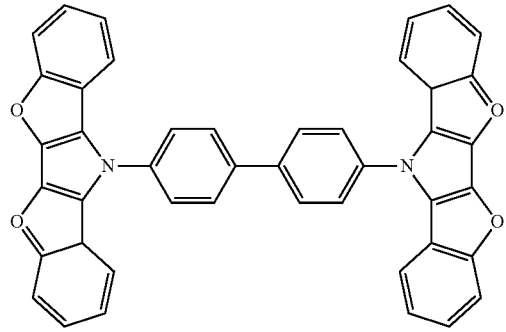
121
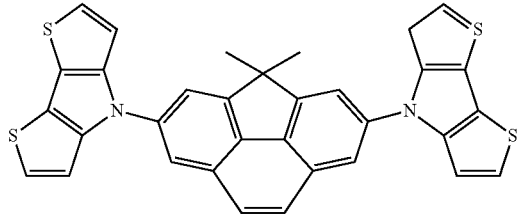
122
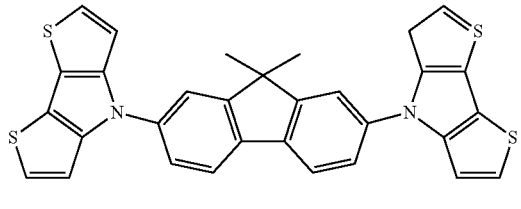
123
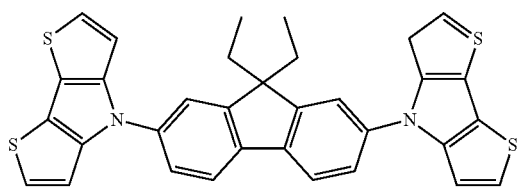
124
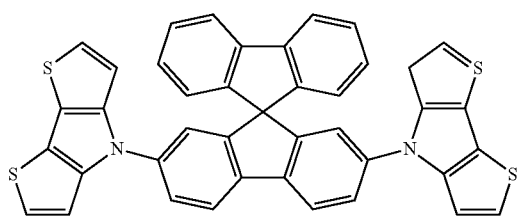
125
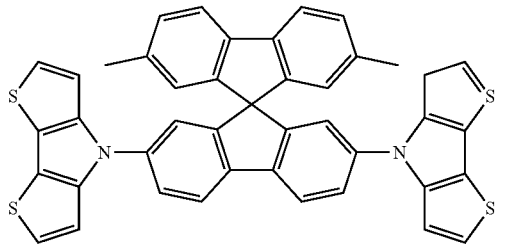
126
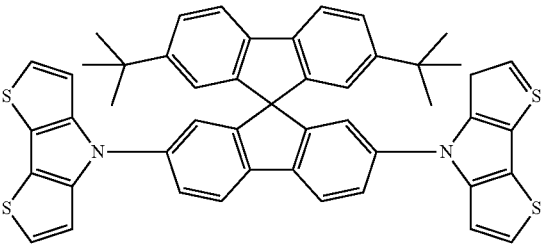

127
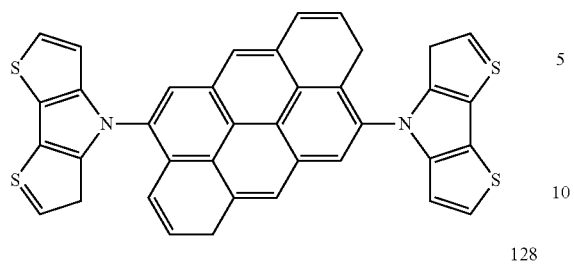
128
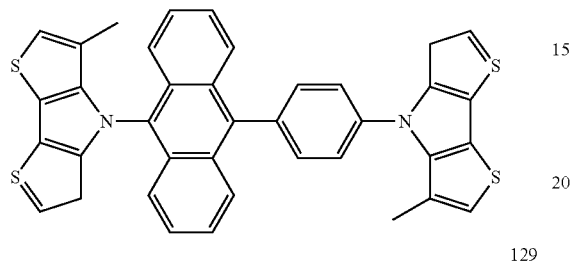
129
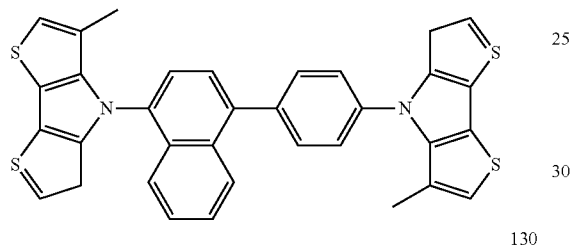
130
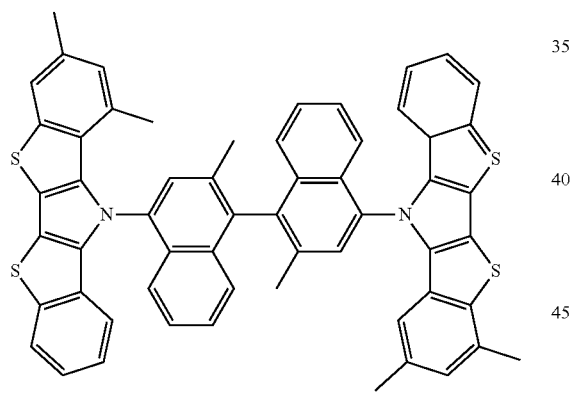
131
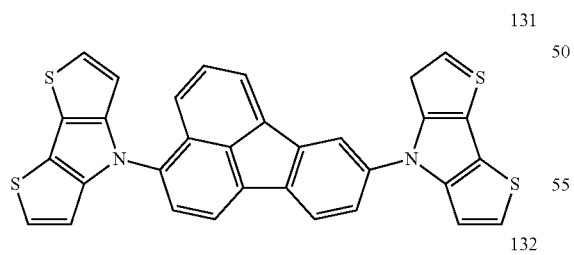
132
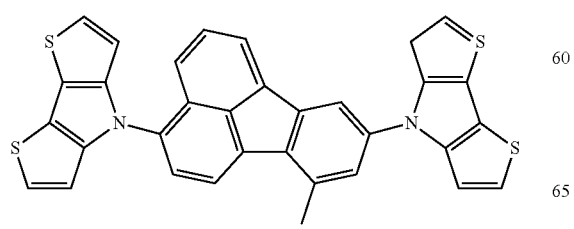
133
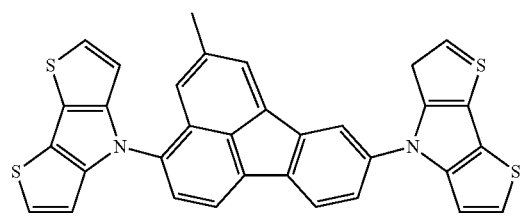
134
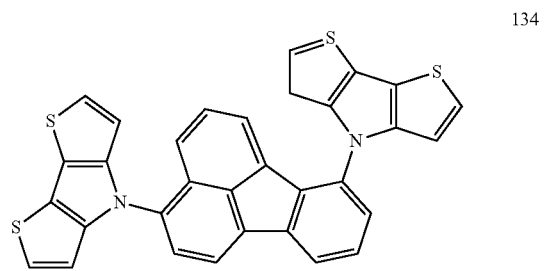
135
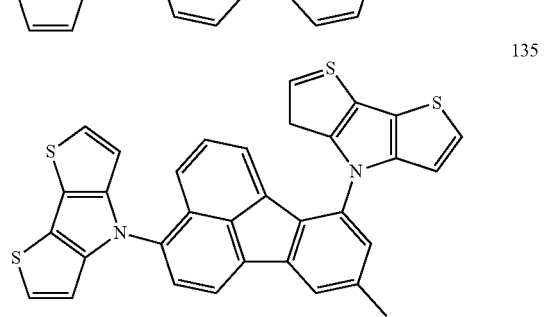
136
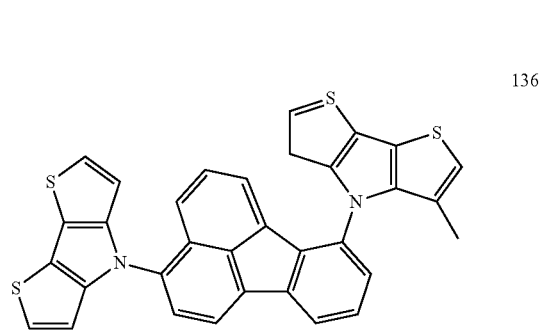
137
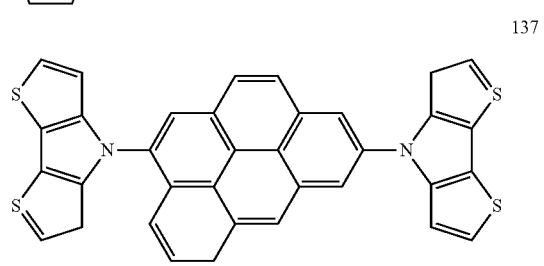
138
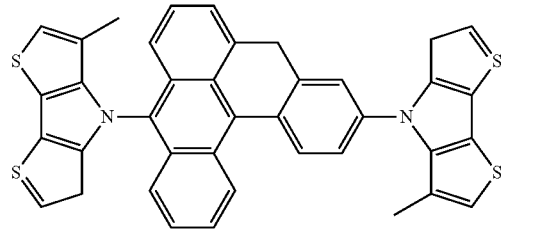

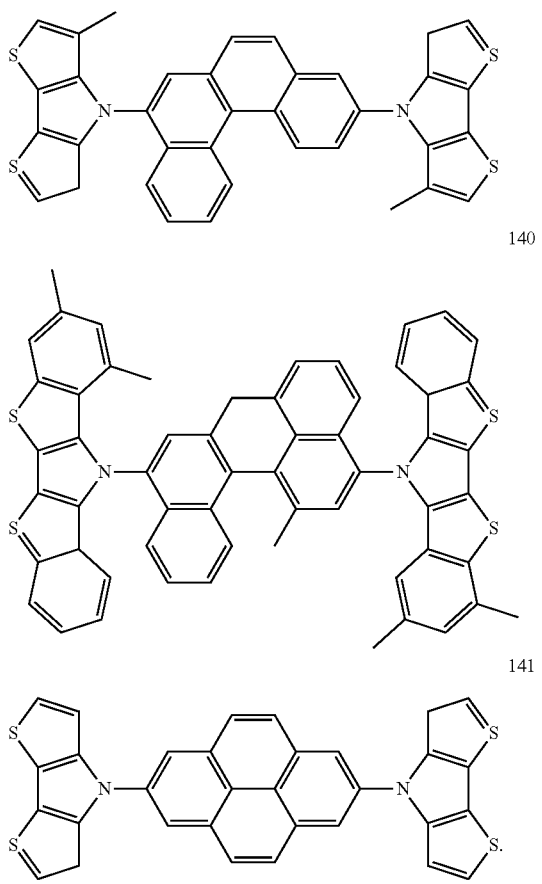

The condensed cyclic compound of Formula 1 may include a carbazole derivative group that further includes a sulfur atom and/or an oxygen atom in the condensed ring and that may improve the hole injection and transport capacity, thereby improving the device performance. In other words, an organic light-emitting device including the condensed cyclic compound represented by Formula 1 may have low driving voltage, high efficiency, high brightness, and long lifespan.

The condensed cyclic compound represented by Formula 1 may be synthesized by any suitable organic synthetic method. A synthesis method of the condensed cyclic compound should become apparent to one of ordinary skill in the art in view of the following examples.

In one embodiment, the condensed cyclic compound of Formula 1 may be positioned between a pair of electrodes of an organic light-emitting device. For example, the condensed cyclic compound may be included a hole transport region (e.g., a hole transport layer). In one embodiment of the present invention, an organic light-emitting device includes a first electrode, a second electrode facing the first electrode, and an organic layer between the first electrode and the second electrode and including at least one condensed cyclic compound represented by Formula 1.

The organic layer may further include a hole transport region between the first electrode and the emission layer, and an electron transport region between the emission layer and the second electrode. The electron transport region may include at least one selected from a hole blocking layer, an electron transport layer, and an electron injection layer. The hole transport region may include at least one selected from an electron blocking layer, a hole transport layer, and a hole injection layer.

The expression "an organic layer includes at least one condensed cyclic compound represented by Formula 1" as used herein may refer to an organic layer including one condensed cyclic compound represented by Formula 1 or an organic layer including two or more different condensed cyclic compounds represented by Formula 1."

In one embodiment, the organic layer may include only one kind of the condensed cyclic compound of Formula 1. The compound may be included in the emission layer, the electron transport layer, and/or the hole transport layer of the organic light-emitting device. In another embodiment, the organic layer may include two different condensed cyclic compounds of Formula 1. The two different condensed cyclic compounds may both be included in the same layer (for example, the two different condensed cyclic compounds may both be included in the emission layer) or in different layers (for example, one of the two different condensed cyclic compounds may be included in the hole transport layer, and the other one may be included in the electron transport layer.)

The emission layer, the hole transport region, and/or the electron transport region may include the condensed cyclic compound represented by Formula 1.

For example, the electron transport region may include the electron transport layer, and the electron transport layer may include the condensed cyclic compound represented by Formula 1.

The term "organic layer" as used herein refers to a single layer and/or a plurality of layers between the first electrode and the second electrode of an organic light-emitting device. A material included in the "organic layer" is not limited to an organic material.

The drawing is a schematic view of an organic light-emitting device 10 according to an embodiment of the present invention. The organic light-emitting device 10 includes a substrate 11, a first electrode 13, an organic layer 15, and a second electrode 17.

Hereinafter, the structure of an organic light-emitting device according to an embodiment of the present invention and a method of manufacturing an organic light-emitting device according to an embodiment of the present invention will be described in connection with the drawing.

The substrate 11 may be a glass substrate or a transparent plastic substrate, each with good mechanical strength, thermal stability, transparency, surface smoothness, ease of handling, and water repellency.

The first electrode 13 may be formed by depositing or sputtering a material for forming the first electrode on the substrate. When the first electrode 13 is an anode, the material for the first electrode 13 may be selected from materials with a high work function, in order for the holes to be easily injected. The first electrode 13 may be a reflective electrode, a transmissive electrode, or a semi-transmissive electrode. A material for the first electrode 13 may be a transparent and highly conductive material, and non-limiting examples of such material include indium tin oxide (ITO), indium zinc oxide (IZO), tin oxide ($SnO_2$), and zinc oxide (ZnO). When the first electrode 13 is a semi-transmissive electrode or a reflective electrode, the material for forming the first electrode 13 may include at least one of magnesium (Mg), aluminum (Al), aluminum-lithium (Al—Li), calcium (Ca), magnesium-indium (Mg—In), and magnesium-silver (Mg—Ag).

The first electrode 13 may have a single-layer structure, or a multi-layer structure including two or more layers. For example, the first electrode 13 may have a three-layered structure of ITO/Ag/ITO, but the structure of the first electrode 13 is not limited thereto.

In one embodiment, the organic layer 15 is positioned on the first electrode 13. The organic layer 15 may include an emission layer.

The organic layer 15 may further include a hole transport region between the first electrode 13 and the emission layer, and an electron transport region disposed between the emission layer and the second electrode 17.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but the layers which may be included in the hole transport region or in the electron transport region are not limited thereto.

The hole transport region may have a single-layered structure formed of a single material, a single-layered structure formed of a plurality of different materials, or a multi-layered structure including a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole injection layer/buffer layer/hole transport layer, a structure of hole transport layer/buffer layer, or a structure of hole injection layer/hole transport layer/electron blocking layer, the layers of each structure being sequentially stacked on the first electrode 13 in the stated order, but the structure of the hole transport region is not limited thereto.

When the hole transport region includes a hole injection layer, the hole injection layer may be formed on the first electrode 13 by various methods, such as, for example, vacuum deposition, spin coating casting, a Langmuir-Blodgett (LB) method, ink-jet printing, laser-printing, or laser-induced thermal imaging.

When the hole injection layer is formed by vacuum deposition, for example, the vacuum deposition may be performed at a deposition temperature of about 100 to about 500° C., a vacuum degree of about $10^{-8}$ to about $10^{-3}$ torr, and a deposition rate of about 0.01 to about 100 Å/sec, depending on the compound for forming the hole injection layer, and the structure of the hole injection layer to be formed.

When the hole injection layer is formed by spin coating, the spin coating may be performed at a coating rate of about 2,000 rpm to about 5,000 rpm, and at a temperature of about 80° C. to 200° C., depending on the compound for forming the hole injection layer, and the structure of the hole injection layer to be formed.

When the hole transport region includes a hole transport layer, the hole transport layer may be formed on the first electrode 13 or on the hole injection layer by various methods, such as, for example, vacuum deposition, spin coating, casting, a LB method, ink-jet printing, laser-printing, or laser-induced thermal imaging. When the hole transport layer is formed by vacuum deposition or spin coating, deposition and coating conditions for the hole transport layer may be similar to the deposition and coating conditions for the hole injection layer.

The hole transport region may include at least one selected from the condensed cyclic compound represented by Formula 1, m-MTDATA, TDATA, 2-TNATA, NPB, β-NPB, TPD, spiro-TPD, spiro-NPB, methylated-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (PANI/PSS), a compound represented by Formula 201, and a compound represented by Formula 202:

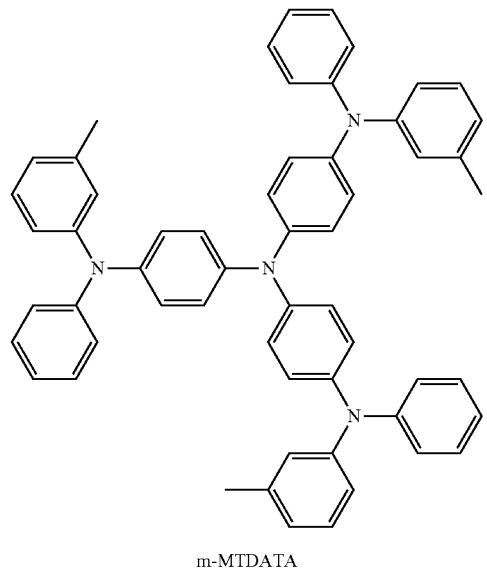

m-MTDATA

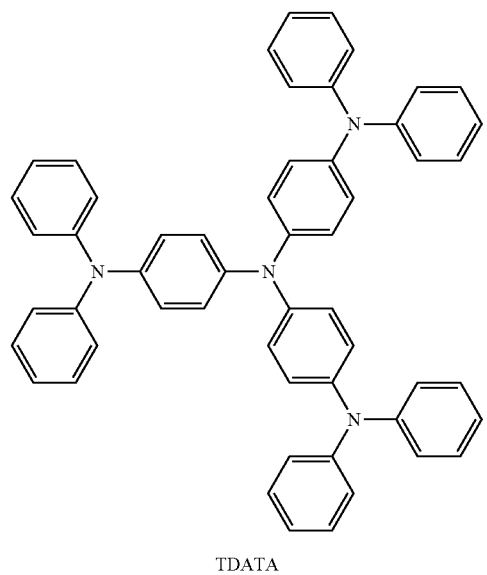

TDATA

-continued
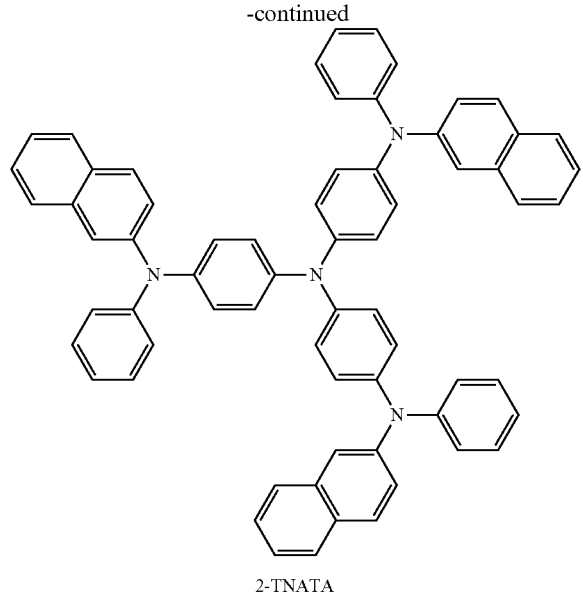
2-TNATA
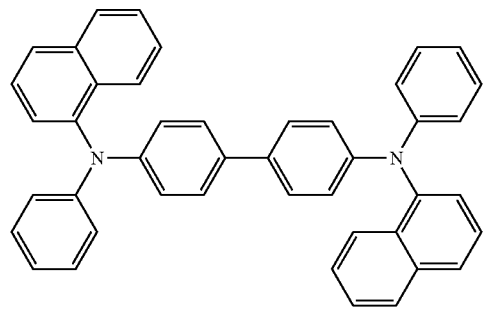
NPB
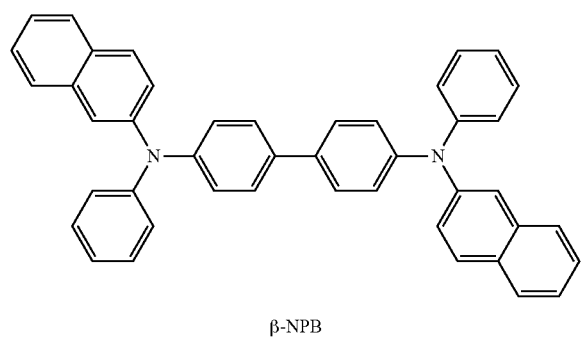
β-NPB
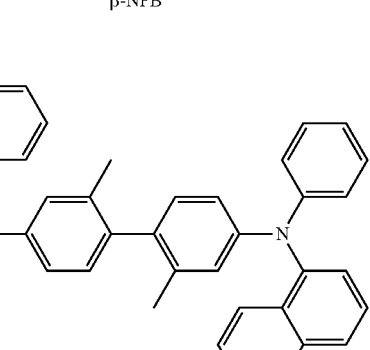
methylated-NPD
-continued
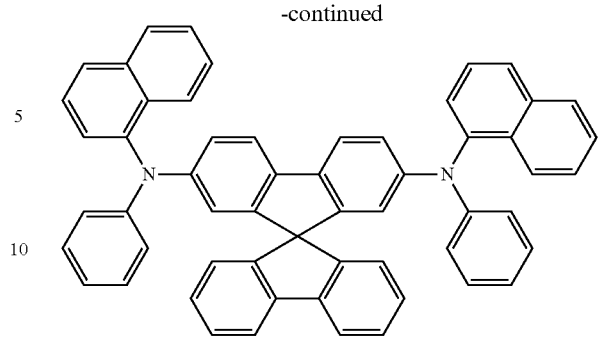
spiro-NPB
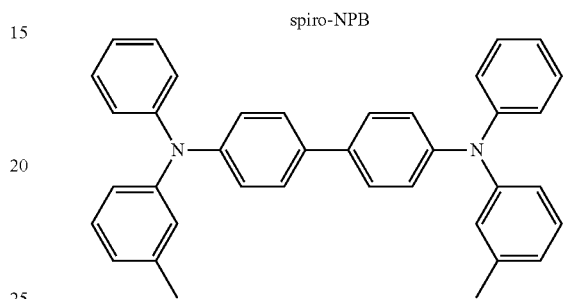
TPD
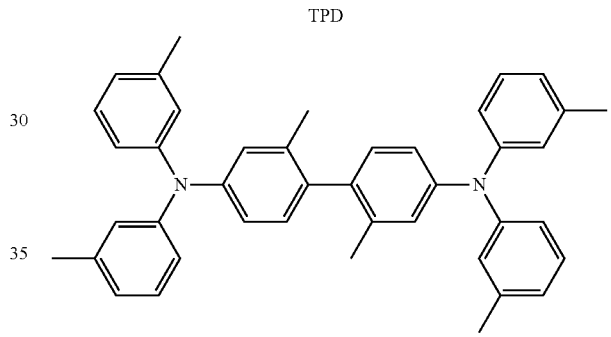
HMTPD
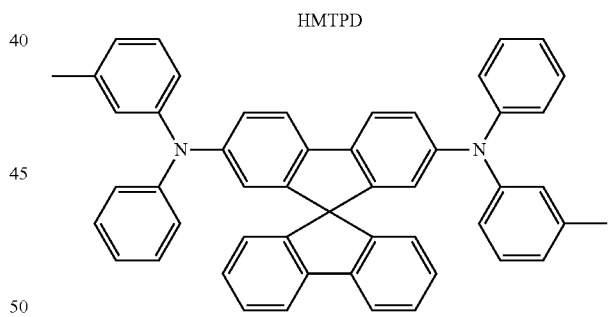
spiro-TPD
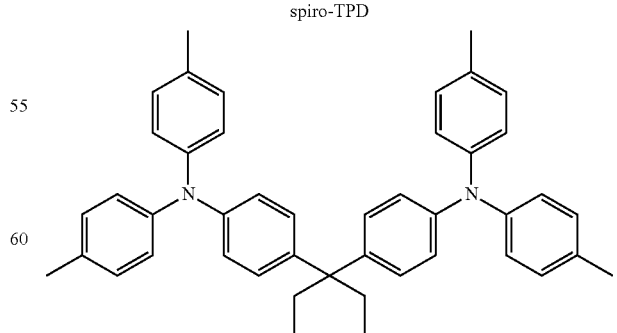
TAPC

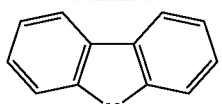

TCTA

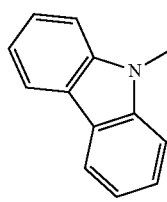

PEDOT/PSS

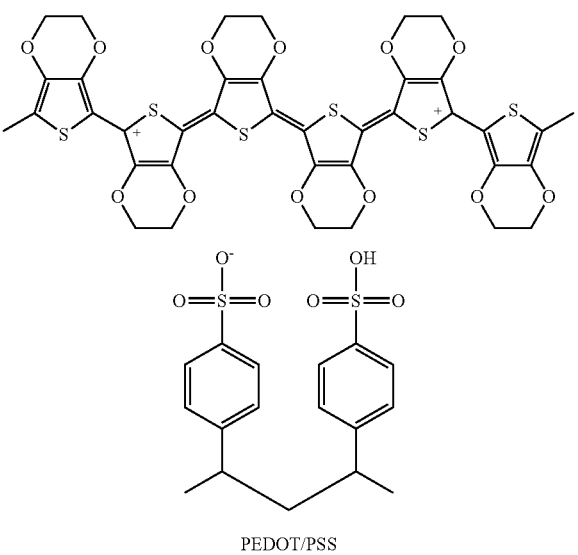

PANI/DBSA

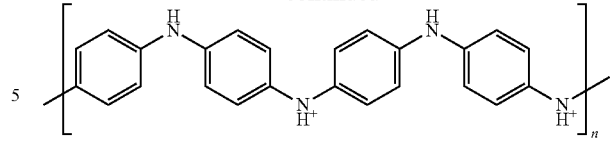

PANI/CSA

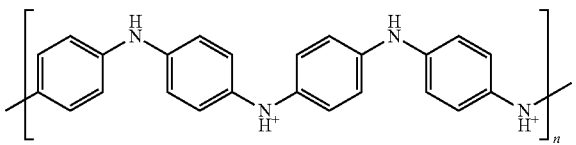

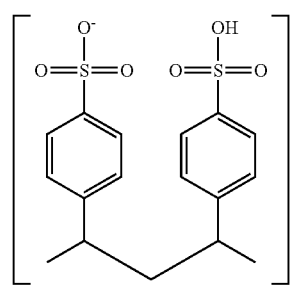

PANI/PSS

Formula 201

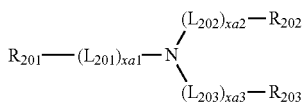

Formula 202

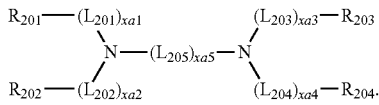

In Formulae 201 and 202, $L_{201}$ to $L_{205}$ may be each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_1$-$C_{60}$ heteroarylene group (e.g. a substituted or unsubstituted $C_2$-$C_{60}$ heteroarylene group), and a substituted or unsubstituted divalent $C_6$-$C_{60}$ non-aromatic condensed polycyclic group;

xa1 to xa4 may be each independently selected from 0, 1, 2, and 3;

xa5 may be selected from 1, 2, 3, 4, and 5; and $R_{201}$ to $R_{204}$ may be each independently selected from a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, and a substituted or unsubstituted monovalent $C_6$-$C_{30}$ non-aromatic condensed polycyclic group.

In one embodiment, $L_{201}$ to $L_{205}$ in Formulae 201 and 202 may be each independently selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present invention are not limited thereto.

In one embodiment, the compound represented by Formula 201 may be represented by Formula 201A:

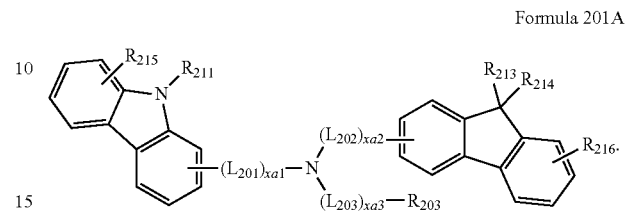

Formula 201A

For example, the compound represented by Formula 201 may be represented by Formula 201A-1, but is not limited thereto:

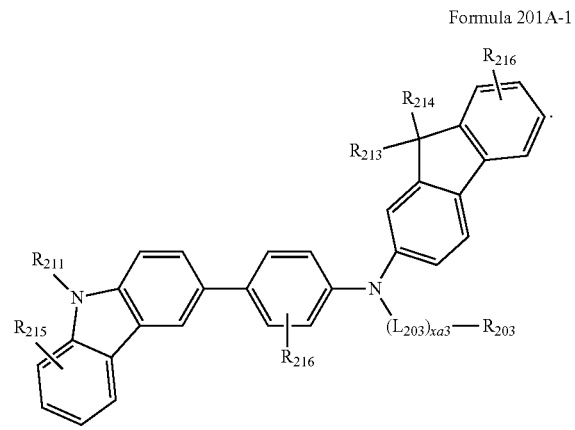

Formula 201A-1

In one embodiment, the compound represented by Formula 202 may be represented by Formula 202A, but is not limited thereto:

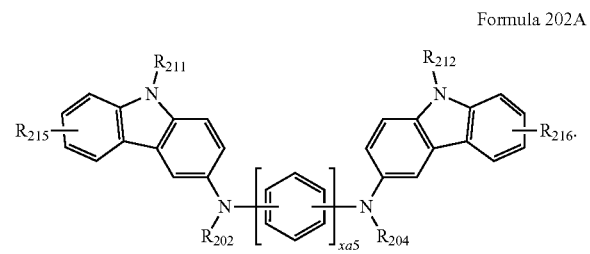

Formula 202A $L_{201}$ to $L_{203}$, xa1 to xa3, xa5, and $R_{202}$ to $R_{204}$ in Formulae 201A, 201A-1, and 202A may be as described above, $R_{211}$ may be described as $R_{203}$, and $R_{213}$ to $R_{216}$ may be each independently selected from a hydrogen, a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a $C_6$-$C_{60}$ non-aromatic condensed polycyclic group.

In one embodiment, in Formulae 201A, 201A-1, and 202A, $L_{201}$ to $L_{203}$ may be each independently selected from a phenylene group, naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group and a triazinylene group; and a phenylene group, naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group and a triazinylene group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from a hydrogen, a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a, pyridazinyl group, a quinolinyl group, an isoquinolinyl group, a quinoxalinyl group, a quinazolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group; and xa5 is 1 or 2.

$R_{213}$ and $R_{214}$ in Formulae 201A, and 201A-1 may bind to each other to form a saturated or unsaturated ring.

The compound represented by Formula 201, and the compound represented by Formula 202 may each include compounds HT1 to HT20 illustrated below, but are not limited thereto.

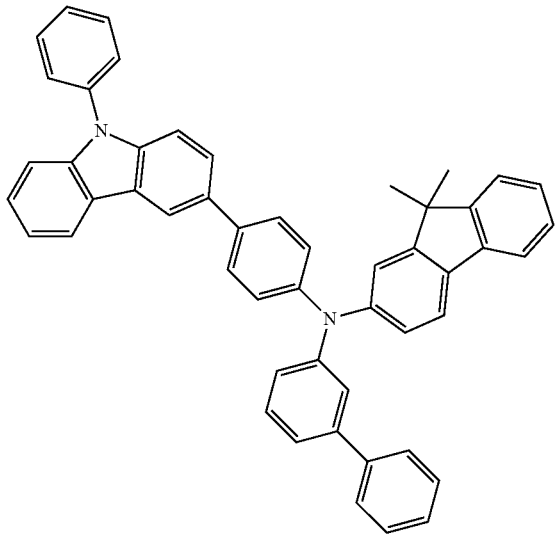

HT2

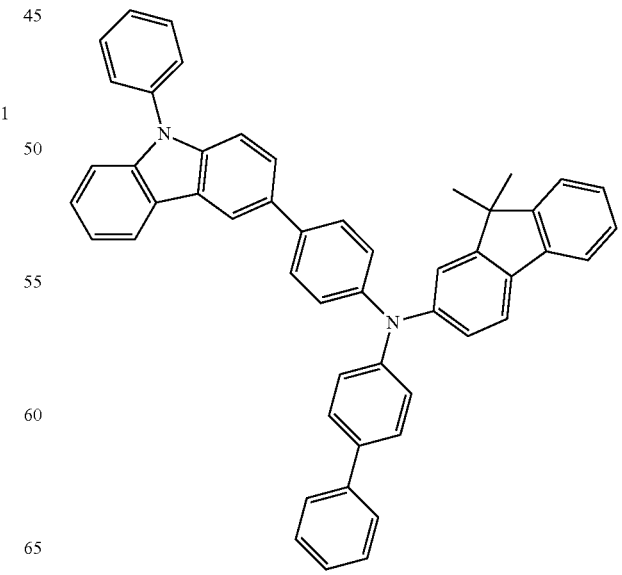

HT3

HT1

HT4
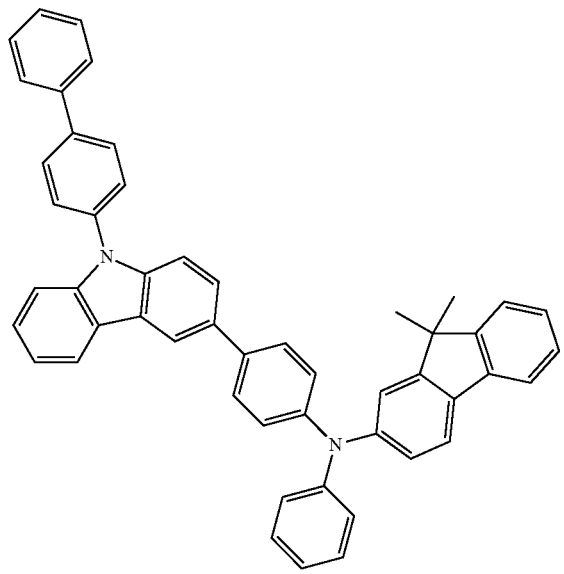
HT5
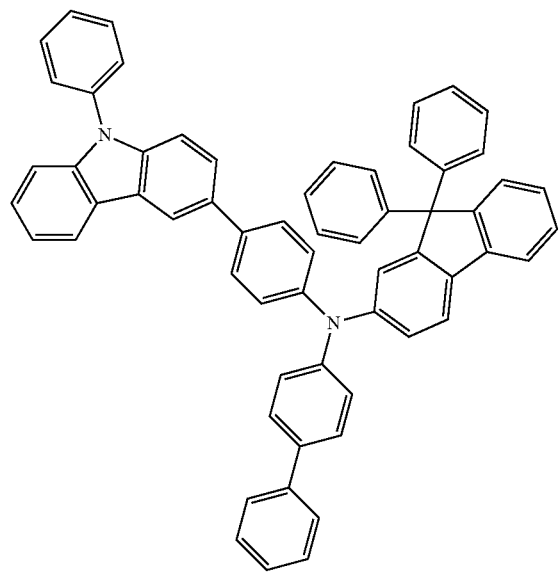
HT6
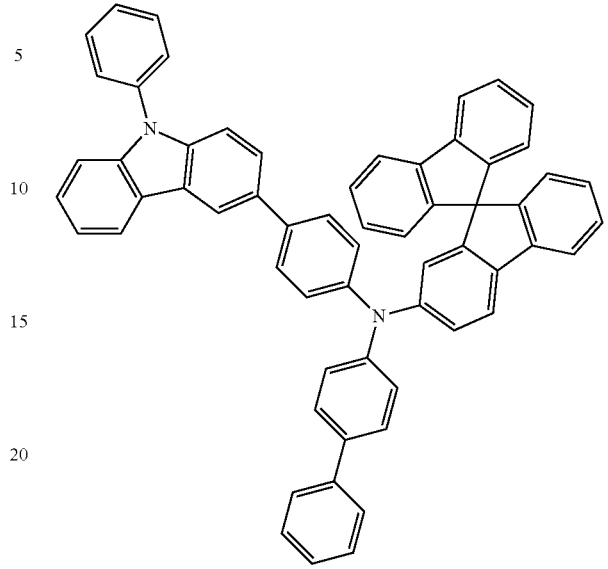
HT7
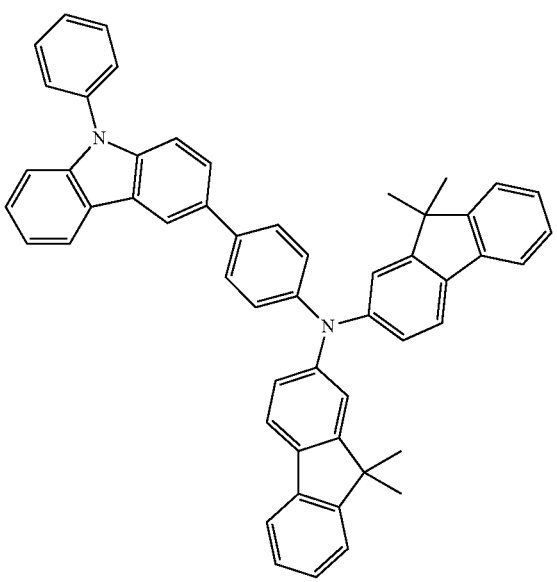

HT8
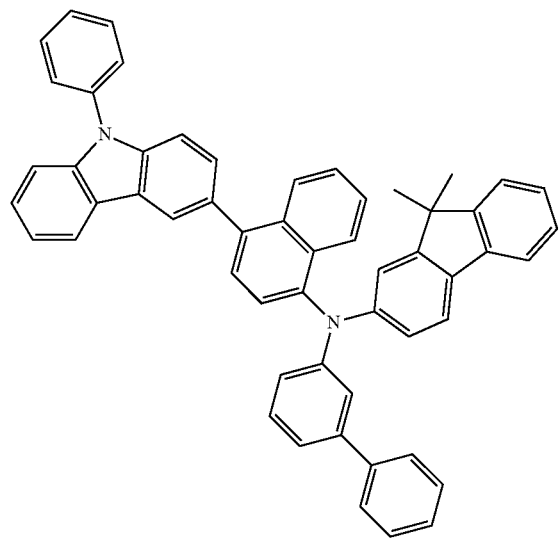
HT11
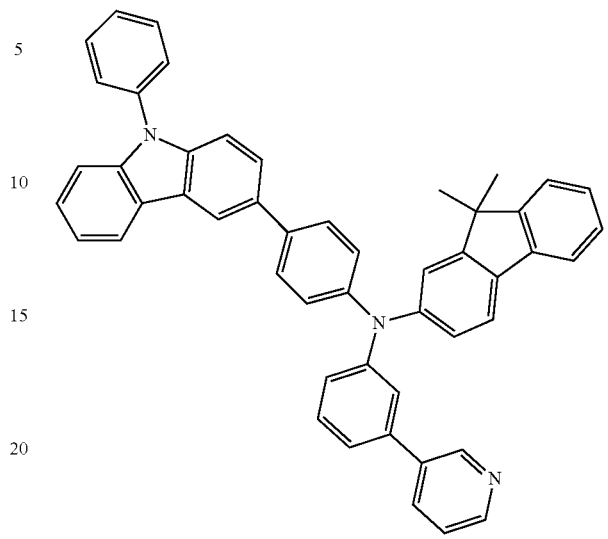
HT9
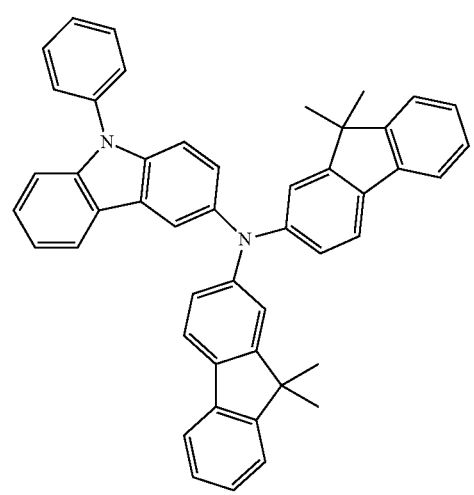
HT12
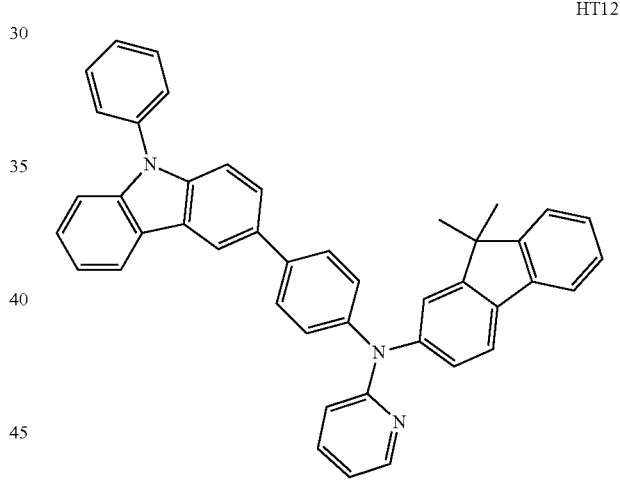
HT10
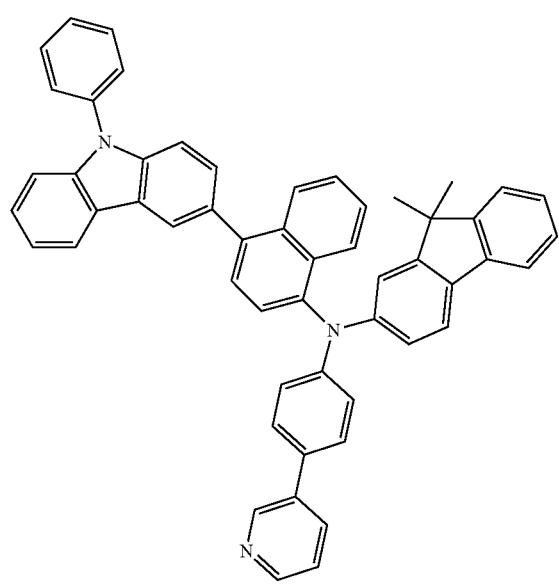
HT13
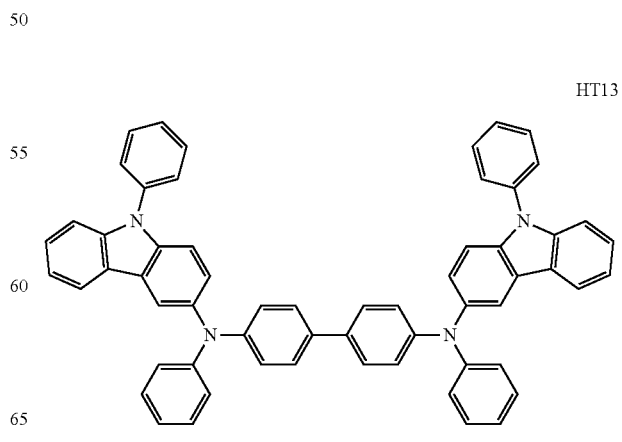

-continued

HT14
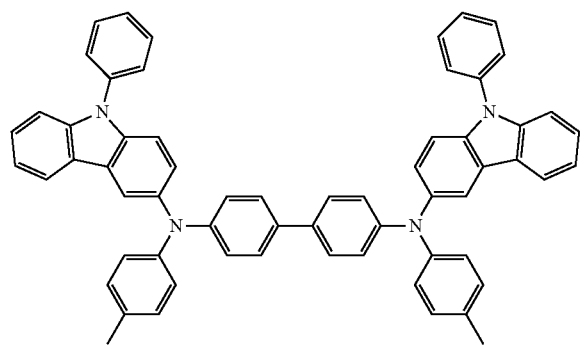

HT15
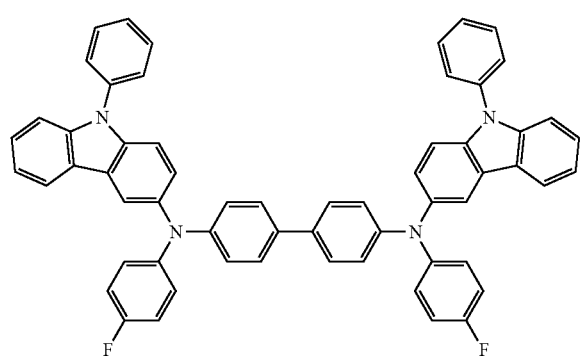

HT16
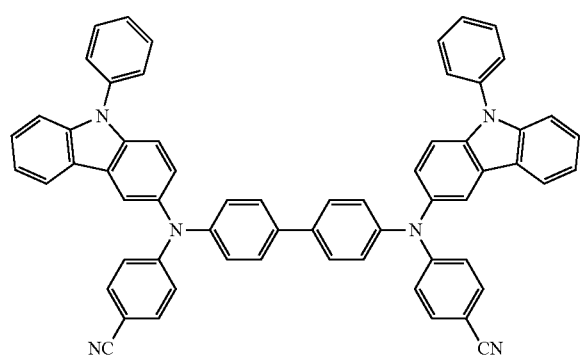

HT17
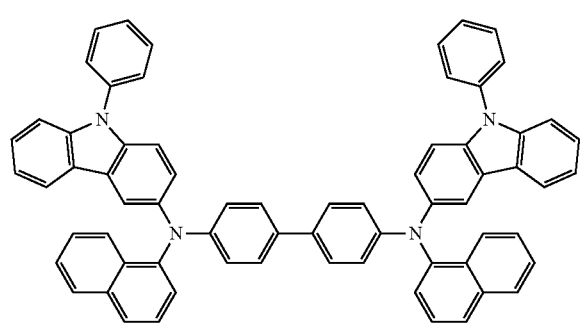

-continued

HT18
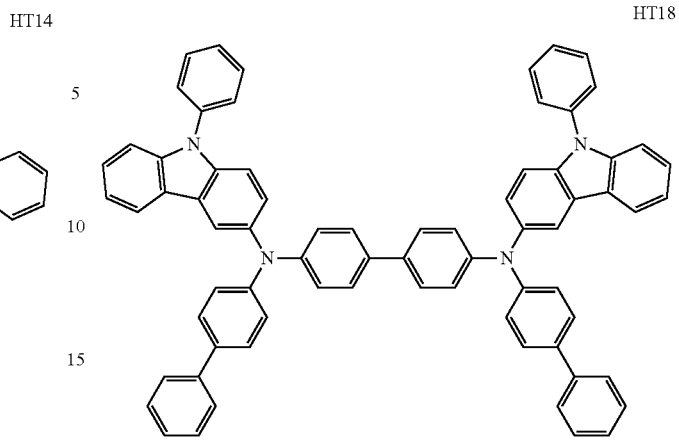

HT19
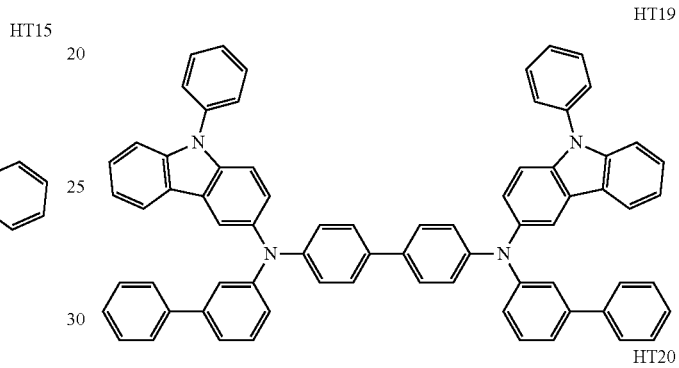

HT20
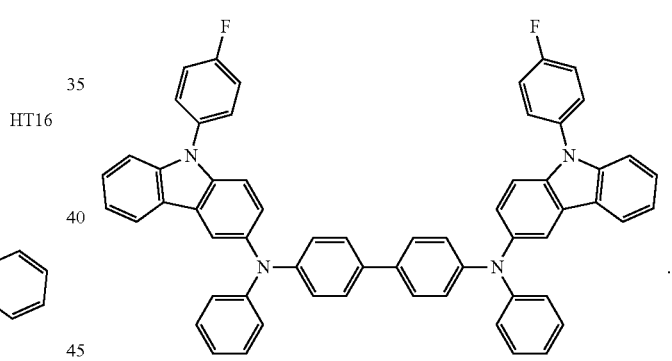

The thickness of the hole transport region may be from about 100 Å to about 10,000 Å, for example, from about 100 Å to about 1,000 Å. When the hole transport region includes both the hole injection layer and the hole transport layer, the thickness of the hole injection layer may be from about 100 Å to about 10,000 Å (e.g. 9,950 Å), for example, from about 100 Å to about 1,000 Å, and the thickness of the hole transport layer may be from about 50 Å to about 2,000 Å, for example, from about 100 Å to about 1,500 Å. When the thicknesses of the hole transport region, the hole injection layer, and the hole transport layer are within any of these ranges, satisfactory hole transporting characteristics may be obtained without a substantial increase in driving voltage.

The hole transport region may further include a charge generation material to improve electric conductivity, in addition to the materials described above. The charge generation material may be dispersed in the hole transport region homogeneously or heterogeneously.

The charge generation material may be, for example, a p-dopant. The p-dopant may be one selected from a quinone derivative, a metal oxide, and a cyano group-containing compound, but is not limited thereto. Non-limiting examples of the p-dopant include a quinone derivative such as tetracyanoquinodimethane (TCNQ) and tetrafluorotetracyanoquinodimethane (F4-TCNQ); a metal oxide such as a tungsten oxide and a molybdenum oxide; and 1,4,5,8,9,11-hexaazatriphenylene-hexacarbonitrile (HATCN):

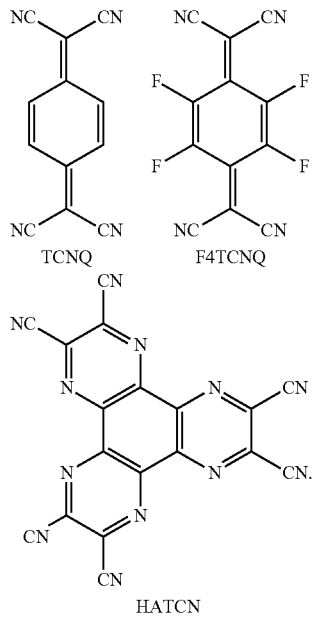

The hole transport region may further include at least one selected from a buffer layer and an electron blocking layer, in addition to the hole injection layer and hole transport layer. Since the buffer layer may compensate for an optical resonance distance according to a wavelength of light emitted from the emission layer, light-emission efficiency of the resulting organic light-emitting device may be improved. Materials that are included in the hole transport region may be utilized as a material for the buffer layer. In one embodiment, the electron blocking layer prevents (or reduces) the injection of electrons from the electron transport region.

An emission layer may be formed on the first electrode 13 or on the hole transport region by various methods, such as, for example, vacuum deposition, spin coating, casting, a LB method, ink-jet printing, laser-printing, or laser-induced thermal imaging. When the emission layer is formed by vacuum deposition or spin coating, deposition and coating conditions for the emission layer may be similar to the deposition and coating conditions for the hole injection layer.

When the organic light-emitting device 10 is a full color organic light-emitting device, the emission layer may be patterned into a red emission layer, a green emission layer, or a blue emission layer, to correspond to individual sub pixels, respectively. In some embodiments of the present invention, the emission layer may emit white light and may have a stacked structure in which the red emission layer, the green emission layer, and the blue emission layer are stacked upon one another, or a structure in which a red-light emission material, a green-light emission material, and a blue-light emission material are mixed with each other in a single layer.

The emission layer may include a host and a dopant.

The host may include at least one selected from TPBi, TBADN, ADN, CBP, CDBP, and TCP:

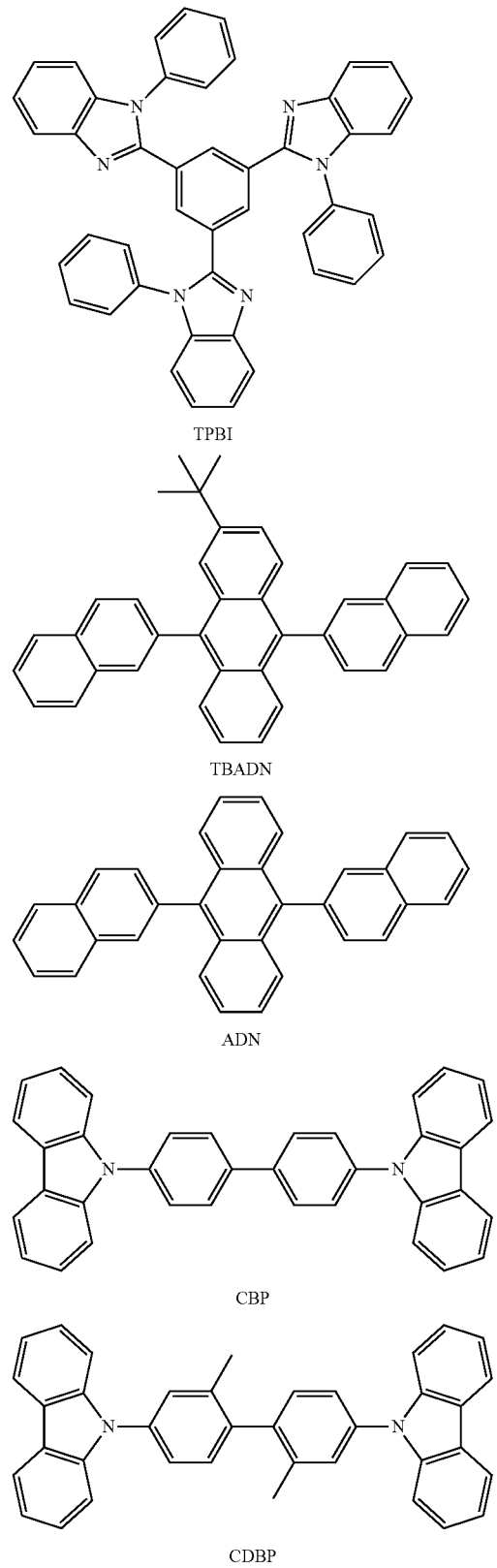

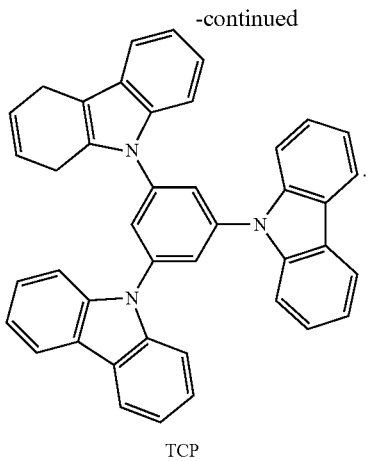

TCP

According to another embodiment of the present invention, the host may include a compound represented by Formula 301.

$$Ar_{301}\text{-}[(L_{301})_{xb1}\text{-}R_{301}]_{xb2}.$$  Formula 301

$Ar_{301}$ in Formula 301 may be selected from naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene, and indenoanthracene;

naphthalene, heptalene, fluorene, spiro-fluorene, benzofluorene, dibenzofluorene, phenalene, phenanthrene, anthracene, fluoranthene, triphenylene, pyrene, chrysene, naphthacene, picene, perylene, pentaphene, and indenoanthracene, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ a heteroaryl group, a monovalent $C_2$-$C_{60}$ non-aromatic condensed polycyclic group, and —Si($Q_{301}$)($Q_{302}$)($Q_{303}$) (where $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

$L_{301}$ may be described as $L_{201}$;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4.

In one embodiment, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but $R_{301}$ is not limited thereto.

In one embodiment, the host may include a compound represented by Formula 301A:

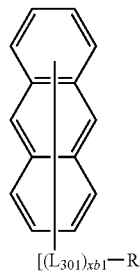

Formula 301A $[(L_{301})_{xb1}-R_{301}]_{Xb2}$.

Substituents of Formula 301A may be as described above and herein.

The compound represented by Formula 301 may include at least one of Compounds H1 to H42, but is not limited thereto:

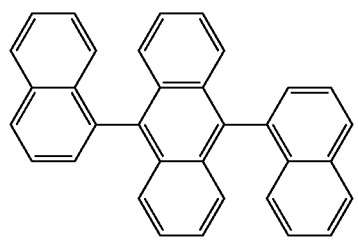

H1

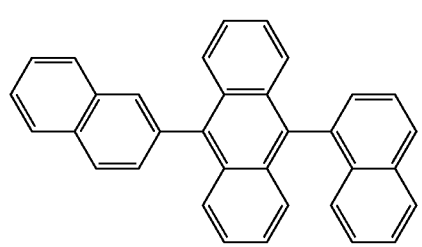

H2

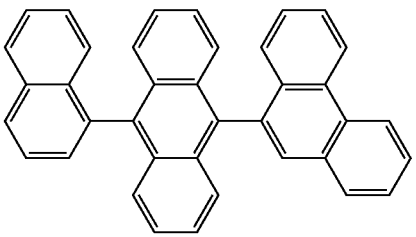

H3

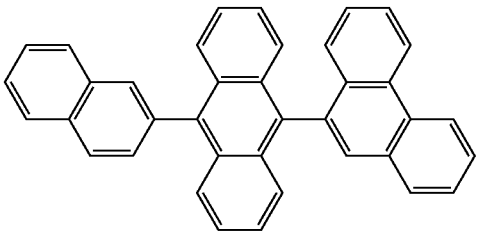

H4

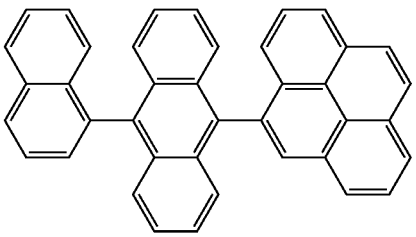

H5

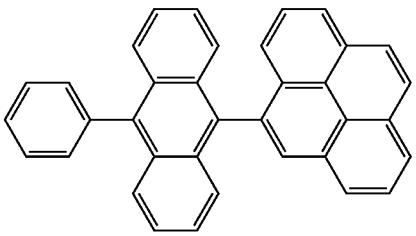

H6

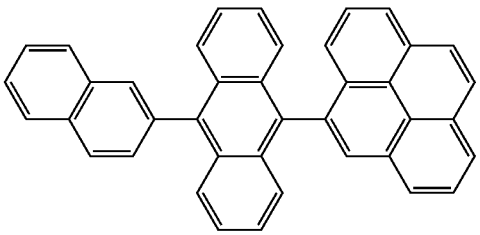

H7

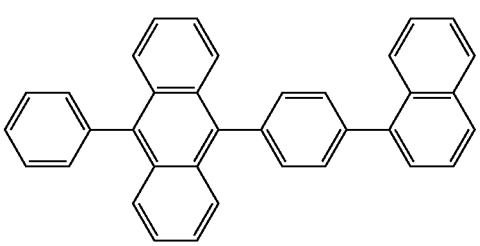

H8

H9
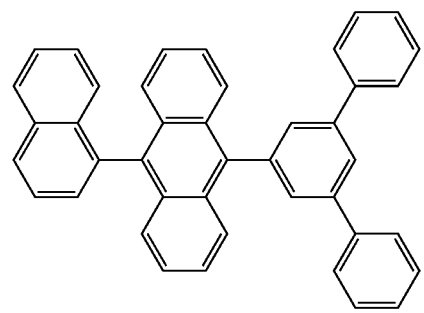
H10
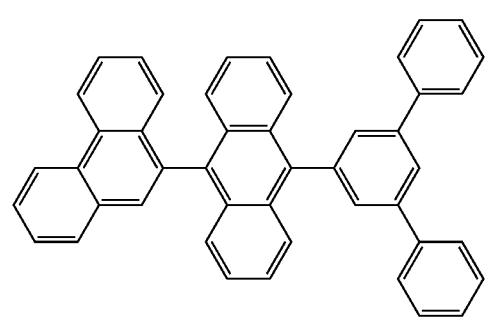
H11
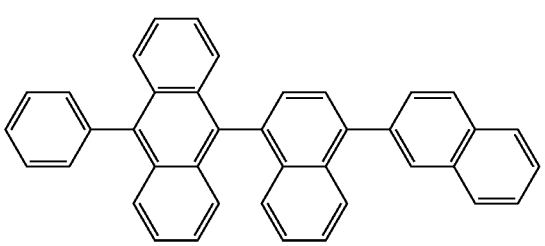
H12
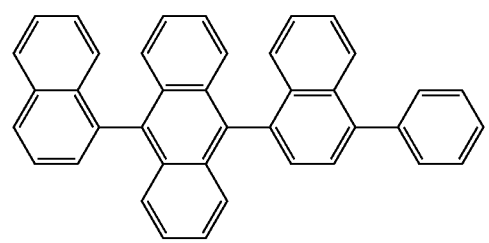
H13
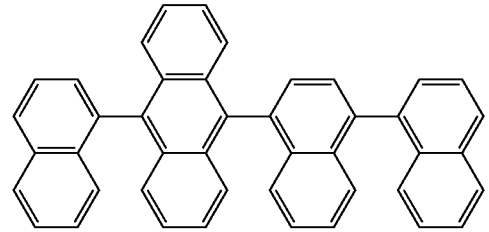
H14
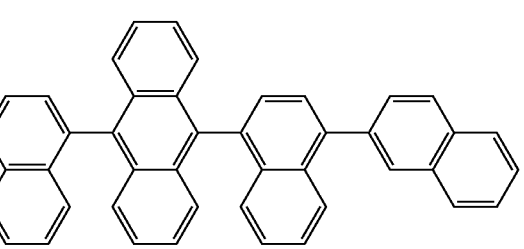
H15
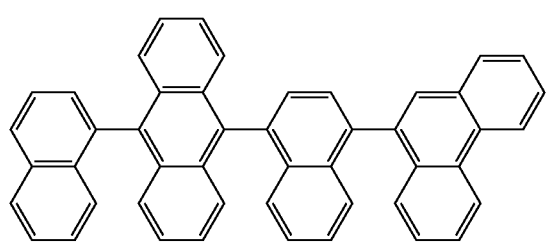
H16
H17
H18
H19
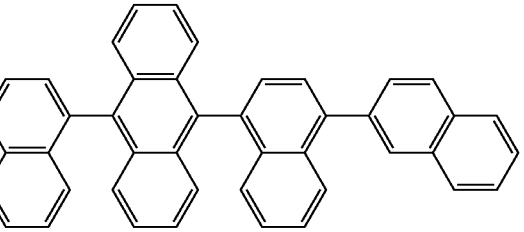

H20
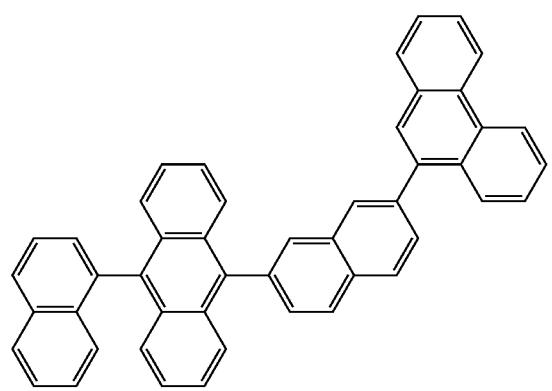
H21
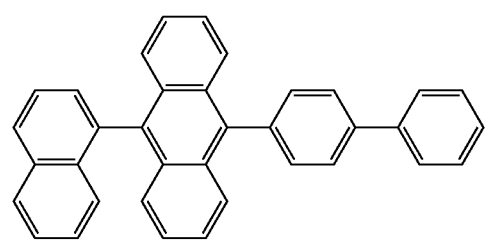
H22
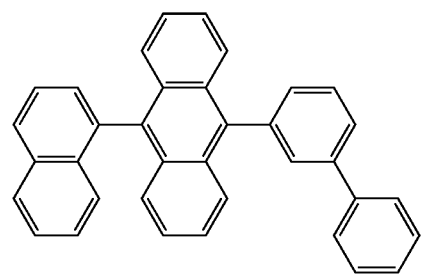
H23
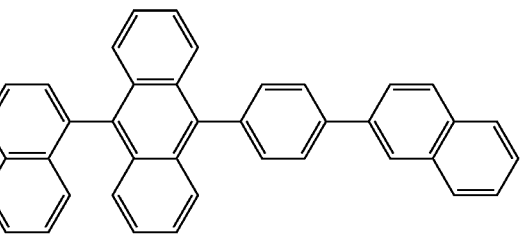
H24
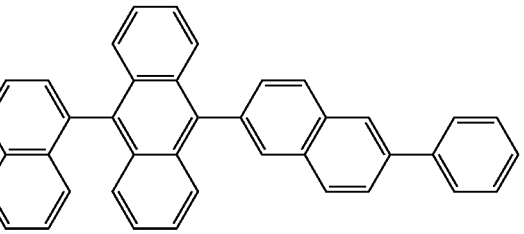
H25
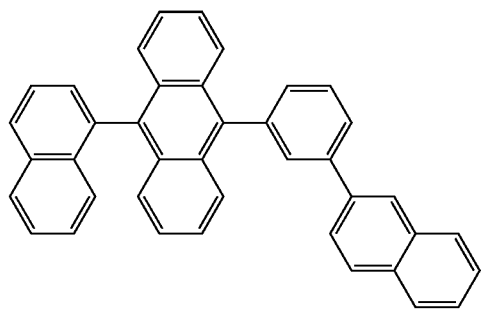
H26
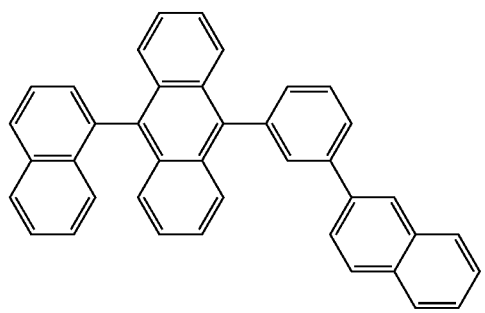
H27
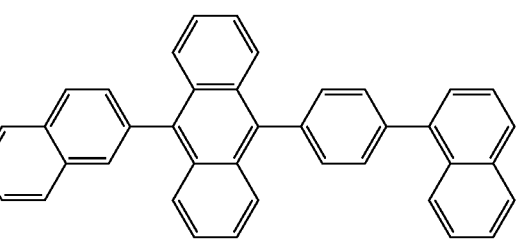
H28
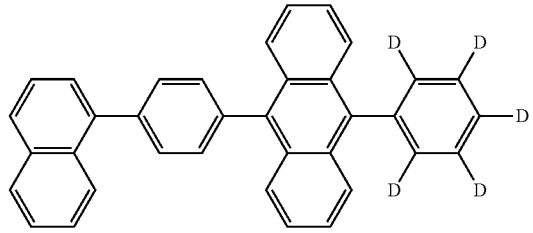
H29
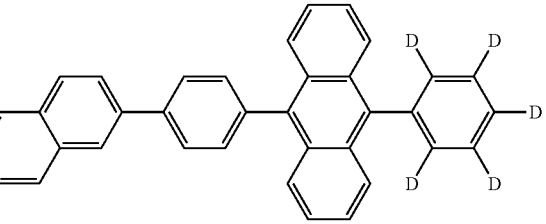
H30
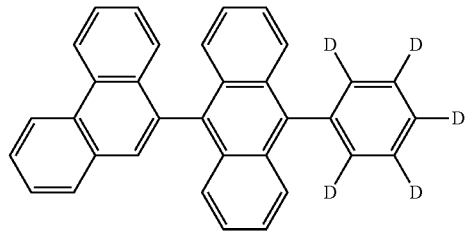

-continued
H31
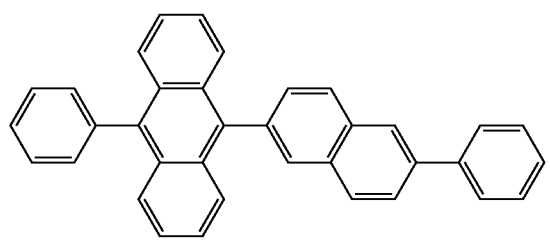
H32
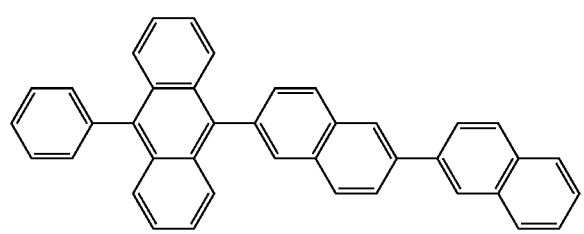
H33
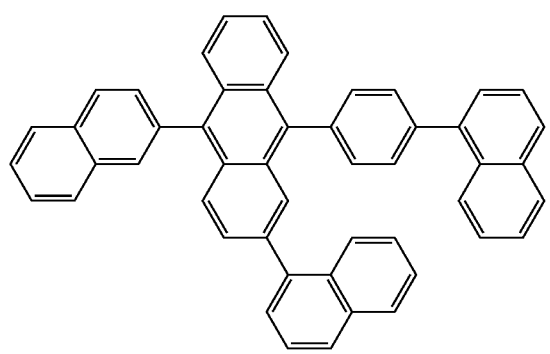
H34
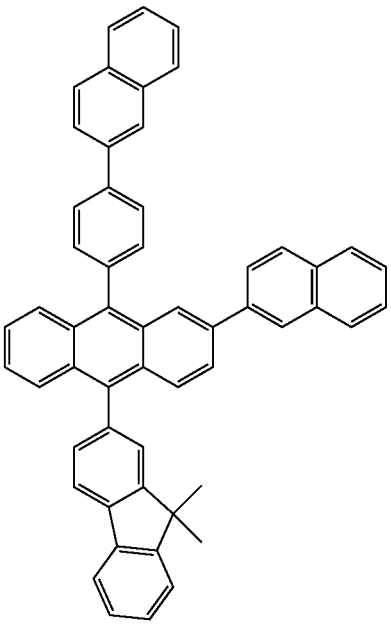
-continued
H35
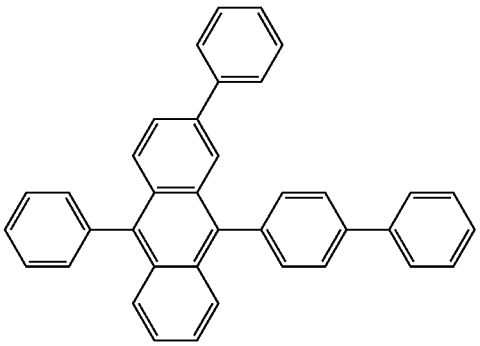
H36
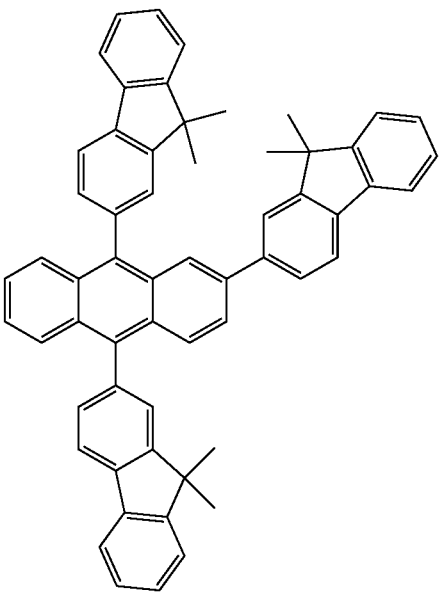
H37

H38
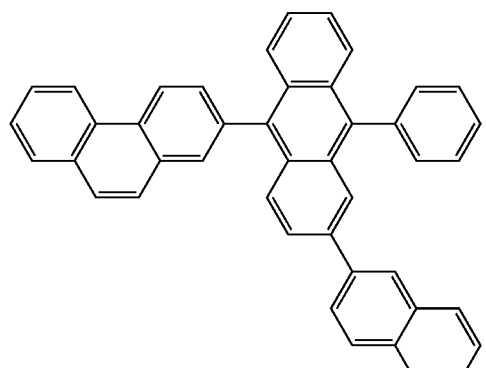
H41
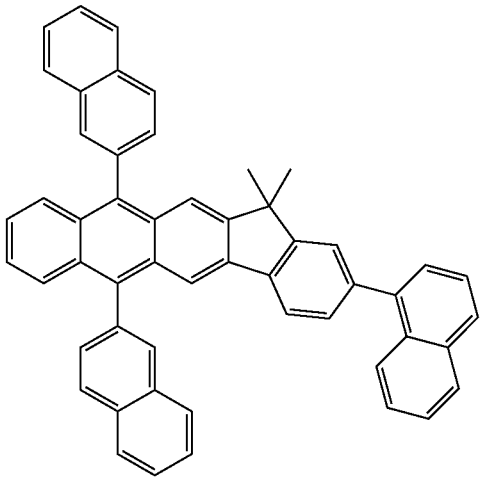
H39
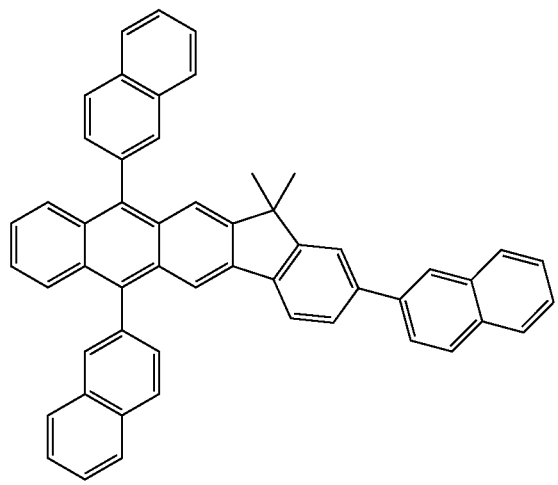
H42
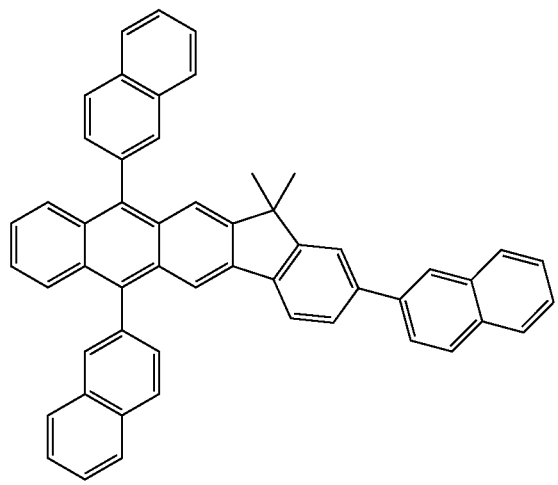
H40
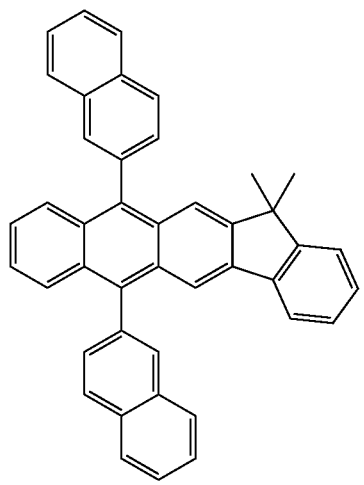
According to another embodiment of the present invention, the host may include at least one of Compounds H43 to H49, but is not limited thereto:
H43
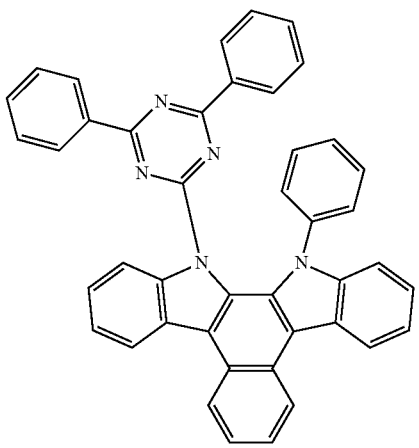

H44

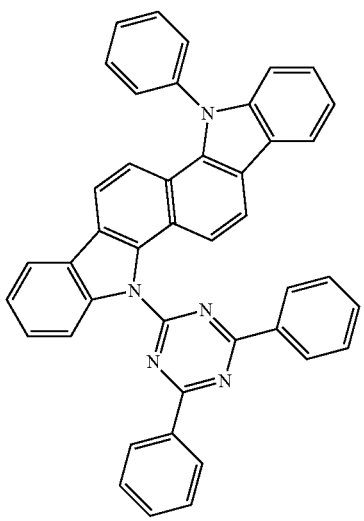

H45

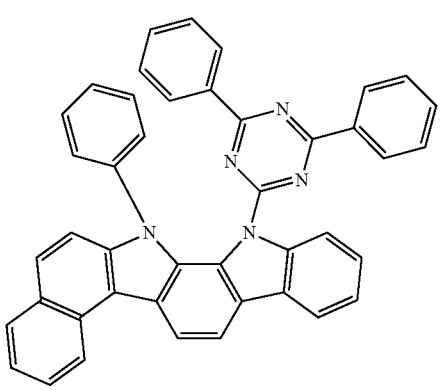

H46

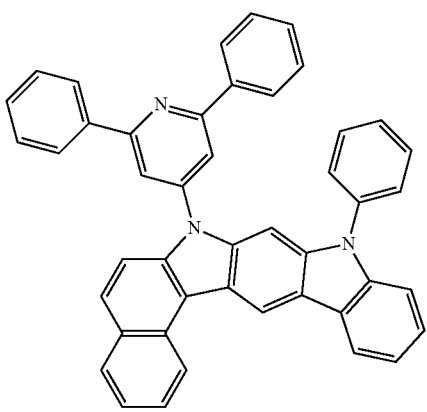

H47

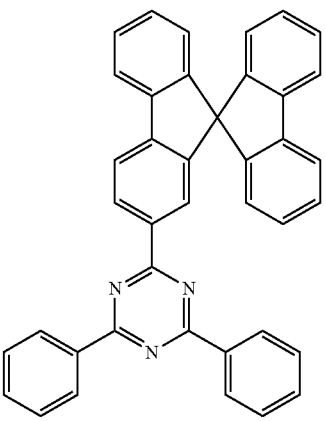

H48

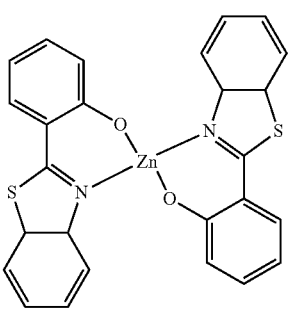

H49

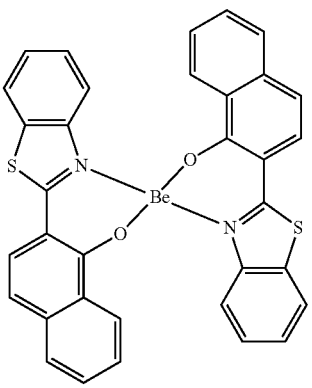

As a dopant, any suitable dopant may be utilized and may include at least one of a fluorescent dopant and a phosphorescent dopant. The phosphorescent dopant may be an organic metallic complex including one or a combination of at least two of Ir, Pt, Os, Re, Ti, Zr, and Hf, but is not limited thereto.

Non-limiting examples of a blue dopant include bis[3,5-difluoro-2-(2-pyridyl)phenyl](picolinato)iridium(III) (F2Irpic), (F$_2$ppy)$_2$Ir(tmd), Ir(dfppz)$_3$, 4,4'-bis(2,2'-diphenylethen-1-yl)biphenyl (DPVBi), 4,4'-bis[4-(diphenylamino)styryl]biphenyl (DPAVBi), and 2,5,8,11-tetra-tert-butyl perylene (TBPe), which are illustrated below:

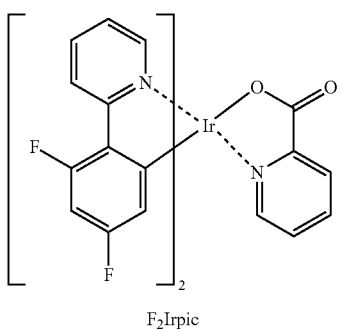
F₂Irpic
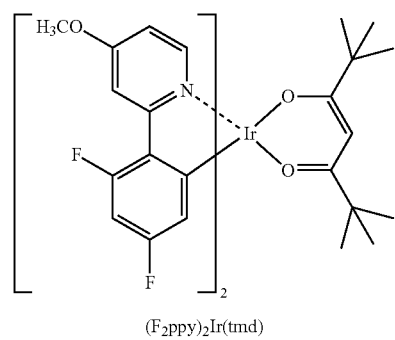
(F₂ppy)₂Ir(tmd)
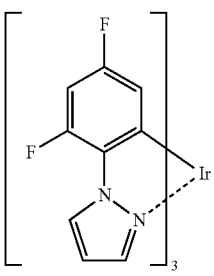
Ir(dfppz)₃
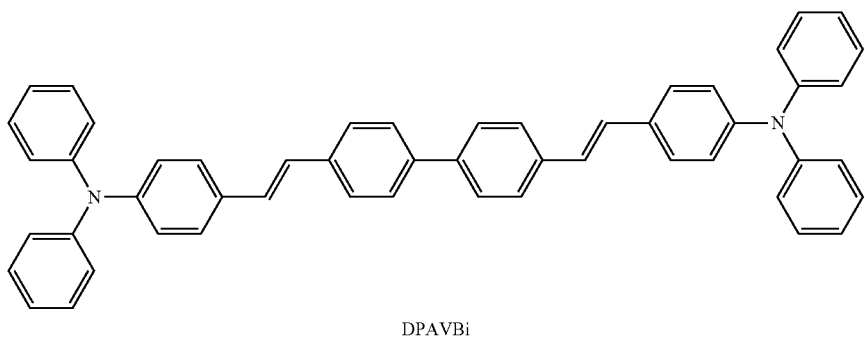
DPAVBi
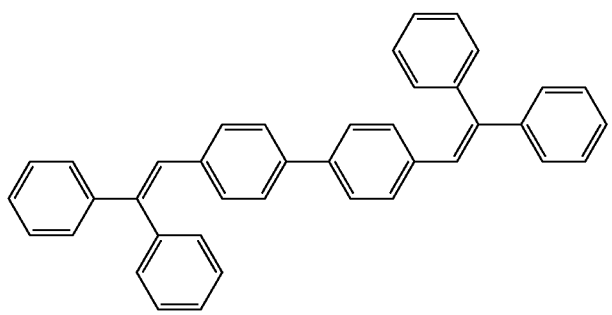
DPABi
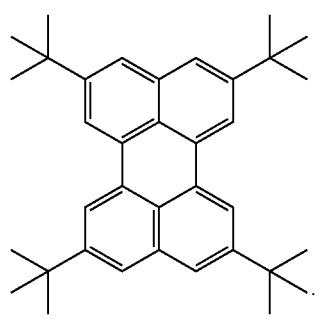
TPBe
In one embodiment, a blue dopant includes at least one of the compounds illustrated below, but is not limited thereto:
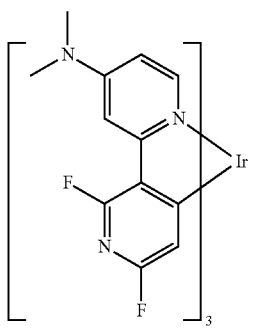
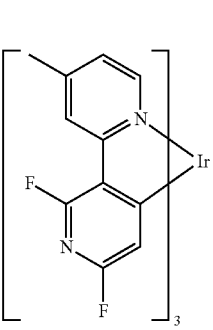
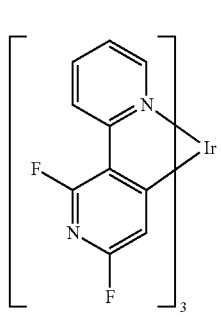

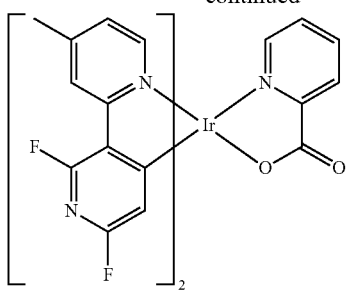
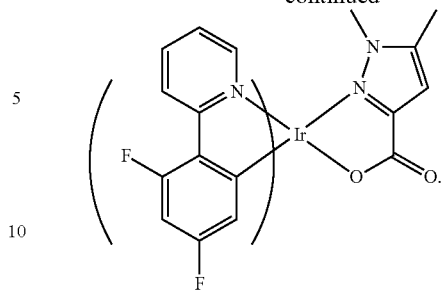

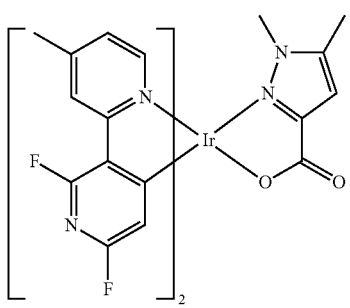

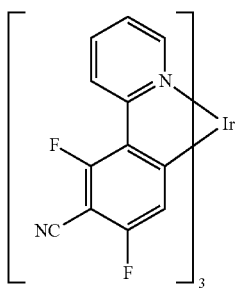

Non-limiting examples of a red dopant include the compounds shown below including Pt(II) octaethylporphine (PtOEP), tris(2-phenylisoquinoline)iridium) (Ir(piq)$_3$), bis(2-(2'-benzothienyl)-pyridinato-N,C3')iridium(acetylacetonate) (Btp$_2$Ir(acac)), 4-(dicyanomethylene)-2-methyl-6-[p-(dimethylamino)styryl]-4H-pyran (DCM), and 4-(dicyanomethylene)-2-tert-butyl-6-(1,1,7,7,-tetramethyl-julolidyl-9-enyl)-4H-pyran (DCJTB):

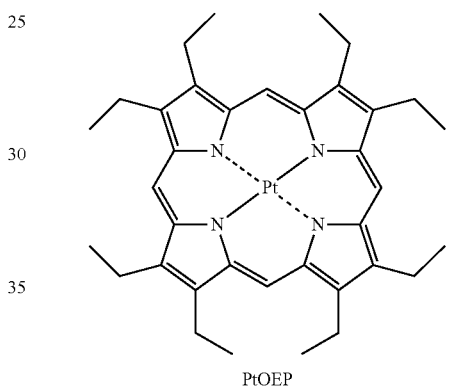
PtOEP

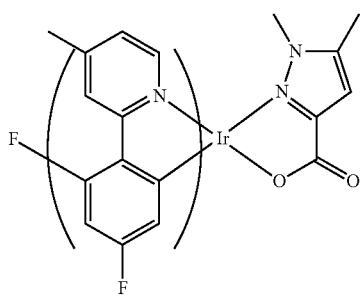

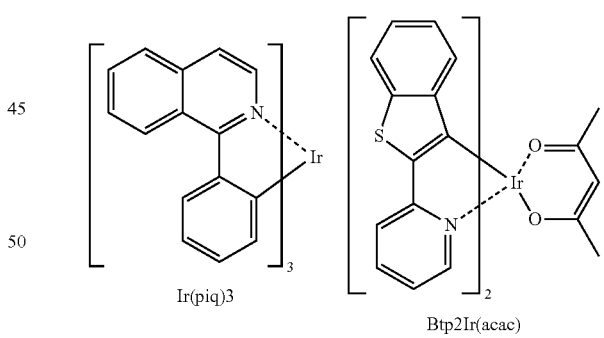
Ir(piq)3    Btp2Ir(acac)

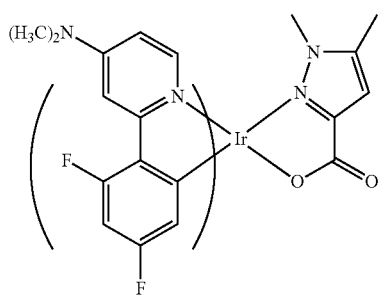

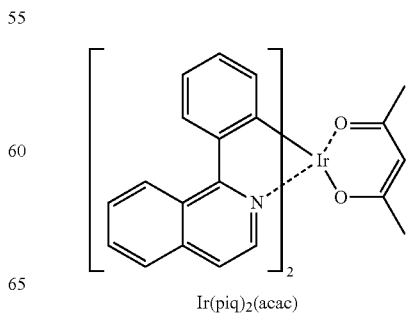
Ir(piq)2(acac)

-continued

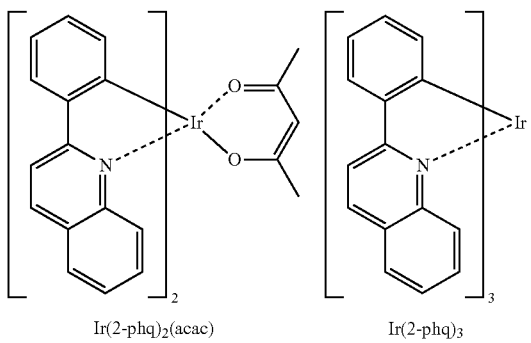

Ir(2-phq)₂(acac)    Ir(2-phq)₃

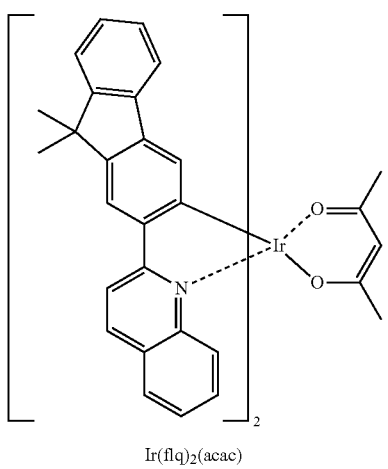

Ir(flq)₂(acac)

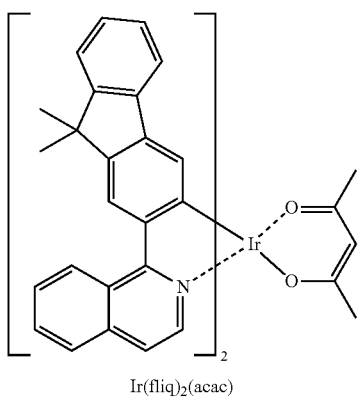

Ir(fliq)₂(acac)

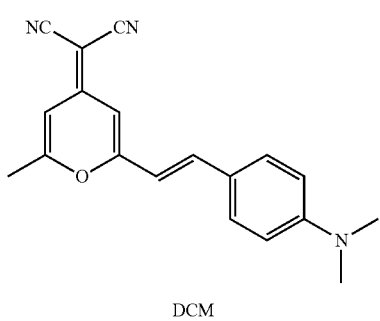

DCM

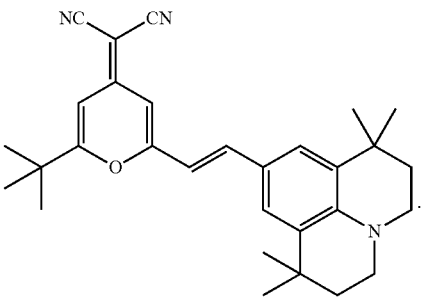

DCJTB

Non-limiting examples of a green dopant include tris(2-phenylpyridine) iridium (Ir(ppy)₃), bis(2-phenylpyridine)(acetylacetonato)iridium(III) (Ir(ppy)₂(acac)), tris(2-(4-tolyl)phenylpiridine)iridium (Ir(mppy)₃), and 10-(2-benzothiazolyl)-1,1,7,7tetramethyl-2,3,6,7-tetrahydro-1H,5H,11H-[1]benzopyrano[6,7,8-ij]-quinolizin-11-one (C545T):

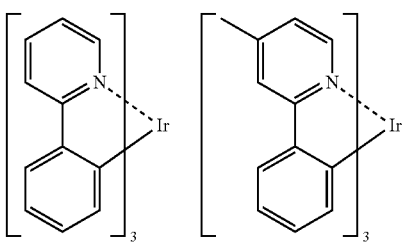

Ir(ppy)₃    Ir(mppy)₃

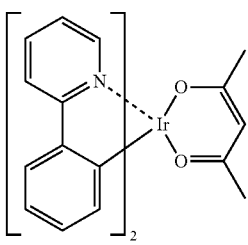

Ir(ppy)₂(acac)

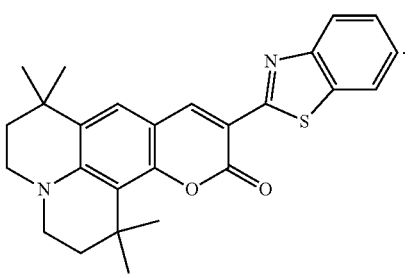

C545T

In one embodiment, the dopant included in the emission layer may be a Pt-complex and may be selected from Compounds D1 to D50, but is not limited thereto:

D1 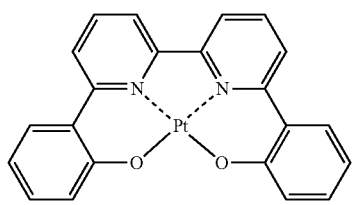
D2 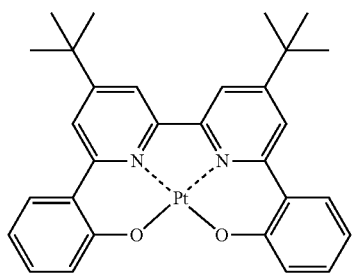
D3 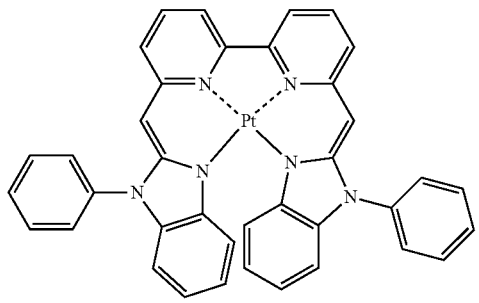
D4 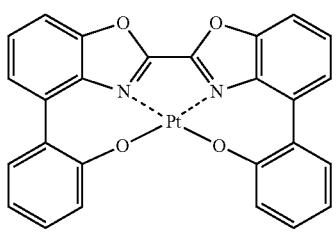
D5 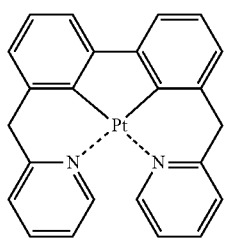
D6 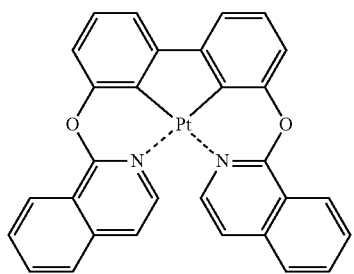
-continued
D7 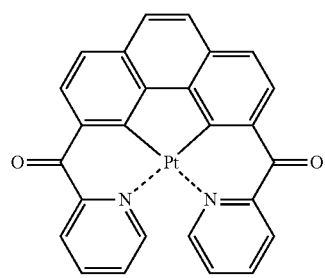
D8 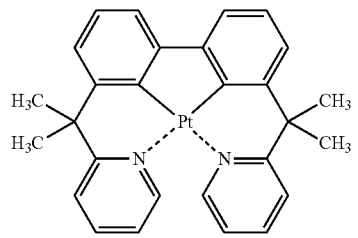
D9 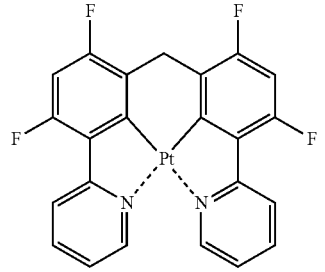
D10 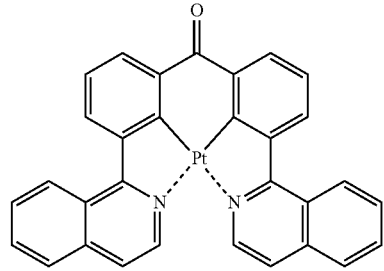
D11 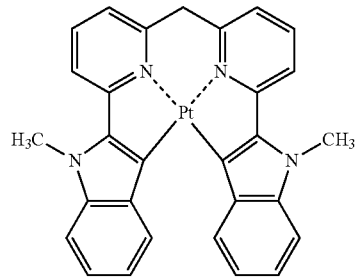
D12 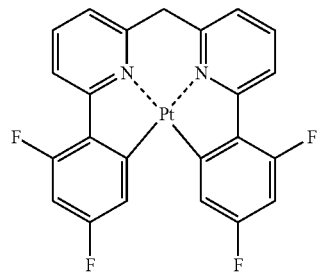

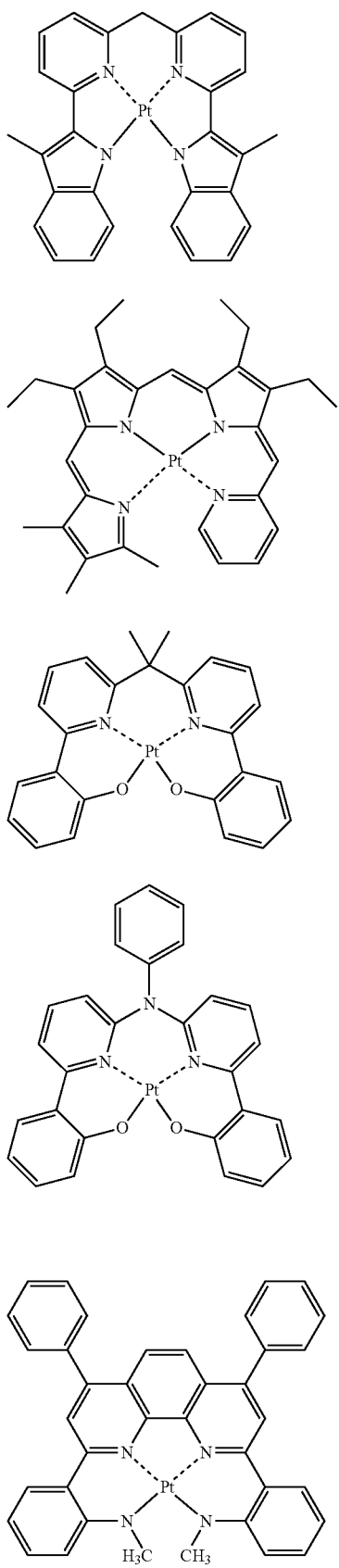
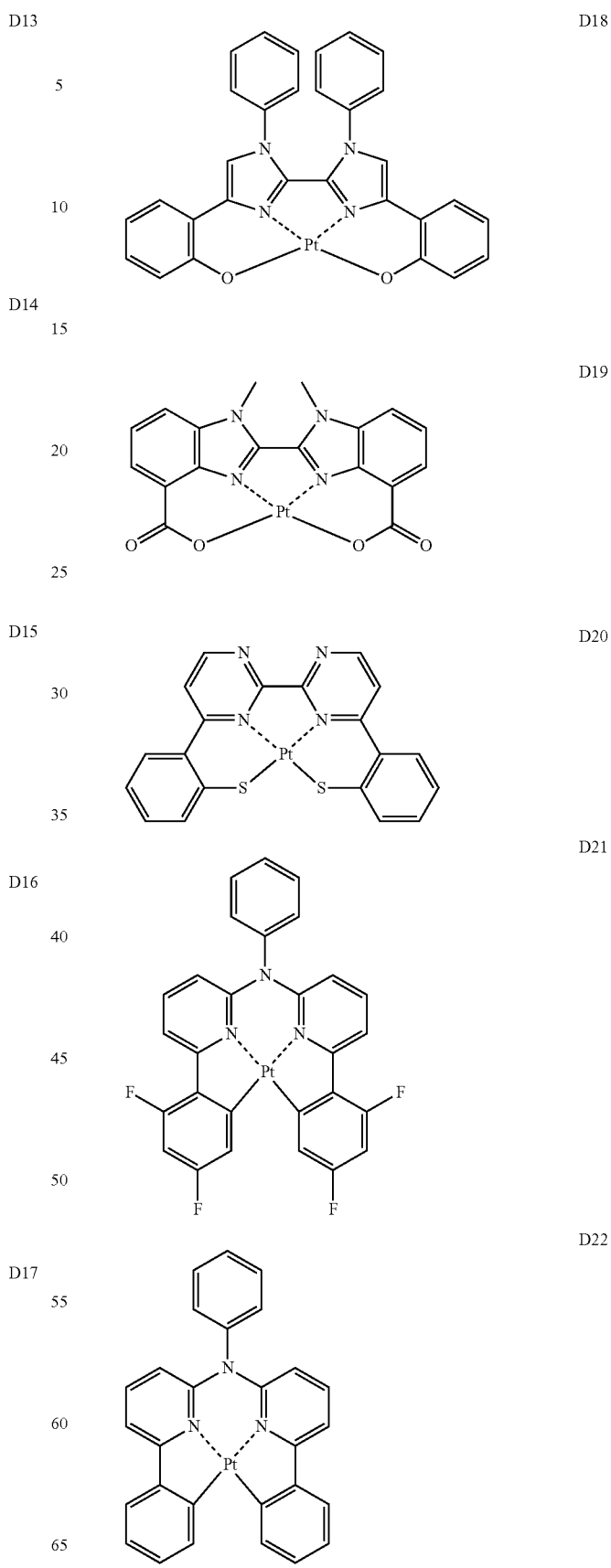

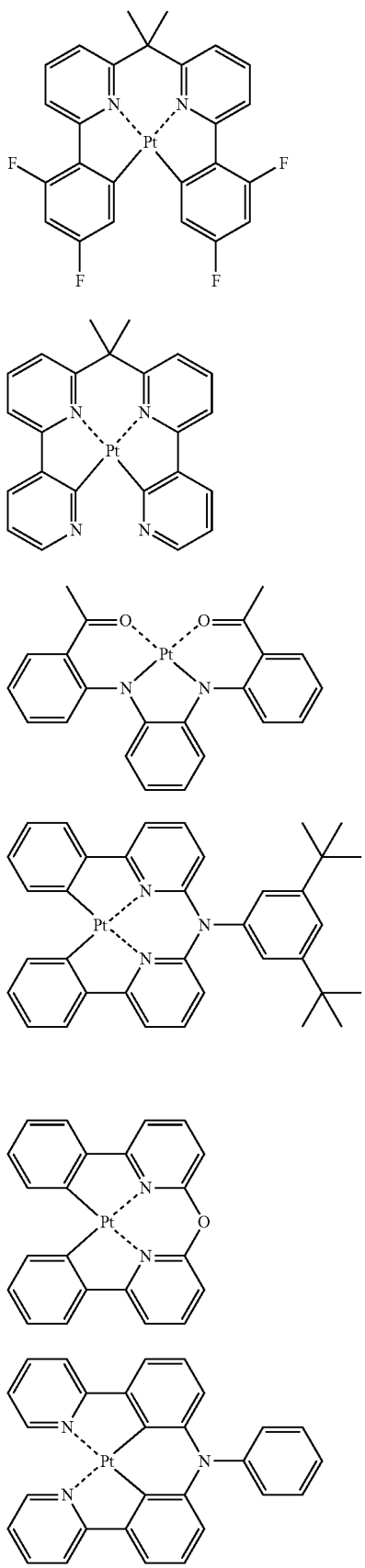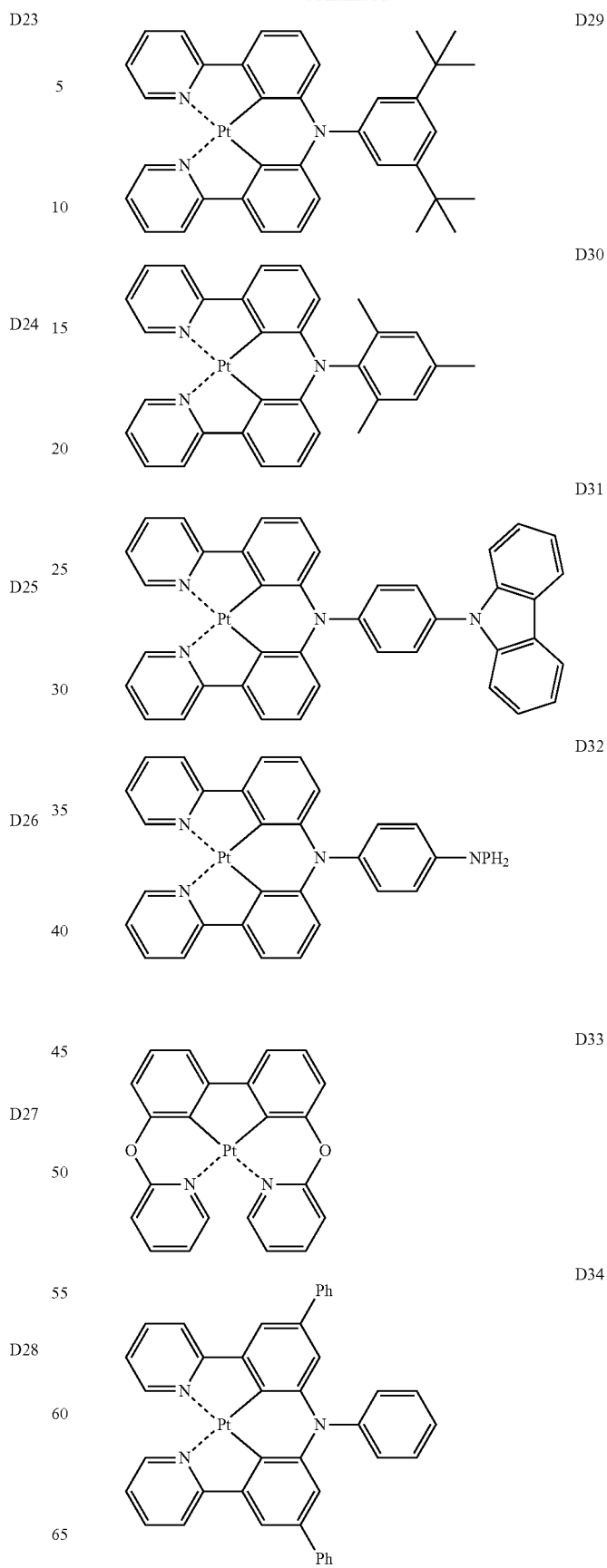

D35 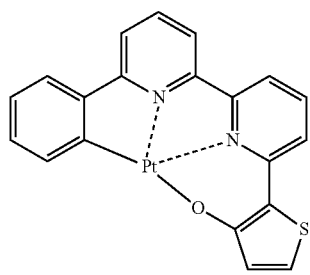
D36 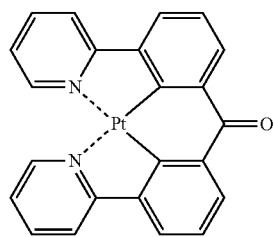
D37 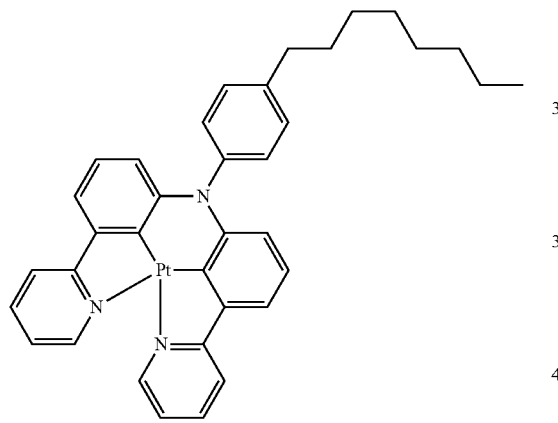
D38 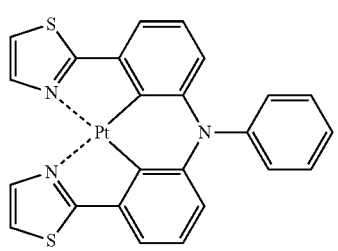
D39 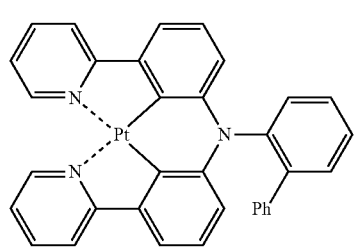
D40 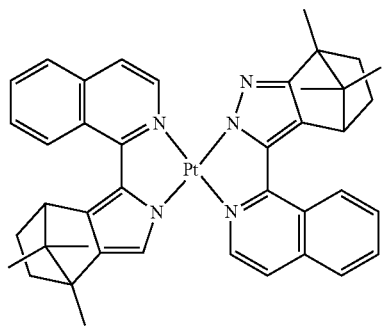
D41 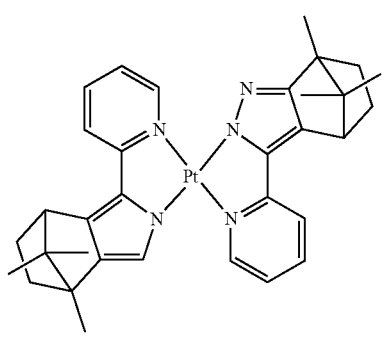
D42 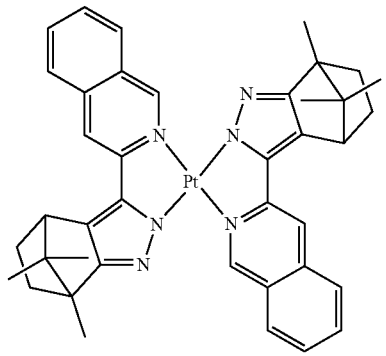
D43 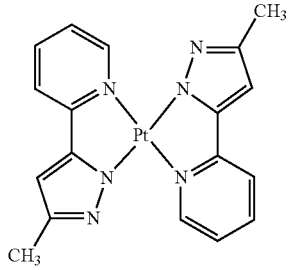
D44 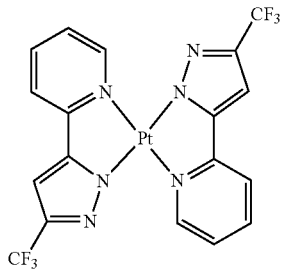

-continued
D45 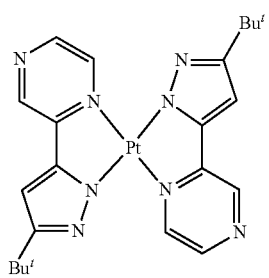
D46 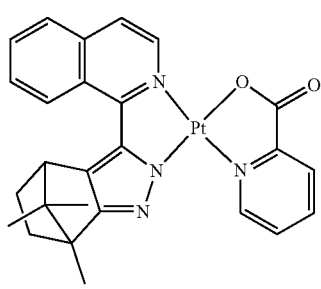
D47 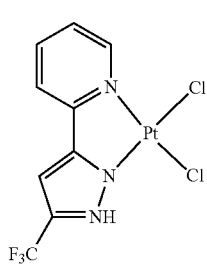
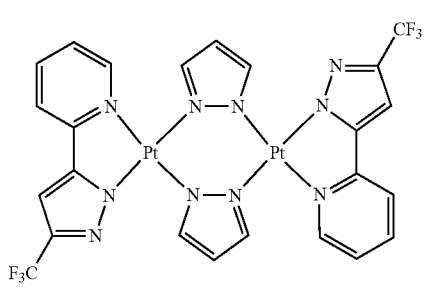
-continued
D50 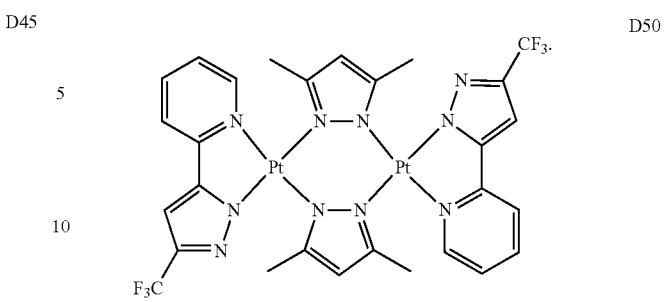
In one embodiment, the dopant included in the emission layer may be selected from Os-complexes illustrated below, but is not limited thereto:
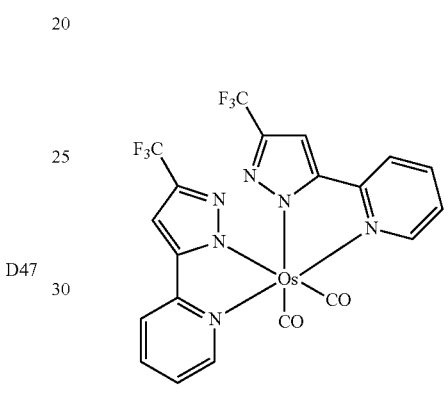
Os(fppz)₂(CO)₂
D48 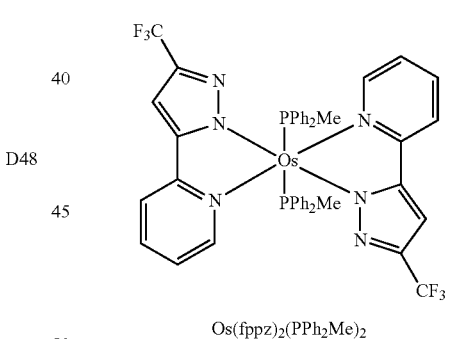
Os(fppz)₂(PPh₂Me)₂
D49 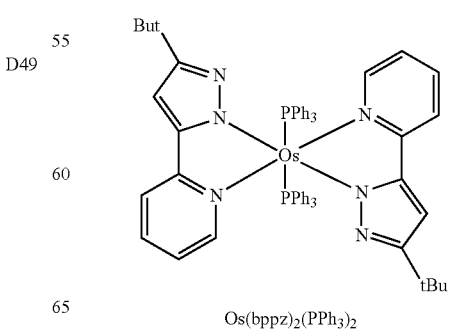
Os(bppz)₂(PPh₃)₂

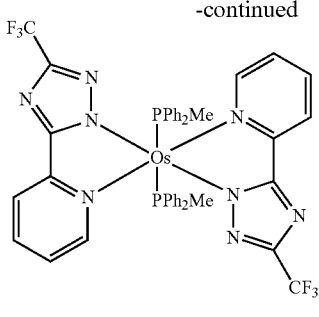

Os(fptz)₂(PPh₂Me)₂

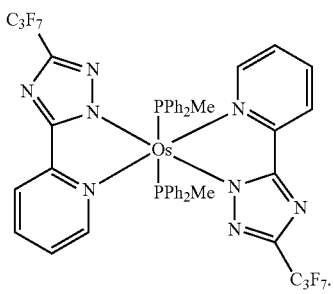

Os(hptz)₂(PPhMe)₂

An amount of the dopant in the emission layer may be about 0.01 to about 15 parts by weight based on 100 parts by weight of the host, but is not limited thereto.

A thickness of the emission layer may be about 100 Å to about 1,000 Å, for example, about 200 Å to about 600 Å. When the thickness of the emission layer is within any of these ranges, good (or desired) light-emission characteristics may be obtained without a substantial increase in driving voltage.

In one embodiment, an electron transport region may be positioned on the emission layer.

The electron transport region may include at least one selected from a hole blocking layer, an electron transport layer (ETL), and an electron injection layer, but is not limited thereto.

For example, the electron transport region may only include an electron transport layer, or may have a structure of electron transport layer/electron injection layer, or a structure of hole blocking layer/electron transport layer/electron injection layer, wherein the layers of each structure are sequentially stacked on the emission layer in the stated order, but the structure of the electron transport region is not limited thereto.

According to one embodiment of the present invention, the organic layer 15 of the organic light-emitting device may include an electron transport region between the emission layer and the second electrode 17.

The electron transport region may include a hole blocking layer. When the emission layer includes a phosphorescent dopant, the hole blocking layer may be formed to prevent (or reduce) the diffusion of excitons or holes into an electron transport layer.

When the electron transport region includes a hole blocking layer, the hole blocking layer may be formed on the emission layer by various methods, such as, for example, vacuum deposition, spin coating casting, a LB method, ink-jet printing, laser-printing, or laser-induced thermal imaging. When the hole blocking layer is formed by vacuum deposition or spin coating, deposition and coating conditions for the hole blocking layer may be similar to the deposition and coating conditions for the hole injection layer.

The hole blocking layer may include, for example, at least one of BCP and Bphen, but is not limited thereto:

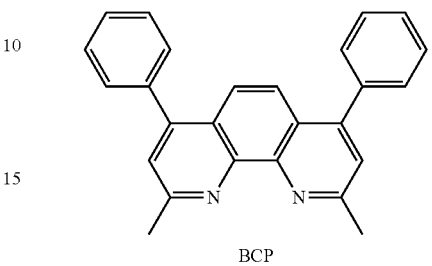

BCP

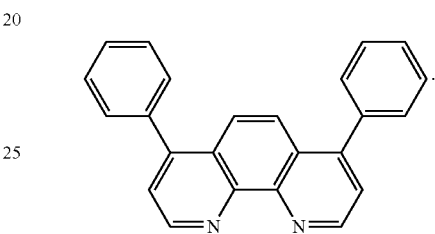

Bphen

A thickness of the hole blocking layer may be about 20 Å to about 1,000 Å, for example, about 30 Å to about 300 Å. When the thickness of the hole blocking layer is within any of these ranges, the hole blocking layer may have improved hole blocking ability without a substantial increase in driving voltage.

The electron transport region may include an electron transport layer. The electron transport layer may be formed on the emission layer or on the hole blocking layer by various methods, such as, for example, vacuum deposition, spin coating casting, a LB method, ink-jet printing, laser-printing, or laser-induced thermal imaging. When the electron transport layer is formed by vacuum deposition or spin coating, deposition and coating conditions for the electron transport layer may be similar to the deposition and coating conditions for the hole injection layer.

The electron transport layer may further include at least one selected from the condensed cyclic compound represented by Formula 1, BCP, Bphen, Alq₃, Balq, TAZ, and NTAZ, some of which are illustrated below:

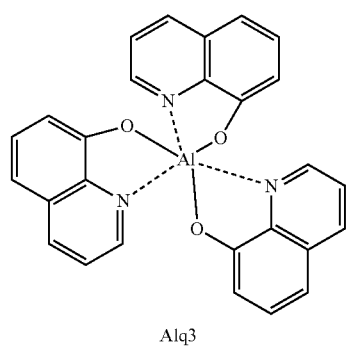

Alq3

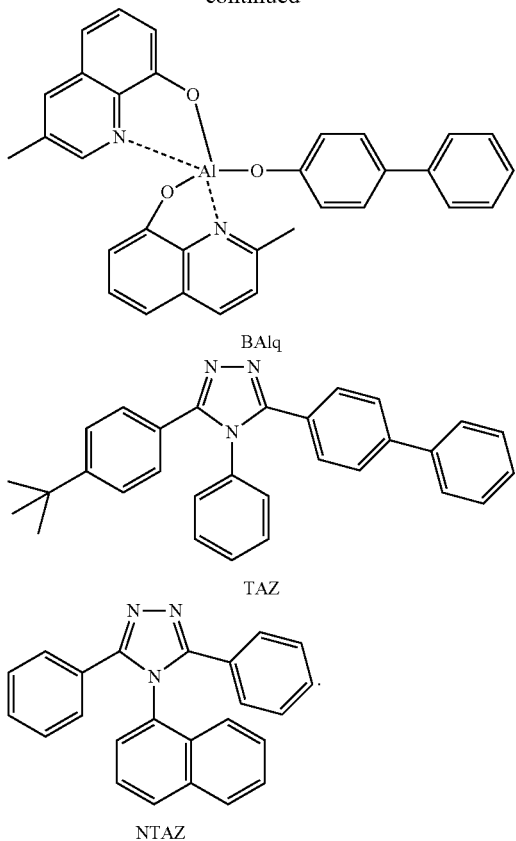

BAlq

TAZ

NTAZ

According to another embodiment of the present invention, the electron transport layer may further include at least one compound represented by Formula 601:

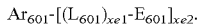  Formula 601

In Formula 601, $Ar_{601}$ may be described as $Ar_{301}$;

$L_{601}$ may be described as $L_{201}$, and in some embodiments, $L_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group;

xe1 may be selected from 0, 1, 2, and 3;

xe2 may be selected from 1, 2, 3, and 4.

In some embodiments of the present invention, the electron transport layer may further include at least one of compounds represented by Formula 602:

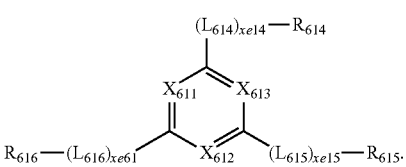  Formula 602

In Formula 602, $X_{611}$ is N or C-$(L_{611})_{xe611}$-$R_{611}$, $X_{612}$ is N or C-$(L_{612})_{xe612}$-$R_{612}$, $X_{613}$ is N or C-$(L_{613})_{xe613}$-$R_{613}$, and at least one of $X_{611}$ to $X_{613}$ is N;

$L_{611}$ to $L_{616}$ may be each independently described as $L_{201}$;

$R_{611}$ to $R_{616}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and the compound represented by Formula 602 may each include at least one of Compounds ET1 to ET15 illustrated below:

ET1

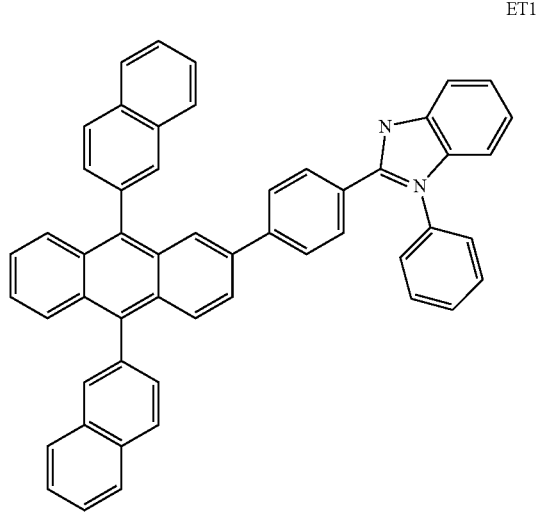

ET2

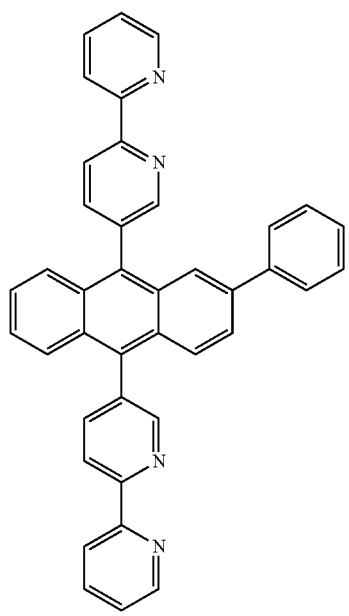

ET3

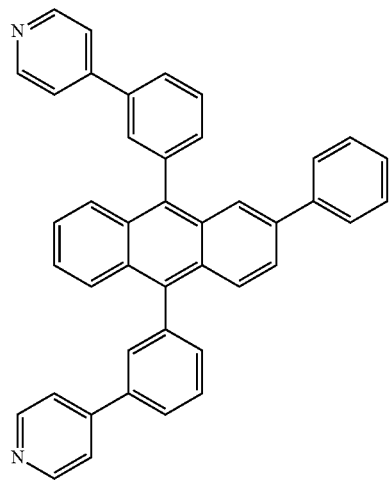

ET4

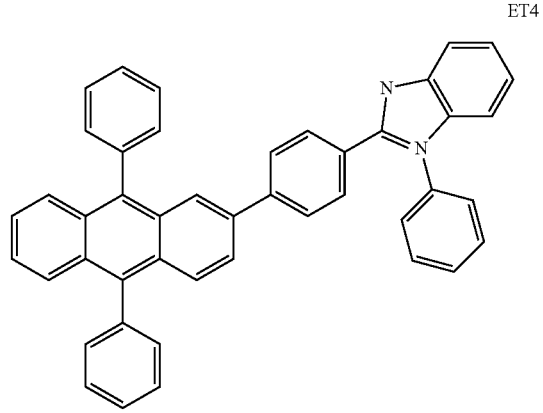

ET5

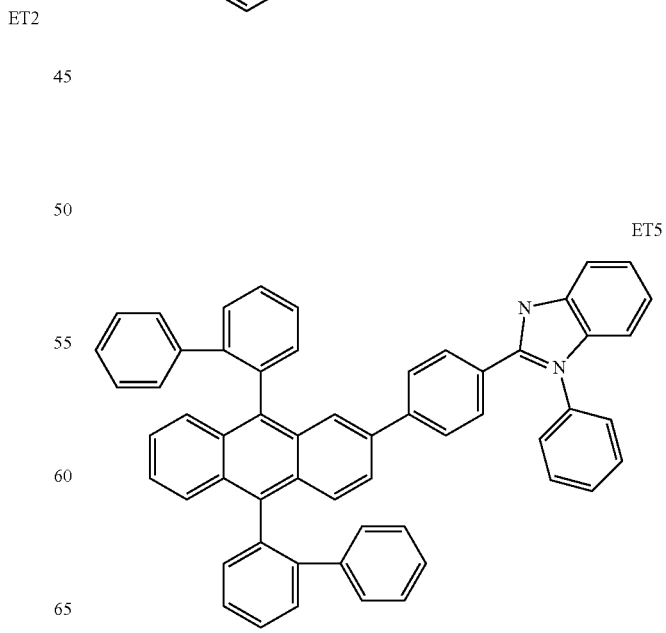

ET6
ET7
ET8
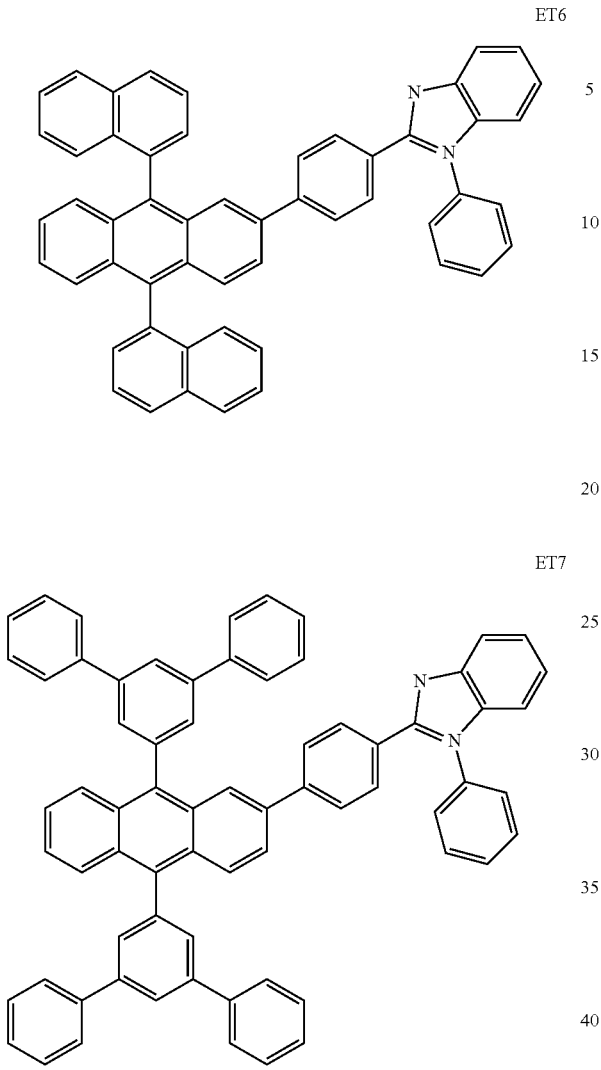
ET9
ET10
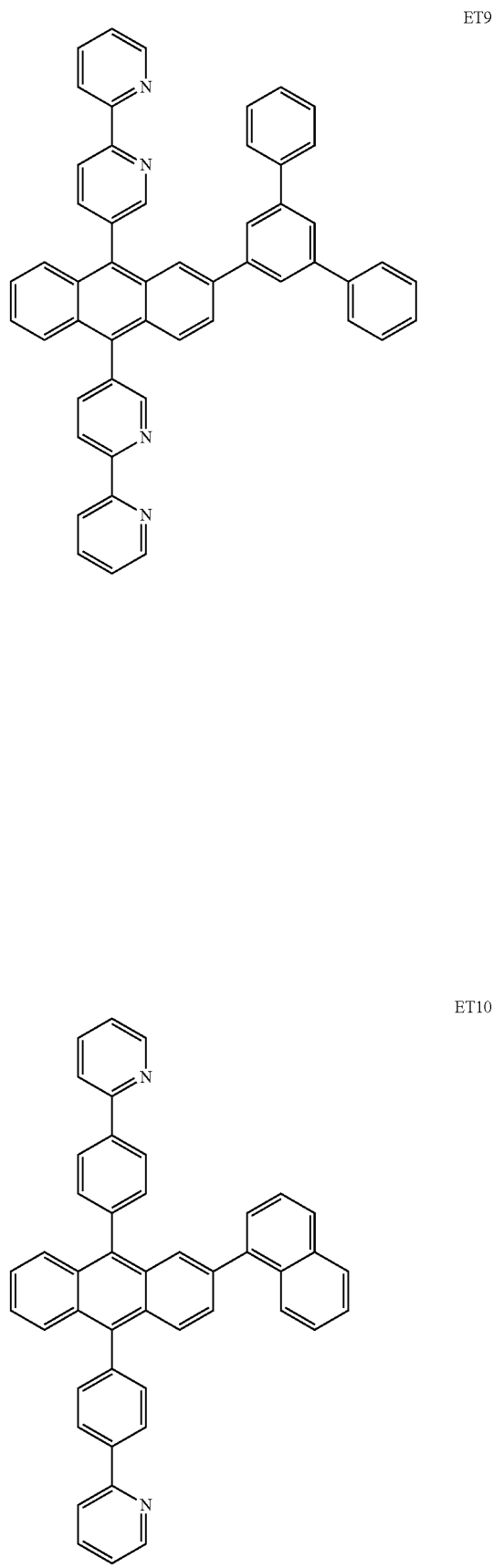

ET11

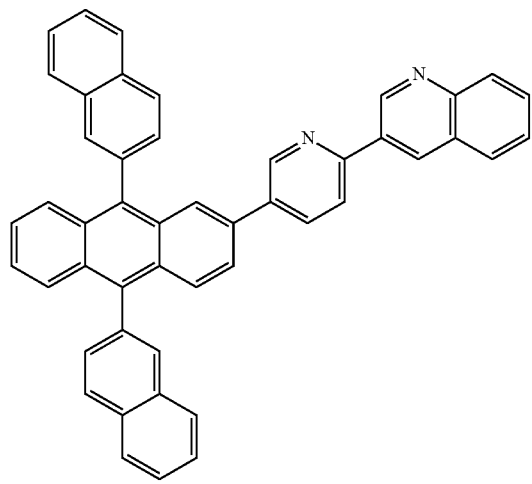

ET12

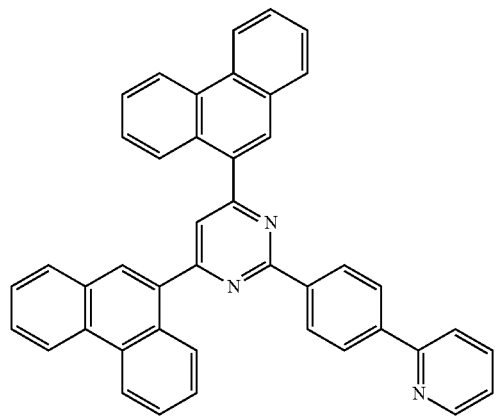

ET13

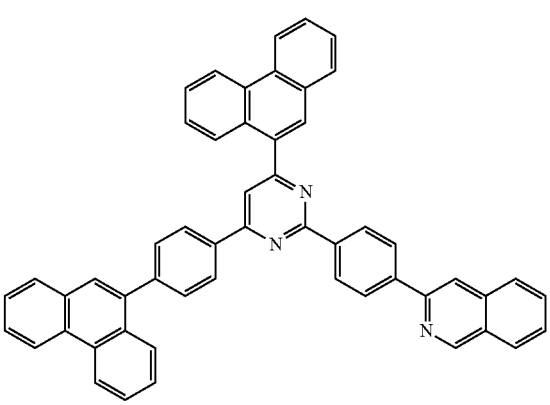

ET14

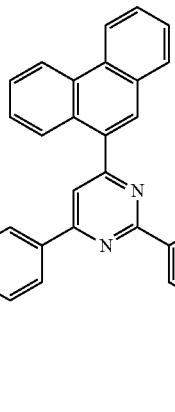

ET15

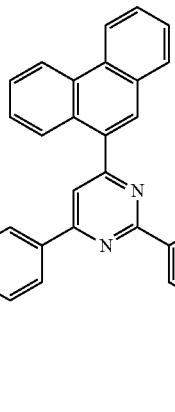

A thickness of the electron transport layer may be about 100 Å to about 1,000 Å, for example, about 150 Å to about 500 Å. When the thickness of the electron transport layer is within any of these ranges, the electron transport layer may have satisfactory electron transport characteristics without a substantial increase in driving voltage.

The electron transport layer may further include, in addition to the materials described above, a metal-containing material.

The metal-containing material may include a Li complex. The Li complex may include, for example, lithium quinolate (LiQ) or lithium [2-(2-hydroxyphenyl)benzothiazole] (LiBTz):

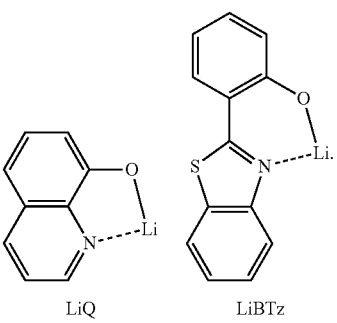

LiQ        LiBTz

The electron transport region may include an electron injection layer that allows electrons to be easily provided (or injected) from the second electrode 17.

The electron injection layer may be formed on the electron transport layer by various methods, such as, for example, vacuum deposition, spin coating casting, a LB method, ink-jet printing, laser-printing, or laser-induced thermal imaging. When the electron injection layer is formed by vacuum deposition or spin coating, deposition and coating conditions for the electron injection layer may be similar to the deposition and coating conditions for the hole injection layer.

The electron injection layer may include, for example, at least one selected from LiF, NaCl, CsF, Li$_2$O, BaO, and LiQ.

A thickness of the electron injection layer may be about 1 Å to about 100 Å, for example, about 3 Å to about 90 Å. When the thickness of the electron injection layer is within any of these ranges, the electron injection layer may have satisfactory electron injection characteristics without a substantial increase in driving voltage.

In one embodiment, the second electrode 17 is positioned on the organic layer 15 having the structure according to embodiments of the present invention. The second electrode 17 may be a cathode (which is an electron injection electrode), and a material for forming the second electrode 17 may be a material having a low work function, for example, a metal, an alloy, an electrically conductive compound, or a mixture thereof. Non-limiting examples of the material for forming the second electrode 17 include lithium (Li), magnesium (Mg), aluminum (Al), aluminum-lithium (Al—Li), calcium (Ca), magnesium-indium (Mg—In), and magnesium-silver (Mg—Ag). According to another embodiment of the present invention, the material for forming the second electrode 17 may be ITO or IZO. The second electrode 17 may be a reflective electrode or a transmissive electrode.

Although the organic light-emitting device has been described with reference to the drawing, embodiments of the present invention are not limited thereto. For example, in the organic light-emitting device shown in the drawing, the substrate 11 is positioned under the first electrode 13, but the substrate 11 can also be positioned above the second electrode 17.

An alkyl group as used herein refers to a linear or branched aliphatic hydrocarbon monovalent group, and non-limiting examples thereof include a methyl group, an ethyl group, a propyl group, an isobutyl group, a sec-butyl group, a ter-butyl group, a pentyl group, an iso-amyl group, and a hexyl group. An alkylene group as used herein refers to a divalent group having the same structure as the alkyl group.

An alkoxy group as used herein refers to a monovalent group represented by —OA$_{101}$ (where A$_{101}$ is a C$_1$-C$_{60}$ alkyl group), and non-limiting examples of the alkoxy group include a methoxy group, an ethoxy group, and an isopropyloxy group.

An alkenyl group as used herein refers to a hydrocarbon group having at least one carbon-carbon double bond at one or more positions along a carbon chain of the alkyl group. For example, the alkenyl group may include a terminal alkene and/or an internal alkene, and non-limiting examples thereof include an ethenyl group, a propenyl group, and a butenyl group. An alkenylene group as used herein refers to a divalent group having the same structure as the alkenyl group.

An alkynyl group as used herein refers to a hydrocarbon group having at least one carbon-carbon triple bond at one or more positions along a carbon chain of the alkyl group. For example, the alkynyl group may include a terminal alkyne and/or an internal alkyne, and non-limiting examples thereof include an ethynyl group, a propynyl group, and a butynyl group. An alkynylene group as used herein refers to a divalent group having the same structure as the alkynyl group.

A cycloalkyl group as used herein refers to a monovalent hydrocarbon monocyclic group, and non-limiting examples thereof include a cyclopropyl group, a cyclobutyl group, a cyclopentyl group, a cyclohexyl group, and a cycloheptyl group. A cycloalkylene group as used herein refers to a divalent group having the same structure as the cycloalkyl group.

A heterocycloalkyl group as used herein refers to a monovalent monocyclic group that has at least one heteroatom selected from N, O, P, and S as a ring-forming atom, and carbon atoms as the remaining ring-forming atoms. Non-limiting examples of the heterocycloalkyl group include a tetrahydrofuranyl group and a tetrahydrothiophenyl group. A heterocycloalkylene group as used herein refers to a divalent group having the same structure as the heterocycloalkyl group.

A cycloalkenyl group as used herein refers to a monovalent monocyclic group that has at least one carbon-carbon double bond in the ring, but does not have aromaticity, and non-limiting examples thereof include a cyclopentenyl group, a cyclohexenyl group, and a cycloheptenyl group. A cycloalkenylene group as used herein refers to a divalent group having the same structure as the cycloalkenyl group.

A heterocycloalkenyl group as used herein refers to a monovalent monocyclic group that has at least one heteroatom selected from N, O, P, and S as a ring-forming atom (and carbon atoms as the remaining ring-forming atoms), and at least one double bond in the ring. Non-limiting examples of the heterocycloalkenyl group include a 2,3-hydrofuranyl group and a 2,3-hydrothiophenyl group. A hetetocycloalkenylene as used herein refers to a divalent group having the same structure as the heterocycloalkenyl group.

An aryl group as used herein refers to a monovalent group that has a carbocyclic aromatic system, and an arylene group as used herein refers to a divalent group that has a carbocyclic aromatic system. Non-limiting examples of the aryl group include a phenyl group, a naphthyl group, an anthracenyl group, a phenanthrenyl group, a pyrenyl group, and a chrysenyl group. When the aryl group and/or the arylene group have at least two rings, the rings may be respectively fused to each other.

A heteroaryl group as used herein refers to a monovalent group that has at least one heteroatom selected from N, O, P, and S as a ring-forming atom (and carbon atoms as the remaining ring-forming atoms) and a carbocyclic aromatic system. A heteroarylene group as used herein refers to a divalent group that has at least one heteroatom selected from N, O, P, and S as a ring-forming atom (and carbon atoms as the remaining ring-forming atoms) and a carbocyclic aromatic system. Non-limiting examples of the heteroaryl group include a pyridinyl group, a pyrimidinyl group, a pyrazinyl group, a pyridazinyl group, a triazinyl group, a quinolinyl group, and an isoquinolinyl group. When the heteroaryl group and/or the heteroarylene group include two or more rings, the rings may be respectively fused to each other.

An aryloxy group as used herein refers to a monovalent group represented by —OA$_{102}$ (where A$_{102}$ is the aryl group), and an arylthio group as used herein refers to a monovalent group represented by —SA$_{103}$ (where A$_{103}$ is the aryl group.)

A monovalent non-aromatic condensed polycyclic group as used herein refers to a monovalent group that has two or more rings condensed to each other, and the entire molecular structure does not have aromaticity. The monovalent non-aromatic condensed polycyclic group may include only carbon atoms as ring-forming atoms, or at least one heteroatom selected from N, O, P, and S as a ring-forming atom (and carbon atoms as the remaining ring-forming atoms). Non-limiting examples of the monovalent non-aromatic condensed polycyclic group include a heptalenyl group and a triquinacenyl group. Herein, a divalent non-aromatic condensed polycyclic group refers to a divalent group that has the same structure as the monovalent non-aromatic condensed polycyclic group.

$C_m$-$C_n$ (m<n) as used herein refers to a number of carbon atoms in a given group. For example, a $C_1$-$C_{10}$ alkyl group refers to an alkyl group that has between 1 and 10 carbon atoms, and a $C_6$-$C_{30}$ aryl group refers to an aryl group that has between 6 and 30 carbon atoms.

Hereinafter, an organic light-emitting device according to an embodiment of the present invention will be described in more detail with reference to Synthesis Examples and Examples. The expression "B was included instead of A" in describing Synthesis Examples means that a molar equivalent of A was identical to a molar equivalent of B.

Synthesis Example

Synthesis Example 1: Synthesis of Compound 101

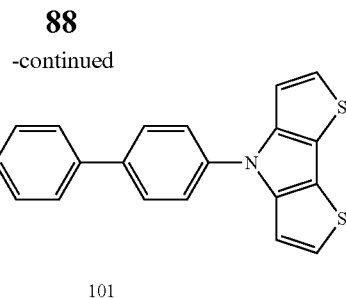

101

3 g (13.7 mmol) of 4-iodo-phenylamine was dissolved in 30 ml of DMF/H$_2$O to synthesize 1.89 g (75%) of biphenyl-4,4'-diamine (Intermediate A) through Buchwald-Hartwig amination.

2.96 g (17.8 mmol) of [2,2']bithiophenyl was subjected to bromination to prepare 3,5,3',5'-tetrabromo-[2,2']bithiophenyl, and then 3.45 g (13.3 mmol, 80%) of 3,3'-dibromo-[2,2']bithiophenyl (Intermediate B) was synthesized via a debromination reaction using zinc. Afterward, the synthesized Intermediate A and Intermediate B were added to 30 ml of toluene, and the resulting solution was used (utilized) to perform Buchwald-Hartwig amination using (utilizing) Pd$_2$(dba)$_3$, CHCl$_3$, dppf(1',1'-bis(diphenyldiphosphino)ferrocene), and NaOt-Bu to synthesize Compound 101 (2.08 g, 40%).

Synthesis Example 2: Synthesis of Compound 107

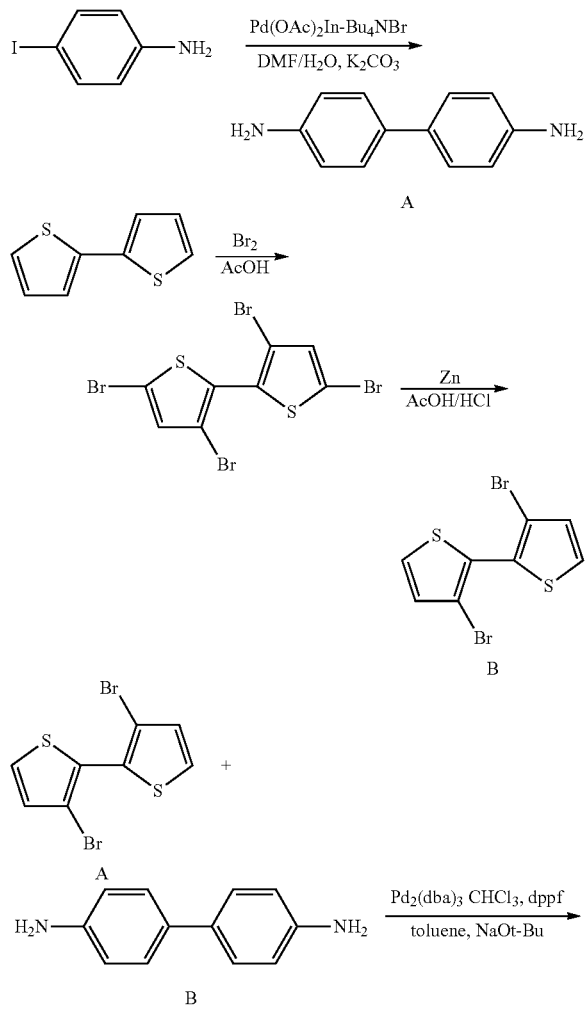

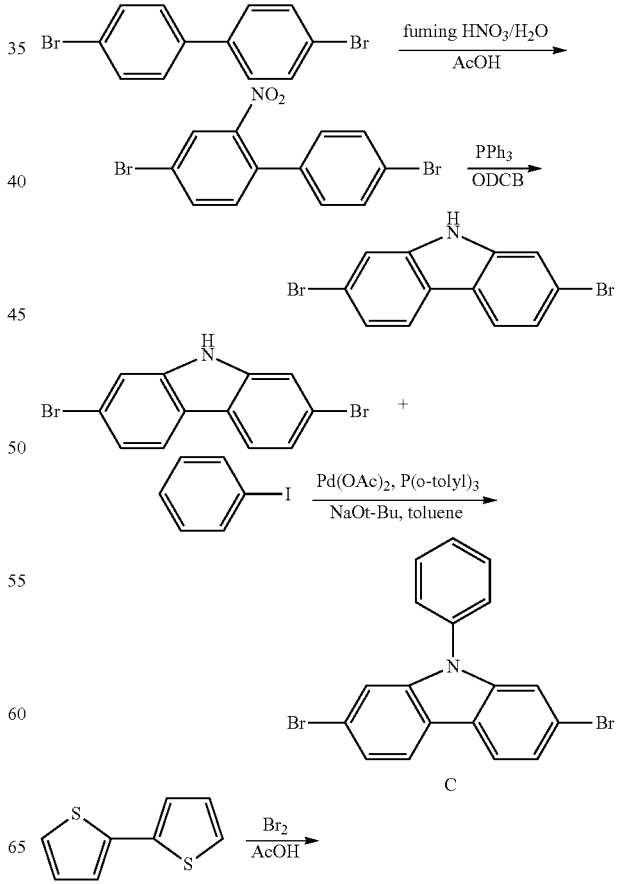

Synthesis Example 3: Synthesis of Compound 109

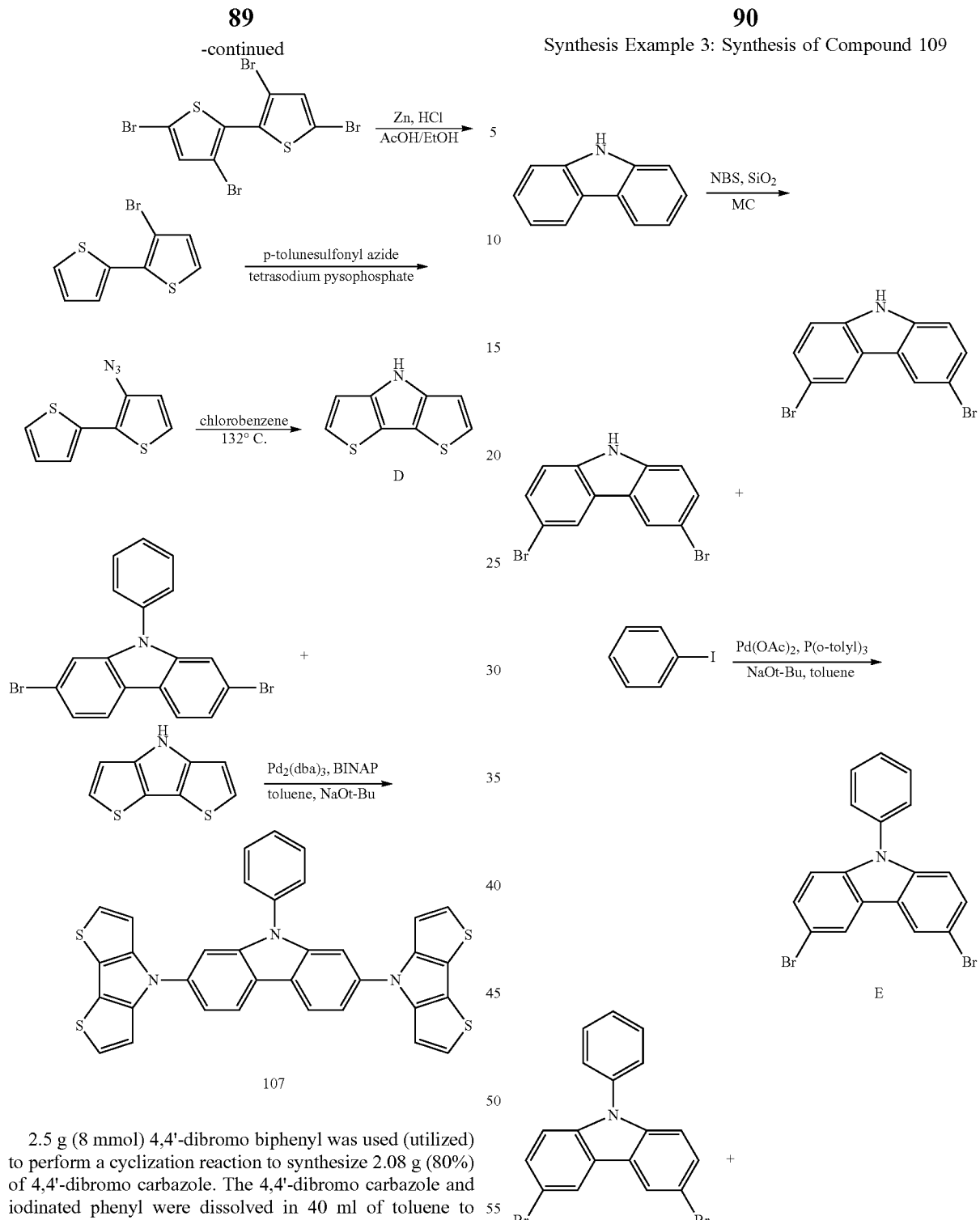

2.5 g (8 mmol) 4,4'-dibromo biphenyl was used (utilized) to perform a cyclization reaction to synthesize 2.08 g (80%) of 4,4'-dibromo carbazole. The 4,4'-dibromo carbazole and iodinated phenyl were dissolved in 40 ml of toluene to synthesize Intermediate C through a Buchwald reaction.

2.96 g (17.8 mmol) of [2,2']bithiophenyl was used (utilized) to prepare 3,5,3',5'-tetrabromo-[2,2']bithiophenyl via bromination, and then 2.16 g (55%) of 3-bromo-[2,2']bithiophenyl was synthesized through a debromination reaction using zinc. Then, the 3-bromo-[2,2']bithiophenyl was used (utilized) to perform a nucleophilic substitution reaction (SN2 reaction) and a cyclization reaction to synthesize Intermediate D. The Intermediate C and Intermediate D were then used (utilized) to perform Buchwald-Hartwig cross-coupling to synthesize 2.99 g (83%) of Compound 107.

-continued

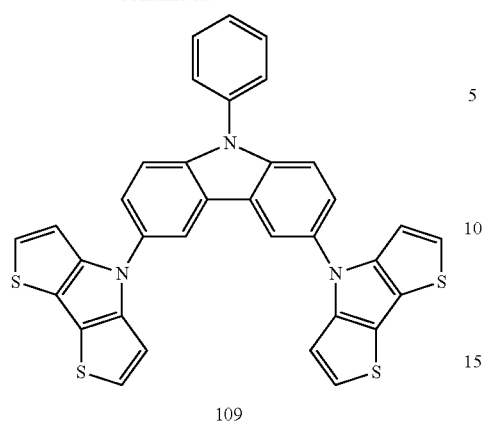

109

2.5 g (14.9 mmol) of carbazole was used (utilized) to perform an NBS bromination to synthesize 2,5-dibromocarbazole. Then, the 2,5-dibromocarbazole and iodinated phenyl were used (utilized) to synthesize 3.72 g (9.28 mmol) of Intermediate E through a Buchwald reaction.

Afterward, the Intermediate E and Intermediate D were used (utilized) to perform Buchwald-Hartwig cross-coupling to synthesize 3.65 g (66%) of Compound 109.

Synthesis Example 4: Synthesis of Compound 121

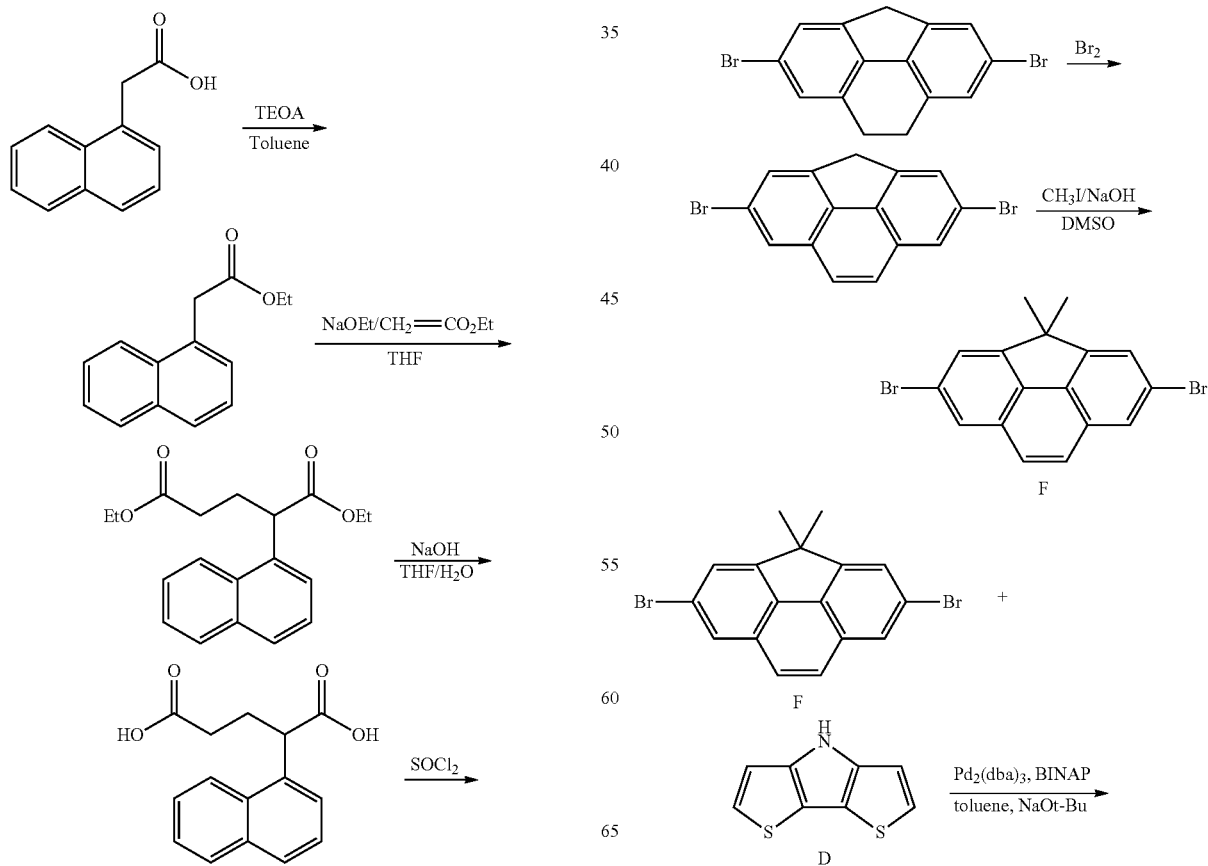

-continued

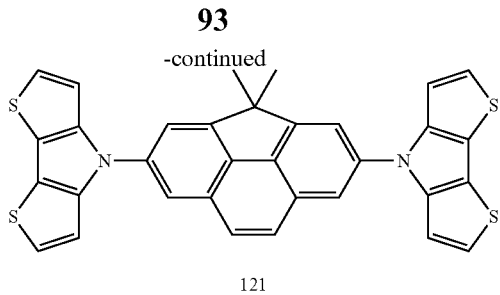

121

2.5 g (14.9 mmol) of naphthalene acetic acid was used (utilized) to synthesize 2.3 g of the Intermediate F (1 equivalent weight) and 2.4 g of the Intermediate D (2.2 equivalent weight) through the synthesis pathway represented by the reaction scheme shown above, and then 2.52 g (72%) of Compound 121 was synthesized by performing Buchwald-Hartwig cross-coupling.

The $^1$H NMR and MS/FAB results of the synthesized compounds are shown in Table 1.

Methods of synthesizing compounds other than the compounds shown in Table 1 should be apparent to those of ordinary skill in the art by referring to the synthesis path and source materials described above.

TABLE 1

| Compound | $^1$H NMR (CDCl$_3$, 300 MHz) | MS/FAB Measured value | MS/FAB Calculated value |
|---|---|---|---|
| 101 | 6.96(4H), 7.2(4H), 7.3(4H), 7.5(4H) | 508.02 | 508.70 |
| 107 | 6.96(4H), 7.0(2H), 7.2(4H), 7.3(5H), 7.4(2H), 7.6(2H) | 597.05 | 597.79 |
| 109 | 6.96(4H), 7.1(2H), 7.2(4H), 7.3(5H), 7.4(2H), 7.6(2H) | 597.05 | 597.79 |
| 121 | 1.93(6H), 6.96(4H), 7.2(4H), 7.7(2H), 7.8(2H), 7.9(2H) | 572.05 | 572.79 |

EXAMPLE

Example 1

An ITO glass substrate (a product of Corning Co., Ltd) having an ITO layer having a thickness of 1200 Å and a sheet resistance of 15Ω/□ was cut to a size of 50 mm×50 mm×0.7 mm, and then, sonicated with isopropyl alcohol and pure water, each for 5 minutes, and cleaned by exposure to ultraviolet rays for 30 minutes, and then to ozone, and the resulting ITO glass substrate was mounted on a vacuum deposition apparatus.

2-TNATA was deposited on the ITO anode to form a hole injection layer having a thickness of 600 Å, and then, Compound 101 was deposited on the hole injection layer to form a hole transport layer having a thickness of 300 Å. On the hole transport layer, an emission layer having a thickness of 200 Å was formed by using (utilizing) 95 wt % ADN and 5% F$_2$Irpic as a blue dopant.

Thereafter, Alq$_3$ was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 3000 Å, thereby manufacturing an organic light-emitting device.

Example 2

An organic light-emitting device was manufactured as in Example 1, except that in forming a hole transport layer, Compound 107 was included instead of Compound 1.

Example 3

An organic light-emitting device was manufactured as in Example 1, except that in forming a hole transport layer, Compound 109 was used instead of Compound 1.

Example 4

An organic light-emitting device was manufactured in the same manner as in Example 1, except that in forming a hole transport layer, Compound 121 was included instead of Compound 1.

Comparative Example 1

An organic light-emitting device was manufactured as in Example 1, except that in forming a hole transport layer, NPB was included instead of Compound 101, and in forming an electron transport layer, BAlq was included instead of Alq$_3$.

Comparative Example 2

An organic light-emitting device was manufactured as in Example 1, except that in forming a hole transport layer, NPB was included instead of Compound 101, and in forming an electron transport layer, TAZ was included instead of Alq$_3$.

Evaluation Example

The driving voltage and light-emitting efficiency of each of the organic light-emitting devices of Examples 1 to 4 and Comparative Examples 1 to 2 were measured, and the results are shown in Table 2.

TABLE 2

| | Hole transport layer | Electron transport layer | Driving voltage (V) | Brightness (cd/m$^2$) | Light-emitting efficiency (cd/A) | Emission color |
|---|---|---|---|---|---|---|
| Example 1 | Compound 101 | Alq$_3$ | 3.9 | 494 | 4.84 | Blue |
| Example 2 | Compound 107 | Alq$_3$ | 4.0 | 467 | 5.37 | Blue |
| Example 3 | Compound 109 | Alq$_3$ | 3.7 | 477 | 4.97 | Blue |
| Example 4 | Compound 121 | Alq$_3$ | 4.6 | 389 | 4.11 | Blue |
| Comparative Example 1 | NPB | BAlq | 4.9 | 205 | 2.35 | Blue |
| Comparative Example 2 | NPB | TAZ | 4.4 | 302 | 4.01 | Blue |

As can be seen from the results in Table 1, the driving voltage, brightness, current efficiency, and half-life span of the organic light-emitting devices of Example 1 to Example 4 are better than the driving voltage, brightness, current efficiency, and half-life span of the organic light-emitting devices of Comparative Examples 1 and 2.

The organic light-emitting device including the condensed cyclic compound according to embodiments of the present invention may have a low driving voltage, high efficiency, high brightness, and long lifespan.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the drawing, it will be understood by those of ordinary skill in the art that various changes in form and details may be made therein without departing from the spirit and scope of the present invention as defined by the following claims and equivalents thereof.

What is claimed is:

1. A condensed cyclic compound represented by Formula 1:

Formula 1

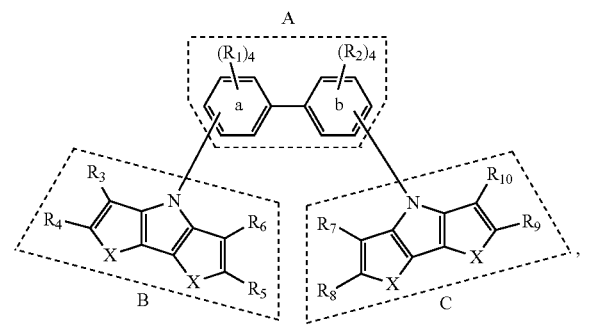

wherein

X is an oxygen (O) atom or a sulfur (S) atom;

$R_1$ to $R_{10}$ are each independently selected from a hydrogen, a deuterium, a halogen atom, a cyano group, a nitro group, a hydroxyl group, a carboxylic acid, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_1$-$C_{30}$ heteroaryl group, a substituted or unsubstituted $C_6$-$C_{30}$ aryloxy group, a substituted or unsubstituted $C_6$-$C_{30}$ arylthio group, and a substituted or unsubstituted monovalent $C_6$-$C_{30}$ non-aromatic condensed polycyclic group, each $R_1$ in a plurality of $R_1$ and each $R_2$ in a plurality of $R_2$ are independent of one another, at least one of the plurality of $R_1$ and the plurality of $R_2$ is optionally linked to an adjacent $R_1$ and/or $R_2$ to form a condensed ring with at least one selected from 'a' benzene ring and 'b' benzene ring;

at least one substituent of the substituted $C_1$-$C_{10}$ alkyl group, substituted $C_2$-$C_{10}$ alkenyl group, substituted $C_2$-$C_{10}$ alkynyl group, substituted $C_1$-$C_{10}$ alkoxy group, substituted $C_3$-$C_{10}$ cycloalkyl group, substituted $C_3$-$C_{10}$ cycloalkenyl group, substituted $C_3$-$C_{10}$ heterocycloalkyl group, substituted $C_3$-$C_{10}$ heterocycloalkenyl group, substituted $C_6$-$C_{30}$ aryl group, substituted $C_1$-$C_{30}$ heteroaryl group, substituted $C_6$-$C_{30}$ aryloxy group, substituted $C_6$-$C_{30}$ arylthio group, and substituted monovalent $C_6$-$C_{30}$ non-aromatic condensed polycyclic group is selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl, and a $C_1$-$C_{10}$ alkoxy group;

a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, and a $C_6$-$C_{30}$ arylthio group, and a monovalent $C_6$-$C_{30}$ non-aromatic condensed polycyclic group, each substituted with at least one selected from a deuterium, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, $C_3$-$C_{10}$ a cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{21}$)($Q_{22}$), —Si($Q_{23}$)($Q_{24}$)($Q_{25}$), and —B($Q_{26}$)($Q_{27}$); and —Si($Q_{31}$)($Q_{32}$)($Q_{33}$) and —B($Q_{34}$)($Q_{35}$), wherein $Q_{11}$ to $Q_{17}$, $Q_{21}$ to $Q_{27}$, and $Q_{31}$ to $Q_{35}$ are each independently selected from a hydrogen, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

2. The condensed cyclic compound of claim 1, wherein the plurality of $R_1$ are each independently selected from a hydrogen and a $C_1$-$C_{10}$ alkyl group, or at least one $R_1$ of the plurality of $R_1$ is selected from a hydrogen and a $C_1$-$C_{10}$ alkyl group, and two or more $R_1$ of the plurality of $R_1$ different from the at least one $R_1$ of the plurality of $R_1$ are linked to each other to form a substituted or unsubstituted naphthylene group or a substituted or unsubstituted anthrylene group with the 'a' benzene ring, and wherein at least one substituent of the substituted naphthylene group and the substituted anthrylene group is selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

3. The condensed cyclic compound of claim 1,
wherein the plurality of $R_2$ are each independently selected from a hydrogen and a $C_1$-$C_{10}$ alkyl group,
or at least one $R_2$ of the plurality of $R_2$ is selected from a hydrogen and a $C_1$-$C_{10}$ alkyl group, and two or more $R_2$ of the plurality of $R_2$ different from the at least one $R_2$ of the plurality of $R_2$ are linked to each other to form a substituted or unsubstituted naphthylene group or a substituted or unsubstituted anthrylene group with the 'b' benzene ring, and wherein at least one substituent of the substituted naphthylene group and the substituted anthrylene group is selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

4. The condensed cyclic compound of claim 1,
wherein at least one of the plurality of $R_1$ and the plurality of $R_2$ is selected from a hydrogen and a $C_1$-$C_{10}$ alkyl group,
and at least another one $R_1$ of the plurality of $R_1$ and at least another one $R_2$ of the plurality of $R_2$ are linked to each other to form a substituted or unsubstituted $C_{13}$-$C_{30}$ condensed ring with the 'a' and 'b' benzene rings, and wherein at least one substituent of the substituted $C_{13}$-$C_{30}$ condensed ring is selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

5. The condensed cyclic compound of claim 1,
wherein $R_3$ to $R_{10}$ are each independently selected from a hydrogen, a methyl group, an ethyl group, a propyl group, a butyl group, a pentyl group, a hexyl group, a heptyl group, an octyl group, a nonyl group, a decyl group, a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro fluorenyl group, a pyrrolyl group, a furyl group, a pyrazolyl group, an imidazolyl group, an oxazolyl group, an isoxazolyl group, a triazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, an benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, a benzocarbazolyl group, and a dibenzacridinyl group; and a methyl group, an ethyl group, a propyl group, a butyl group, a pentyl group, a hexyl group, a heptyl group, an octyl group, a nonyl group, and a decyl group, each substituted with at least one selected from a deuterium, a halogen atom, a hydroxyl group, a cyano group, a nitro group, and an amino group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro fluorenyl group, a pyrrolyl group, a furyl group, a pyrazolyl group, an imidazolyl group, an oxazolyt group, an Isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, a benzimidazolyl group, a bensoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group and a benzocarbazole group, each substituted with at least one selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_4$-$C_{30}$ heteroaryl group, a $C_5$-$C_{30}$ aryloxy group, a $C_5$-$C_{30}$ arylthio group, and —Si($Q_{31}$)($Q_{32}$)($Q_{33}$), wherein $Q_{31}$ to $Q_{33}$ are each independently selected from a hydrogen, a $C_1$-$C_{10}$ alkyl group, a $C_1$-$C_{10}$ alkoxy group, and a $C_6$-$C_{20}$ aryl group.

6. The condensed cyclic compound of claim 1,
wherein an A part represented by a dotted line box in Formula 1 is selected from Formulae 2A to 2AA:

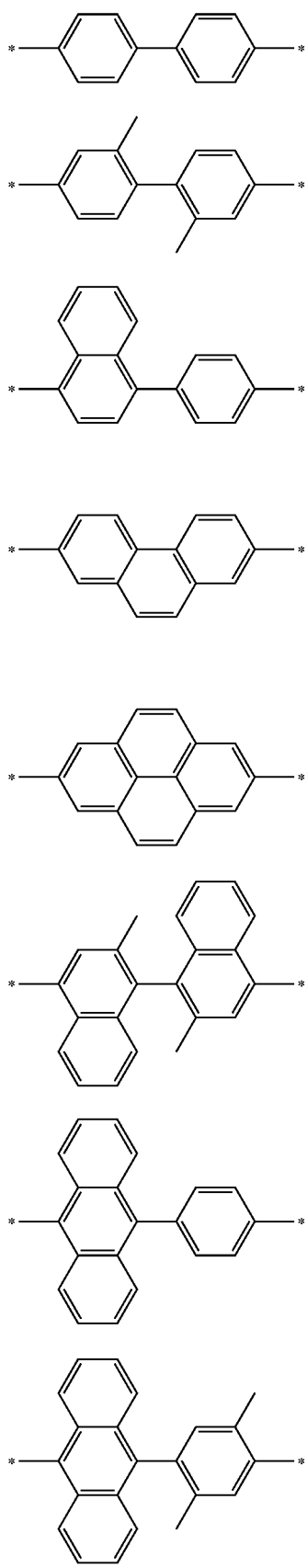
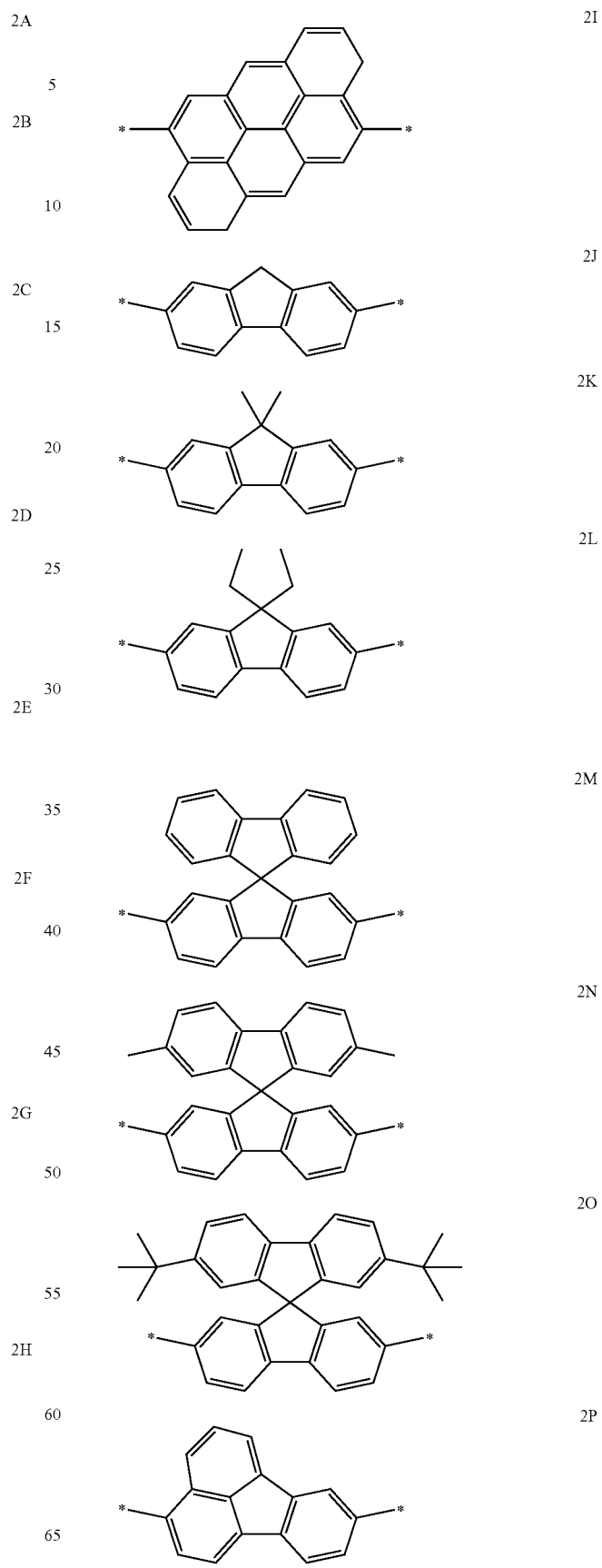

101
-continued
2Q
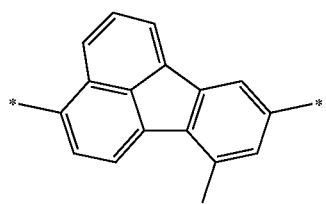
2R
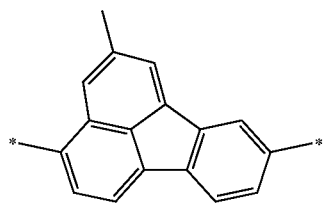
2S
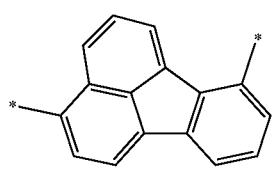
2T
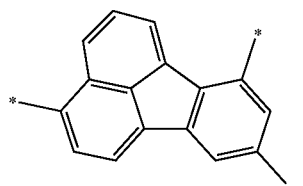
2U
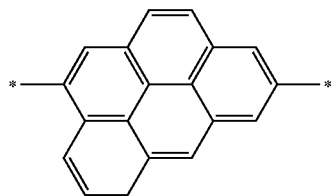
2V
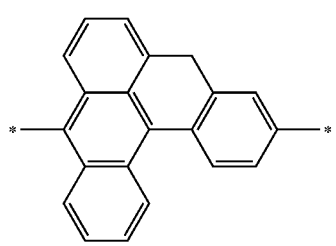
2W
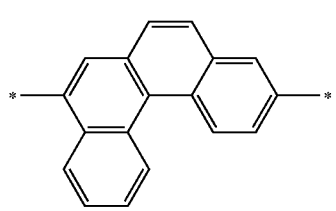
102
-continued
2X
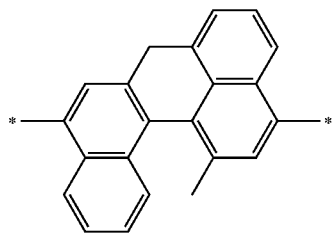
2Y
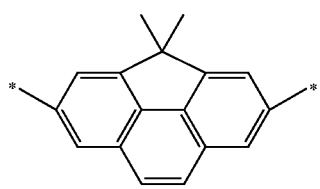
2Z
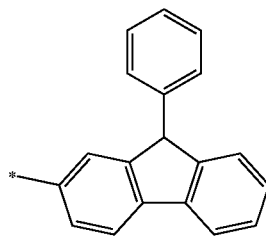
2AA
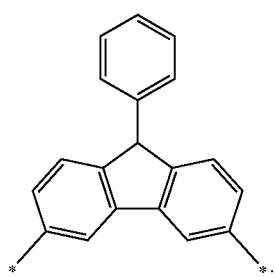
7. The condensed cyclic compound of claim 1, wherein B and C parts represented by dotted line boxes in Formula 1 are each independently selected from Formulae 3A to 3F:
3A
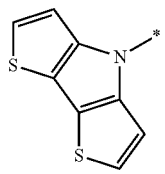
3B
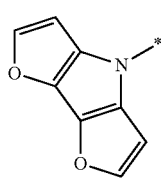

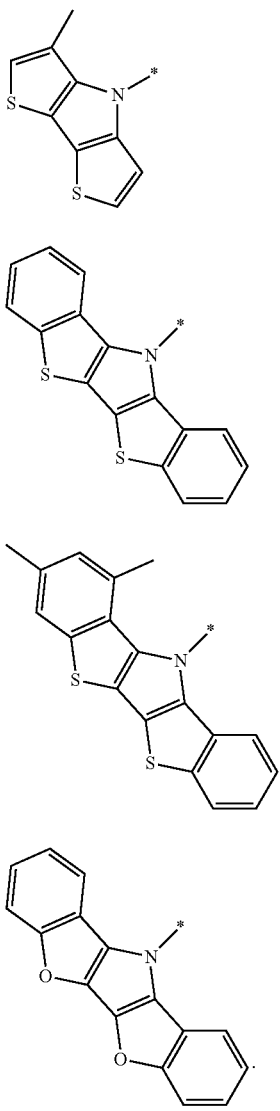

8. The condensed cyclic compound of claim 1, wherein the condensed cyclic compound is represented by any one of Formula 1-1 and Formula 1-2:

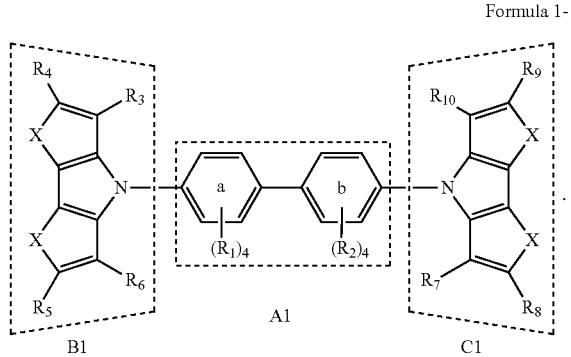

Formula 1-1

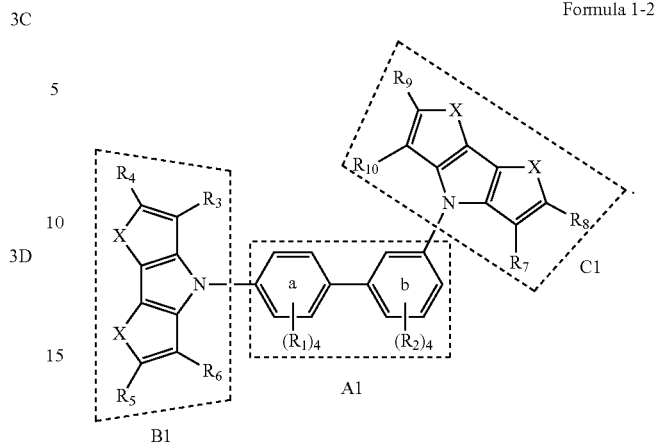

Formula 1-2

9. The condensed cyclic compound of claim 8,
wherein the plurality of $R_1$ are each independently selected from a hydrogen and a $C_1$-$C_{10}$ alkyl group,
or at least one $R_1$ of the plurality of $R_1$ is selected from a hydrogen and a $C_1$-$C_{10}$ alkyl group, and two or more $R_1$ of the plurality of $R_1$ different from the at least one $R_1$ of the plurality of $R_1$ are linked to each other to form a substituted or unsubstituted naphthylene group or a substituted or unsubstituted anthrylene group with the 'a' benzene ring, and
wherein at least one substituent of the substituted naphthylene group and the substituted anthrylene group is selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

10. The condensed cyclic compound of claim 8,
wherein the plurality of $R_2$ are each independently selected from a hydrogen and a $C_1$-$C_{10}$ alkyl group,
or at least one $R_2$ of the plurality of $R_2$ is selected from a hydrogen and a $C_1$-$C_{10}$ alkyl group, and two or more $R_2$ of the plurality of $R_2$ different from the at least one $R_2$ of the plurality of $R_2$ are linked to each other to form a substituted or unsubstituted naphthylene group or a substituted or unsubstituted anthrylene group with the 'b' benzene ring, and
wherein at least one substituent of the substituted naphthylene group and the substituted anthrylene group is selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.

11. The condensed cyclic compound of claim 8,
wherein at least one of the plurality of $R_1$ and the plurality of $R_2$ is selected from a hydrogen and a $C_1$-$C_{10}$ alkyl group,
and at least another one $R_1$ of the plurality of $R_1$ and at least another one $R_2$ the plurality of $R_2$ are linked to each other to form a substituted or unsubstituted $C_{13}$-$C_{30}$ condensed ring with the 'a' and 'b' benzene rings, and
wherein at least one substituent of the substituted $C_{13}$-$C_{30}$ condensed ring is selected from a deuterium, a halogen atom, a hydroxyl group, a cyano group, a nitro group, an amino group, a carboxylic acid or a salt thereof, a sulfonic acid or a salt thereof, a phosphoric acid or a salt thereof, a $C_1$-$C_{10}$ alkyl group, and a $C_6$-$C_{30}$ aryl group.
12. The condensed cyclic compound of claim 8, wherein an A1 part represented by dotted line boxes in Formula 1-1 and Formula 1-2 is selected from Formulae 2A to 2AA:
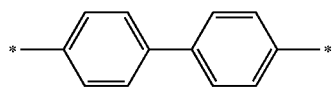
2A
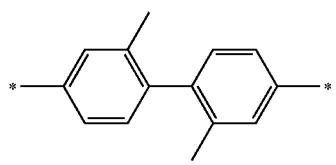
2B
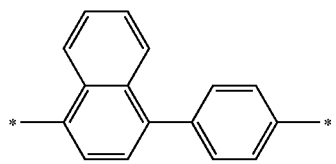
2C
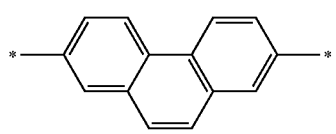
2D
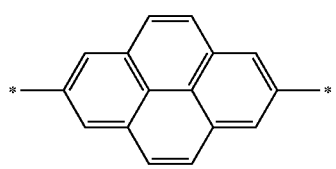
2E
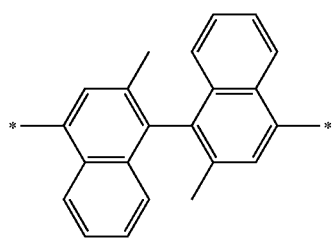
2F
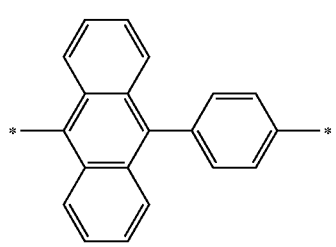
2G
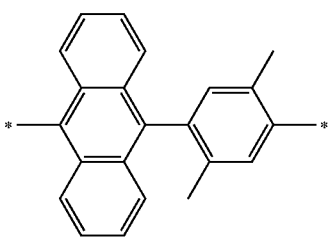
2H
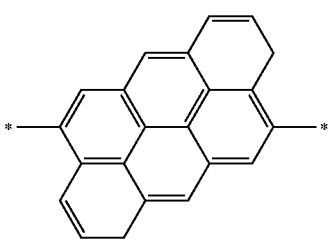
2I
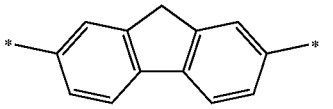
2J
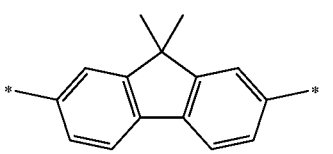
2K
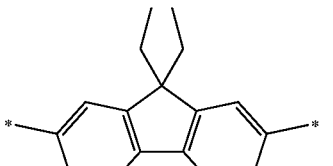
2L
2M
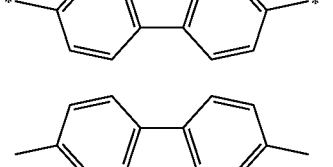
2N
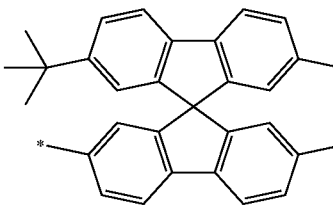
2O 107
-continued
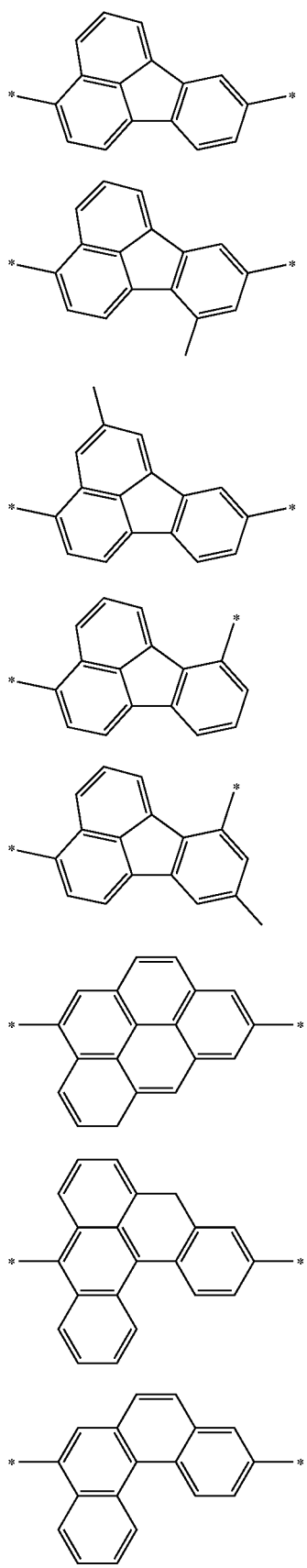
2P
2Q
2R
2S
2T
2U
2V
2W
108
-continued
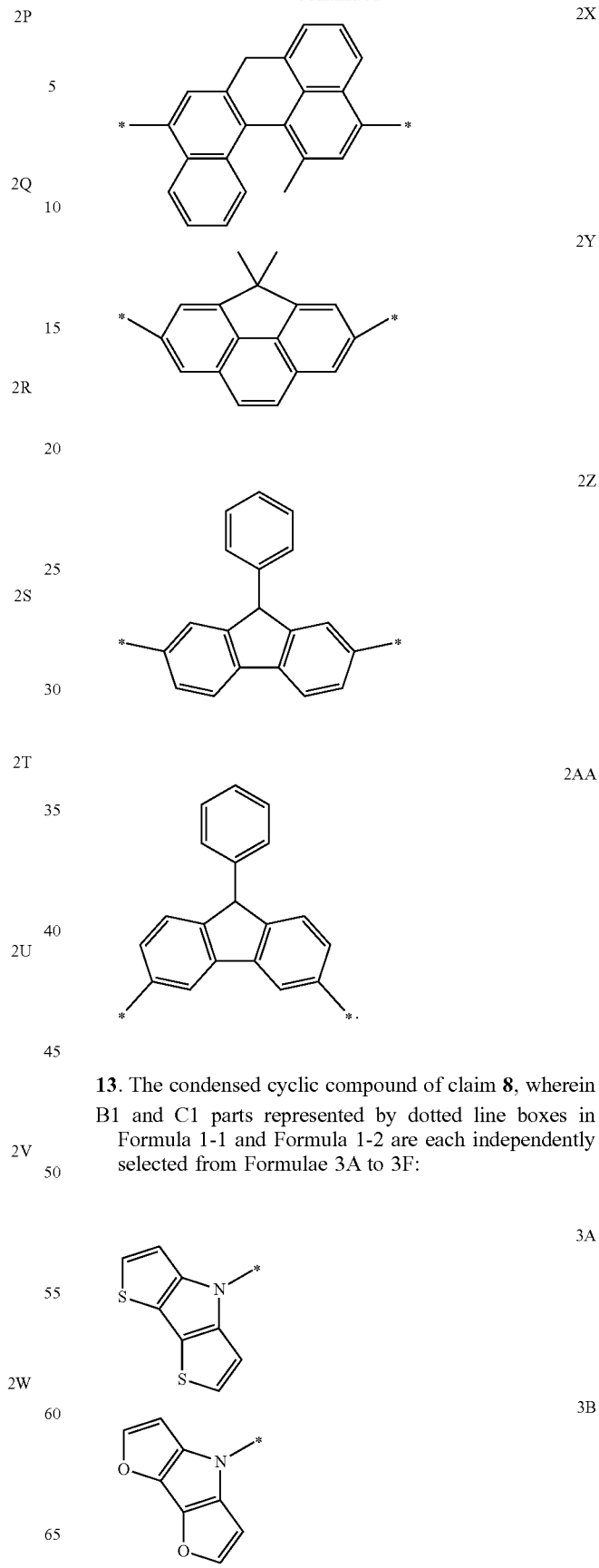
2X
2Y
2Z
2AA
13. The condensed cyclic compound of claim 8, wherein B1 and C1 parts represented by dotted line boxes in Formula 1-1 and Formula 1-2 are each independently selected from Formulae 3A to 3F:
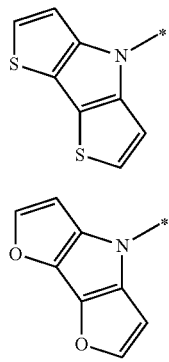
3A
3B 109
-continued
3C
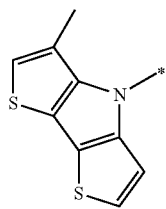
3D
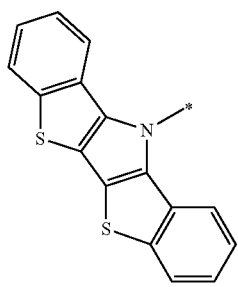
3E
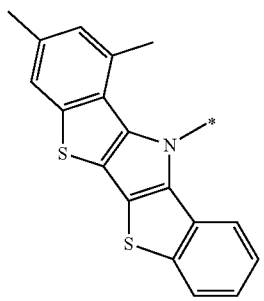
3F
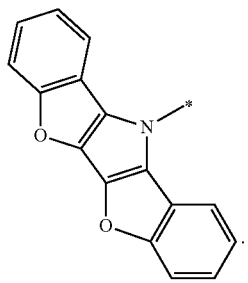
14. The condensed cyclic compound of claim 1, wherein the condensed cyclic compound is selected from one of Compounds 101 to 141:
101
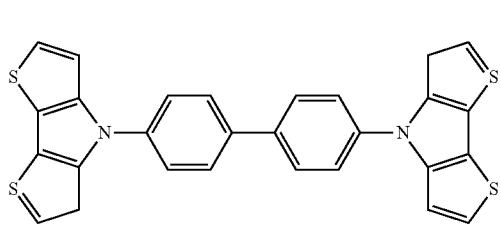
110
-continued
102
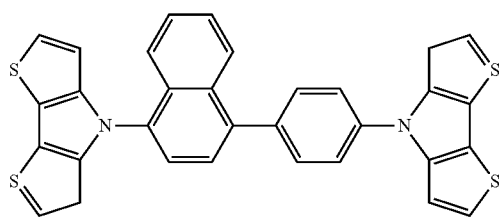
103
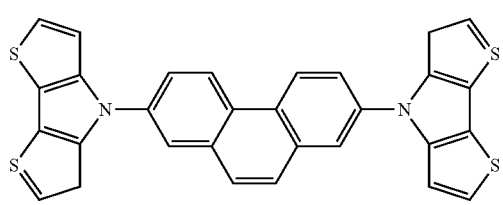
104
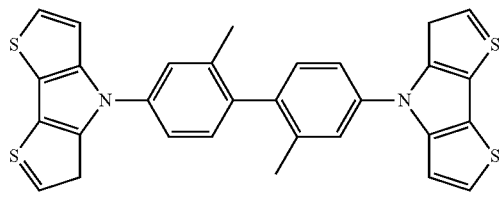
105
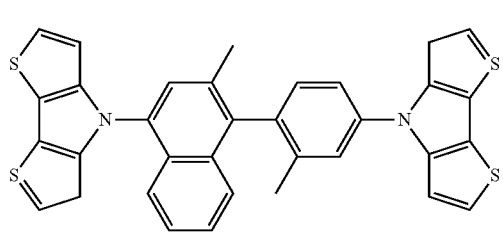
106
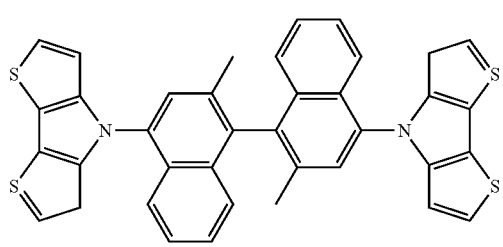
107
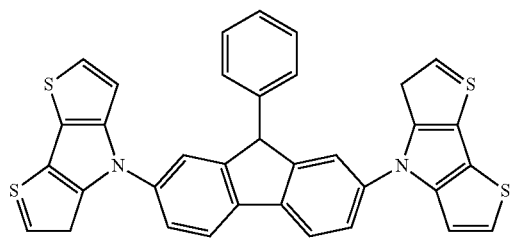

108
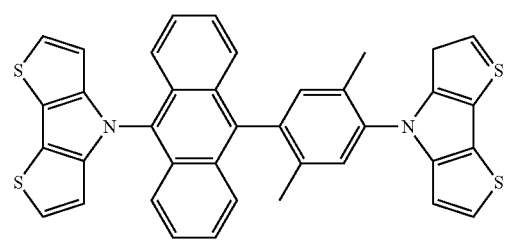
113
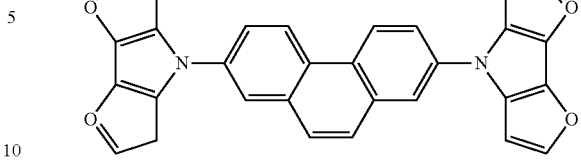
109
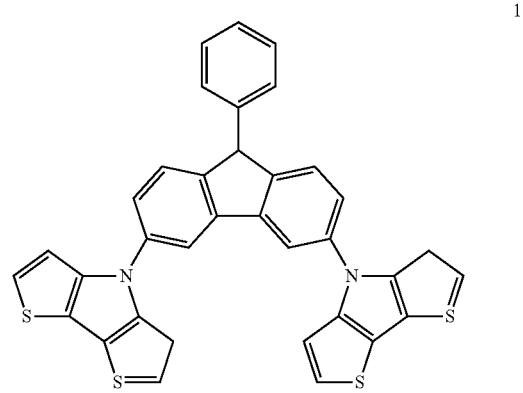
114
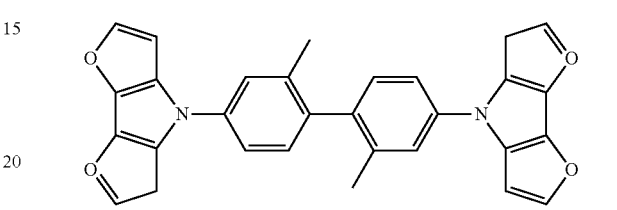
115
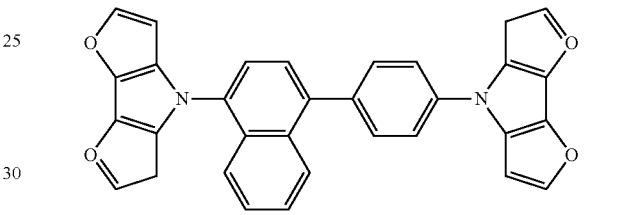
110
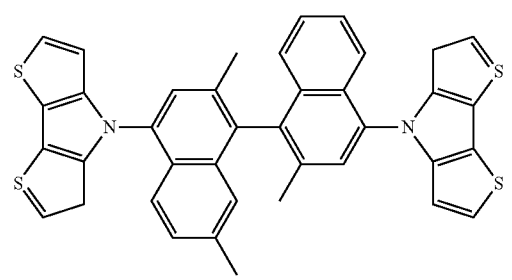
116
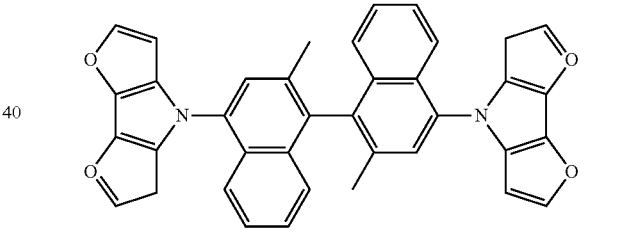
111
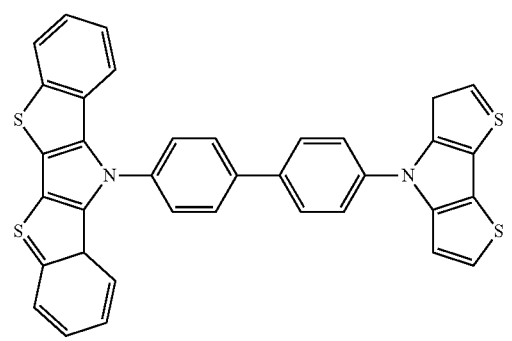
117
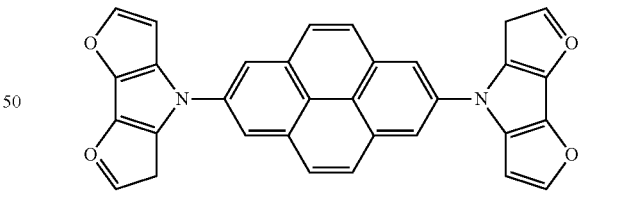
112
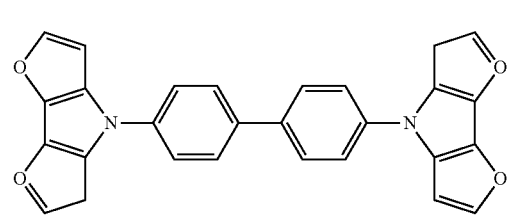
118
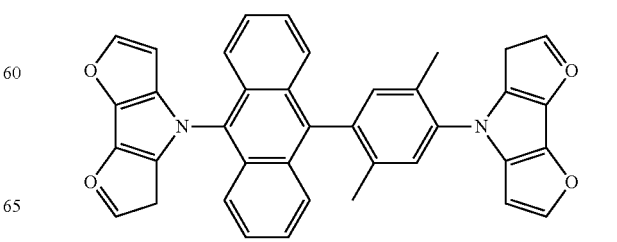

119
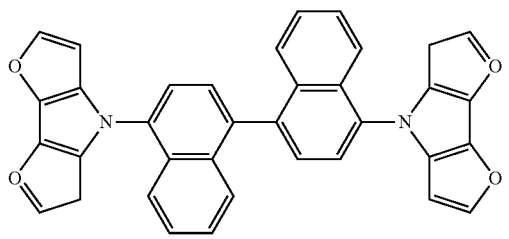
120
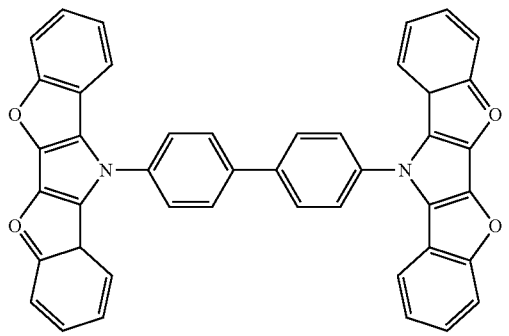
121
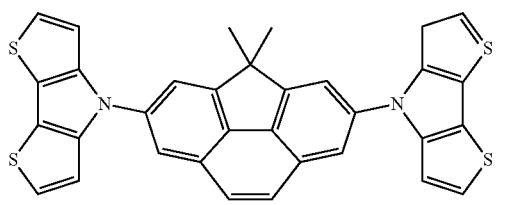
122
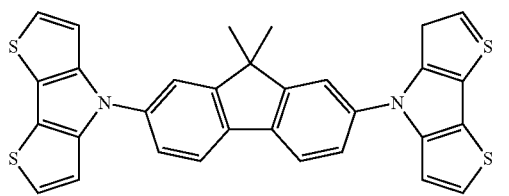
123
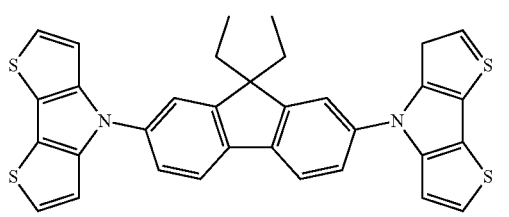
124
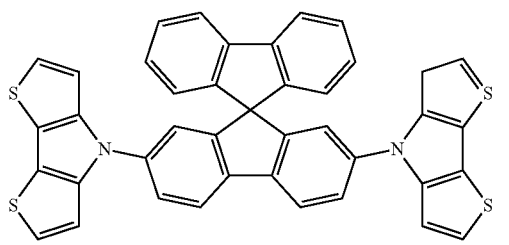
125
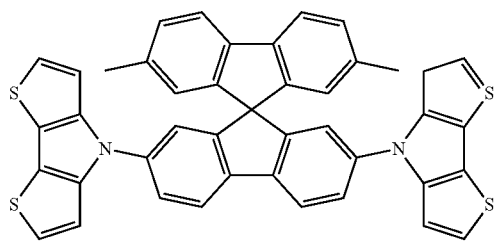
126
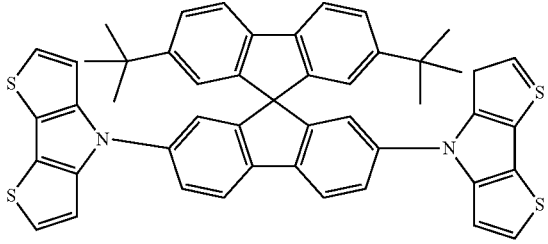
127
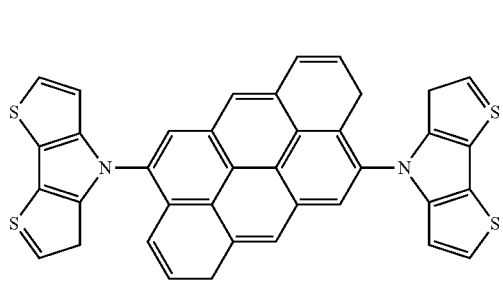
128
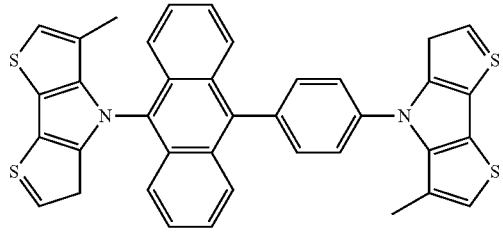
129
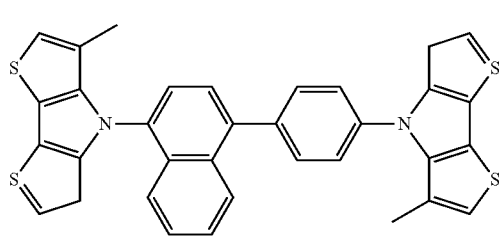

115
-continued
130
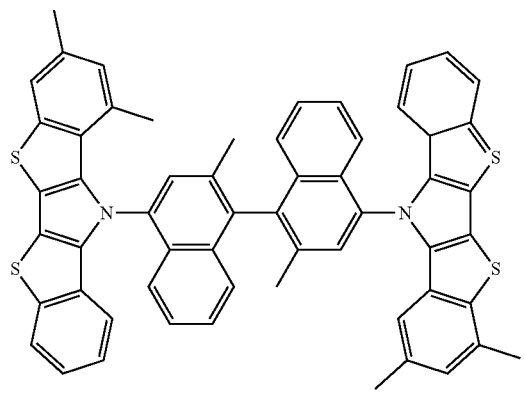
131
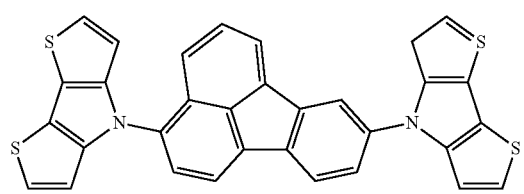
132
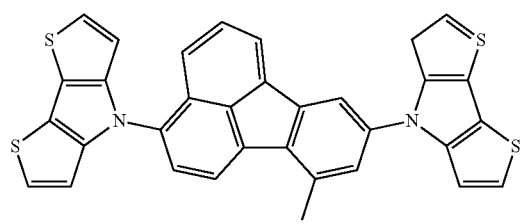
133
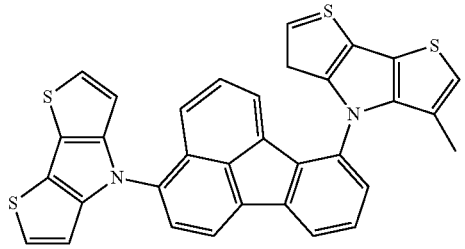
134
135
116
-continued
136
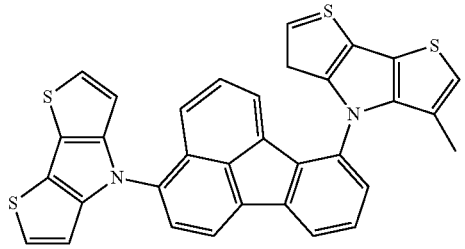
137
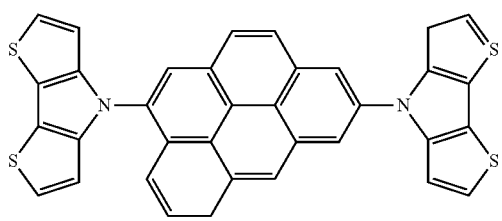
138
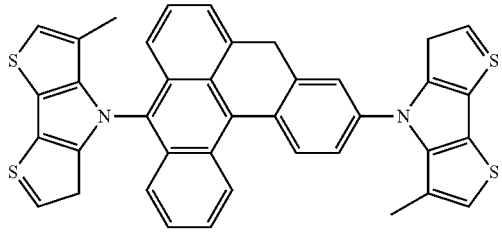
139
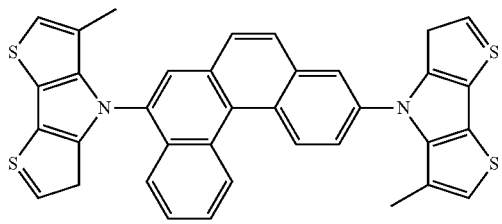
140
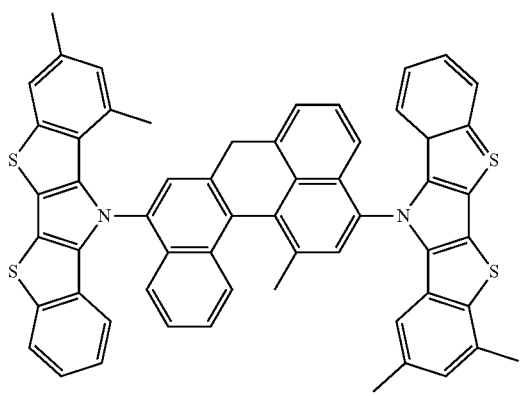

141

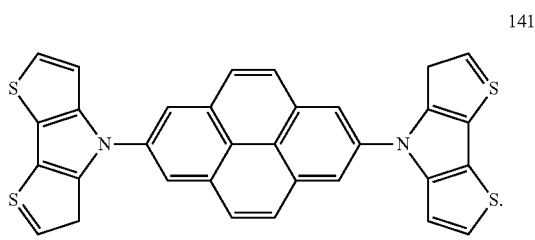

15. The condensed cyclic compound of claim 1, wherein the condensed cyclic compound is selected from Compounds 101, 107, 109, and 121:

101

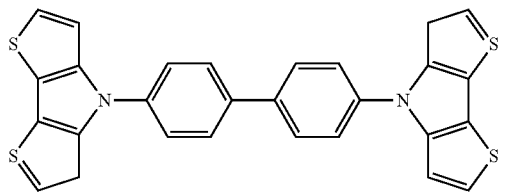

107

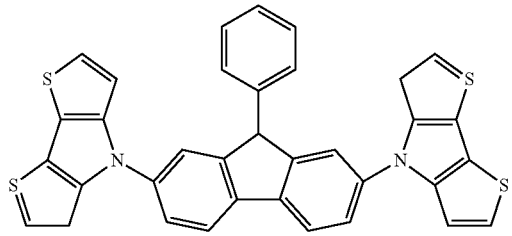

109

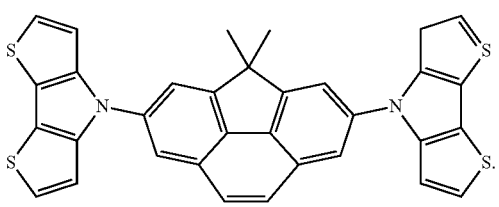

121

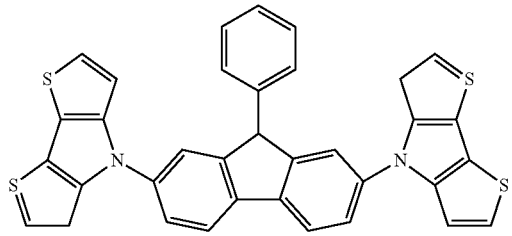

16. An organic light-emitting device, the organic light-emitting device comprising:
a first electrode;
a second electrode; and
an organic layer between the first electrode and the second electrode and comprising an emission layer and at least one condensed cyclic compound of claim 1.

17. The organic light-emitting device of claim 16, wherein the organic layer further comprises:
a hole transport region between the first electrode and the emission layer; and
an electron transport region between the emission layer and the second electrode.

18. The organic light-emitting device of claim 17, wherein the hole transport region comprises at least one selected from an electron blocking layer, a hole transport layer, and a hole injection layer.

19. The organic light-emitting device of claim 17, wherein the electron transport region comprises at least one selected from a hole blocking layer, an electron transport layer, and an electron injection layer.

20. The organic light-emitting device of claim 17, wherein the hole transport region comprises the condensed cyclic compound.

* * * * *